US012747472B2

(12) United States Patent
Kind et al.

(10) Patent No.: US 12,747,472 B2
(45) **Date of Patent: *Sep. 29, 2026**

(54) METHOD AND KIT FOR DETECTION OF PROTEIN-DNA MARKERS, SUCH AS PROTEIN-DNA INTERACTIONS AND/OR HISTONE MODIFICATIONS, IN CELLS

(71) Applicant: KONINKLIJKE NEDERLANDSE AKADEMIE VAN WETENSCHAPPEN, Amsterdam (NL)

(72) Inventors: Jop Haico Kind, Amsterdam (NL); Silke Johanna Anna Lochs, Amsterdam (NL); Robin Harm Willem Eric Van Der Weide, Amsterdam (NL)

(73) Assignee: KONINKLIJKE NEDERLANDSE AKADEMIE VAN WETENSCHAPPEN, Amsterdam (NL)

( * ) Notice: Subject to any disclaimer, the term of this patent is extended or adjusted under 35 U.S.C. 154(b) by 0 days.

This patent is subject to a terminal disclaimer.

(21) Appl. No.: 19/352,121

(22) Filed: Oct. 7, 2025

(65) Prior Publication Data

US 2026/0078442 A1 Mar. 19, 2026

Related U.S. Application Data

(63) Continuation of application No. 18/707,420, filed as application No. PCT/NL2022/050635 on Nov. 9, 2022.

(30) Foreign Application Priority Data

Nov. 9, 2021 (NL) ...................................... 2029695

(51) Int. Cl.
*C12Q 1/6869* (2018.01)
*C12Q 1/6806* (2018.01)

(52) U.S. Cl.
CPC ......... *C12Q 1/6869* (2013.01); *C12Q 1/6806* (2013.01)

(58) Field of Classification Search
CPC ............................ C12Q 1/6869; C12Q 1/6806
See application file for complete search history.

(56) References Cited

U.S. PATENT DOCUMENTS

2011/0189690 A1 8/2011 Shibasaki
2019/0270983 A1* 9/2019 Belhocine .......... C12N 15/1075
2020/0123591 A1 4/2020 Clarke

OTHER PUBLICATIONS

Okur et al., "CUT&Tag for efficient epigenomic profiling of small samples and single cells," Nature Communications, vol. 10, pp. 1-10. (Year: 2019).*

(Continued)

*Primary Examiner* — Young J Kim
(74) *Attorney, Agent, or Firm* — Greenberg Traurig, LLP; Wei Zhang

(57) ABSTRACT

A method for sequencing DNA wherein a sample comprising isolated cell nuclei is contacted with an antibody that forms a covalent conjugate with a first DNA adapter, and wherein the formed antibody-DNA conjugate can bind a protein of interest and ligate to an end of a dephosphorylated DNA fragment, and wherein the sample is then contacted with a second DNA adapter that coheres to the first DNA adapter of the antibody-DNA conjugate to obtain a second DNA adapter—first DNA adapter—DNA fragment product that allows for sequencing of an amplified product.

20 Claims, 24 Drawing Sheets

Specification includes a Sequence Listing.

(56) References Cited

OTHER PUBLICATIONS

Agard, Nicholas J., Jennifer A. Prescher, and Carolyn R. Bertozzi. "A strain-promoted [3+ 2] azide-alkyne cycloaddition for covalent modification of biomolecules in living systems." Journal of the American Chemical Society 126.46 (2004): 15046-15047.
Boggs, Barbara A., et al. "Reduced levels of histone H3 acetylation on the inactive X chromosome in human females." Chromosoma 105.5 (1996): 303-309.
International Search Report issued Feb. 6, 2023 for PCT/NL2022/050635, 4 pages.
Audia JE, Campbell RM. Histone Modifications and Cancer. Cold Spring Harb Perspect Biol. Apr. 1, 2016;8(4):a019521.
Becker PB, Workman JL. Nucleosome remodeling and epigenetics. Cold Spring Harb Perspect Biol. Sep. 1, 2013;5(9):a017905.
Belaghzal, Houda, Job Dekker, and Johan H. Gibcus. "Hi-C 2.0: An optimized Hi-C procedure for high-resolution genome-wide mapping of chromosome conformation." Methods 123 (2017): 56-65.
Boggs, Barbara A., et al. "Differentially methylated forms of histone H3 show unique association patterns with inactive human X chromosomes." Nature genetics 30.1 (2002): 73-76.
Burgess RJ, Zhang Z. Histone chaperones in nucleosome assembly and human disease. Nat Struct Mol Biol. Jan. 2013;20(1):14-22.
Ernst, Jason, et al. "Mapping and analysis of chromatin state dynamics in nine human cell types." Nature 473.7345 (2011): 43-49.
Gopalan, Sneha, et al. "Simultaneous profiling of multiple chromatin proteins in the same cells." Molecular cell 81.22 (2021): 4736-4746.
Harada, Akihito, et al. "A chromatin integration labelling method enables epigenomic profiling with lower input." Nature cell biology 21.2 (2019): 287-296.
Heard, Edith, et al. "Methylation of histone H3 at Lys-9 is an early mark on the X chromosome during X inactivation." Cell 107.6 (2001): 727-738.
Kind, Jop, et al. "Genome-wide maps of nuclear lamina interactions in single human cells." Cell 163.1 (2015): 134-147.
Ku, Wai Lim, et al. "Single-cell chromatin immunocleavage sequencing (scChIC-seq) to profile histone modification." Nature methods 16.4 (2019): 323-325.
Liu, Chih Long, Stuart L. Schreiber, and Bradley E. Bernstein. "Development and validation of a T7 based linear amplification for genomic DNA." BMC genomics 4.1 (2003): 19.
Okamoto, Ikuhiro, et al. "Epigenetic dynamics of imprinted X inactivation during early mouse development." Science 303.5658 (2004): 644-649.
Park PJ. ChIP-seq: advantages and challenges of a maturing technology. Nat Rev Genet. Oct. 2009;10(10):669-80.
Rooijers, Koos, et al. "Simultaneous quantification of protein-DNA contacts and transcriptomes in single cells." Nature biotechnology 37.7 (2019): 766-772.
Rougeulle, Claire, et al. "Differential histone H3 Lys-9 and Lys-27 methylation profiles on the X chromosome." Molecular and cellular biology 24.12 (2004): 5475-5484.
Sanborn, Adrian L., et al. "Chromatin extrusion explains key features of loop and domain formation in wild-type and engineered genomes." Proceedings of the National Academy of Sciences 112.47 (2015): E6456-E6465.
Van Buggenum, Jessie AGL, et al. "A covalent and cleavable antibody-DNA conjugation strategy for sensitive protein detection via immuno-PCR." Scientific reports 6.1 (2016): 22675.
Zhu, Chenxu, et al. "Joint profiling of histone modifications and transcriptome in single cells from mouse brain." Nature methods 18.3 (2021): 283-292.

* cited by examiner

SEQUENCE LISTING

```
Sequence total quantity: 12
SEQ ID NO: 1            moltype = DNA  length = 83
FEATURE                 Location/Qualifiers
misc_feature            1..83
```

```
                         note = artifical
source                   1..83
                         mol_type = other DNA
                         organism = synthetic construct
SEQUENCE: 1
gttggagttg aaacgttcta atattccaat cagcttcaac gtgcaccacc gcagggcggc  60
cgccttcaac atatgctagc atc                                          83

SEQ ID NO: 2             moltype = DNA  length = 83
FEATURE                  Location/Qualifiers
misc_feature             1..83
                         note = artificial
source                   1..83
                         mol_type = other DNA
                         organism = synthetic construct
SEQUENCE: 2
gttggagttg aaacgttcta atattccaat cagcttcaac gtgcaccacc gcagggcggc  60
cgcagccatc atatgctagc atc                                          83

SEQ ID NO: 3             moltype = DNA  length = 83
FEATURE                  Location/Qualifiers
misc_feature             1..83
                         note = artifical
source                   1..83
                         mol_type = other DNA
                         organism = synthetic construct
SEQUENCE: 3
gttggagttg aaacgttcta atattccaat cagcttcaac gtgcaccacc gcagggcggc  60
cgcacacgac atatgctacg tac                                          83

SEQ ID NO: 4             moltype = DNA  length = 83
FEATURE                  Location/Qualifiers
misc_feature             1..83
                         note = artificial
source                   1..83
                         mol_type = other DNA
                         organism = synthetic construct
SEQUENCE: 4
gatgctagca tatgttgaag gcggccgccc tgcggtggtg cacgttgaag ctgattggaa  60
tattagaacg tttcaactcc aac                                          83

SEQ ID NO: 5             moltype = DNA  length = 83
FEATURE                  Location/Qualifiers
misc_feature             1..83
                         note = artifical
source                   1..83
                         mol_type = other DNA
                         organism = synthetic construct
SEQUENCE: 5
gatgctagca tatgatggct gcggccgccc tgcggtggtg cacgttgaag ctgattggaa  60
tattagaacg tttcaactcc aac                                          83

SEQ ID NO: 6             moltype = DNA  length = 83
FEATURE                  Location/Qualifiers
misc_feature             1..83
                         note = artifical
source                   1..83
                         mol_type = other DNA
                         organism = synthetic construct
SEQUENCE: 6
gtacgtagca tatgtcgtgt gcggccgccc tgcggtggtg cacgttgaag ctgattggaa  60
tattagaacg tttcaactcc aac                                          83

SEQ ID NO: 7             moltype = DNA  length = 72
FEATURE                  Location/Qualifiers
misc_feature             1..72
                         note = artificial
misc_difference          57..59
                         note = n is a, c, g, or t
misc_difference          64..66
                         note = n is a, c, g, or t
source                   1..72
                         mol_type = other DNA
                         organism = synthetic construct
SEQUENCE: 7
ggtgatccgg taatacgact cactataggg gttcagagtt ctacagtccg acgatcnnna  60
ggcnnncatt ag                                                      72

SEQ ID NO: 8             moltype = DNA  length = 72
```

```
FEATURE                 Location/Qualifiers
misc_feature            1..72
                        note = artificial
misc_difference         57..59
                        note = n is a, c, g, or t
misc_difference         64..66
                        note = n is a, c, g, or t
source                  1..72
                        mol_type = other DNA
                        organism = synthetic construct
SEQUENCE: 8
ggtgatccgg taatacgact cactataggg gttcagagtt ctacagtccg acgatcnnnt  60
gagnnngcta ag                                                      72

SEQ ID NO: 9            moltype = DNA  length = 72
FEATURE                 Location/Qualifiers
misc_feature            1..72
                        note = artifical
misc_difference         57..59
                        note = n is a, c, g, or t
misc_difference         64..66
                        note = n is a, c, g, or t
source                  1..72
                        mol_type = other DNA
                        organism = synthetic construct
SEQUENCE: 9
ggtgatccgg taatacgact cactataggg gttcagagtt ctacagtccg acgatcnnng  60
agannngcta ag                                                      72

SEQ ID NO: 10           moltype = DNA  length = 76
FEATURE                 Location/Qualifiers
misc_feature            1..76
                        note = artificial
misc_difference         11..13
                        note = n is a, c, g, or t
misc_difference         18..20
                        note = n is a, c, g, or t
source                  1..76
                        mol_type = other DNA
                        organism = synthetic construct
SEQUENCE: 10
ggccctaatg nnngcctnnn gatcgtcgga ctgtagaact ctgaacccct atagtgagtc  60
gtattaccgg gagctt                                                  76

SEQ ID NO: 11           moltype = DNA  length = 76
FEATURE                 Location/Qualifiers
misc_feature            1..76
                        note = artifical
misc_difference         11..13
                        note = n is a, c, g, or t
misc_difference         18..20
                        note = n is a, c, g, or t
source                  1..76
                        mol_type = other DNA
                        organism = synthetic construct
SEQUENCE: 11
ggcccttagc nnnctcannn gatcgtcgga ctgtagaact ctgaacccct atagtgagtc  60
gtattaccgg gagctt                                                  76

SEQ ID NO: 12           moltype = DNA  length = 76
FEATURE                 Location/Qualifiers
misc_feature            1..76
                        note = artifical
misc_difference         11..13
                        note = n is a, c, g, or t
misc_difference         18..20
                        note = n is a, c, g, or t
source                  1..76
                        mol_type = other DNA
                        organism = synthetic construct
SEQUENCE: 12
ggcccttagc nnntctcnnn gatcgtcgga ctgtagaact ctgaacccct atagtgagtc  60
gtattaccgg gagctt                                                  76
```

METHOD AND KIT FOR DETECTION OF PROTEIN-DNA MARKERS, SUCH AS PROTEIN-DNA INTERACTIONS AND/OR HISTONE MODIFICATIONS, IN CELLS

CROSS REFERENCE

This application is a continuation of U.S. application Ser. No. 18/707,420, filed May 3, 2024, which is a national stage entry of International Application No. PCT/NL2022/050635, filed Nov. 9, 2022, which claims priority to NL Application No. 2029695, filed Nov. 9, 2021, all of which are hereby incorporated by reference in their entirety.

SEQUENCE LISTING

The instant application contains a Sequence Listing which has been submitted electronically in XML format and is hereby incorporated by reference in its entirety. Said XML copy, created on Nov. 11, 2025, is named 231624-701301_SL.xml and is 21,518 bytes in size.

FIELD OF THE INVENTION

This invention pertains in general to a method for sequencing DNA of one or more cells. More in particular, the method may be used for detection of protein-DNA markers, such as protein-DNA interactions and/or histone modifications, in cells. The method allows identifying and quantifying an epigenetic signature of a cell, identifying and quantifying disease-related biomarkers, diagnosing diseases in subjects and screening for agents that may modify an epigenetic signature. The invention further pertains to a kit and for use thereof in the method of the invention.

BACKGROUND OF THE INVENTION

The background description includes information that may be useful in understanding the present invention. It is not an admission that any of the information provided herein is prior art or relevant to the presently claimed invention, or that any publication specifically or implicitly referenced is prior art.

Understanding the complex biological systems of a cell is crucial for understanding gene-activity related pathologies, for example cancer. In such pathologies it is not uncommon that the pathology originates in a single cell or in a few cells and expands rapidly to surrounding tissue. Identification and quantification of the epigenetic signature of a cell can provide detailed insights in a cell's identity and combinatorial events in the complex biological systems of cells, subsequently allowing a better understanding of gene-regulatory responses and allowing for unravelling the mechanisms that govern cell fate choice.

Methods in the art allow for profiling epigenetic profiles have been described but often the design of these methods does not or only to a limited extent potentiate the profiling of multiple signatures or marks in the same cell. Moreover, methods that enable the quantification of histone post-translational modification signatures of a cell, such as chromatin immuno-cleavage sequencing (ChIC-sequencing) and chromatin immunoprecipitation sequencing (ChIP-sequencing) are restricted to measuring only a single modality (Ku, Wai Lim et al. Nat. Meth. vol. 16, 4 (2019): 323-325.; Park, P. Nat Rev Genet 10, 669-680 (2009)).

The current inability to directly detect and quantify larger number of epigenetic modifications, including histone post-translational modifications, regulatory proteins, chromatin structure and DNA modification in a cell, explains the need for providing further methods for identifying multiple epigenetic modifications in a cell. In addition, there remains a general need for improved methods for detection of protein-DNA markers, such as protein-DNA interactions and/or histone modifications.

In light of this, new methods and uses for sequencing DNA, for example for detection of protein-DNA markers, such as protein-DNA interactions and/or histone modifications, in cells would be highly desirable, but are not yet readily available. In particular, there is a clear need in the art for reliable, efficient and reproducible products, compositions, methods and uses that allow, for example, assessment, for example simultaneous assessment, of one or multiple marks, such a protein-DNA interactions and/or histone modifications, in cells, such as single cells, using a single assay. Accordingly, the technical problem underlying the present invention can been seen in the provision of such products, compositions, methods and uses for complying with any of the aforementioned needs. The technical problem is solved by the embodiments characterized in the claims and herein below.

SUMMARY OF THE INVENTION

The current inventors now provide for a new and inventive method of sequencing DNA and/or a method for obtaining DNA sequence information, in particular for use in detection of protein-DNA markers, such as protein-DNA interactions and/or histone modifications, in cells. Methods available in the art, although useful, are rather restricted to one, at most three, readouts in a single cell. This means that state of the art methods are largely dependent on performing multiple assays in order to 1) screen multiple parameters at a single cell resolution, or 2) screen a single parameter in multiple cells.

The current inventors now have developed a method that allows for the assessment of marks, preferably simultaneous assessment of multiple marks, in cells, preferably single cells, using a single assay. The inventors developed a method that optimizes the number of single cell read-outs and allows for measuring in principal unlimited combinations of gene-regulatory proteins and epigenetic modifications in one cell or in more than one cell.

The inventors found that the newly developed method for the first time allows the identification of a combined epigenomic signatures associated with cell identities and for obtaining detailed insight in mechanisms that govern cell identities. The current inventors surprisingly found that by means of the method of sequencing DNA in accordance with the invention multidimensional single-cell data from complex biological systems can be obtained, permitting the identification of the interconnectivity between genomic features and epigenomic features associated with cellular identities, cellular development and cellular pathology.

It is contemplated by the inventors that by using the method of the invention in cancer models, e.g. in vivo mouse models, also allows for revealing early epigenetic biomarkers and subsequently permits the identification of one or more epigenetic modifications for potential drug targeting. At the same time it is contemplated that with the method according to the invention is a valuable tool for revealing a sequence of events that leads up to changes in gene-activities, e.g. the first binding of a transcription factor and the consequential epigenetic modifications, or vice versa.

An additional benefit of the method, surprisingly discovered by the inventors, is that it does not suffer from large losses of sequenceable material, for example compared to state of the art methods such as ChIP-sequencing, because the current method does not depend on a pull-down assay.

Overall, the inventors found that with the method of the invention the profiling of multiple epigenetic profiles in the same cell can be realized. The method greatly improves state of the art methods that do not allow this.

The method according to the invention is broadly based on the use of antibody-DNA adapter conjugates: the antibody part recognizes a specific protein or modification of interest, and that is suspected to interact with, for example, genomic DNA present in a cell. The DNA adapter part enables ligation of the antibody-DNA adapter conjugate into the (e.g. genomic) DNA at the location where the protein or modification of interest is detected (by the antibody part of the antibody-DNA adapter conjugate). The invention may include barcoding, where firstly each antibody-DNA adapter conjugate contains a barcode encoding/identifying the protein or modification of interest (by means of the antibody in the antibody-DNA adapter conjugate directed to such protein of interest or modification of interest). Secondly, an additional barcode may be ligated to encode the specific sample/cell.

The obtained molecule may be amplified and sequenced in order to provide sequence information with respect to the original DNA that interacted with the protein of interest and/or the modification of interest, therewith providing valuable information, for example on the localization where the interaction between the protein/the modification and the DNA occurred, the cell wherein the event took places and/or the type of protein and/or modification that can interact at a particular localization in the genome./pct The method enables high throughput screening of multiple parameters in a single assay at single cell resolution. The method of the current invention, using the antibody-DNA adapter conjugate as described herein allows to site-specifically label and barcode the genome in proximity of the protein location (e.g. transcription factor or histone posttranslational modification), thus creating a nucleic acid molecule that can be amplified and sequenced.

The invention is defined herein, and in particular in the accompanying claims.

The invention not only allows for a high number of measurements in a single reaction tube or samples, even in the same single cell, but also allows for single-cell analysis in said single reaction sample. Moreover, beneficially the method requires the use of common commercially available materials making the method cost-effective, reproducible, and implementable in most molecular biology laboratories.

Hence, there is provided for the use of a method in accordance with the invention for generating genome-wide protein-DNA interaction profiles, genome-wide epigenetic profiles, comparing between cell-type specific epigenetic and/or protein-DNA interaction profiles or comparing between epigenetic and/or protein-DNA interaction profiles between embryos at different developmental stages, comparing between epigenetic and/or protein-DNA interaction profiles in tumorigenesis at different disease stages, following different treatment regimes, analysis of protein-DNA interaction at different loci, comparing protein-DNA interaction between one or more samples obtained, comparing protein DNA-interaction between diseased and healthy tissue or between different parts of an organism.

BRIEF DESCRIPTION OF THE DRAWINGS

FIG. 10 shows single read counts in single cells obtained with multiplexed immuno-detection of RNA Polymerase 2, H3K36me3, H3K27me3 and Histone H3 in single cells.

DESCRIPTION

Definitions

Figure 1:
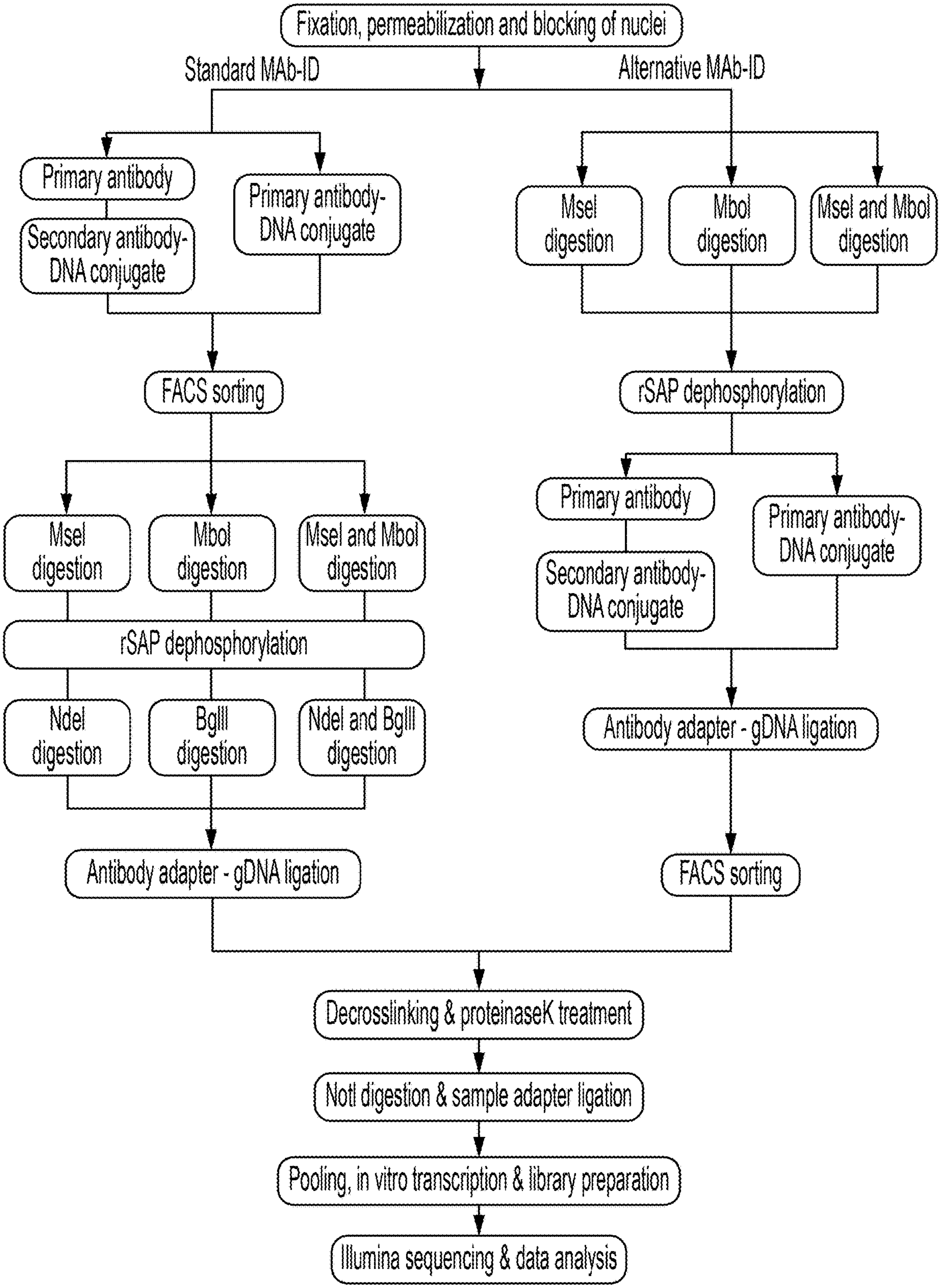
FIG. 1: Flow chart of non-limiting examples/embodiments by which the method of the invention may be performed.

A portion of this disclosure contains material that is subject to copyright protection (such as, but not limited to, diagrams, device photographs, or any other aspects of this submission for which copyright protection is or may be available in any jurisdiction.). The copyright owner has no objection to the facsimile reproduction by anyone of the patent document or patent disclosure, as it appears in the Patent Office patent file or records, but otherwise reserves all copyright rights whatsoever.

Various terms relating to the methods, compositions, uses and other aspects of the present invention are used throughout the specification and claims. Such terms are to be given their ordinary meaning in the art to which the invention pertains, unless otherwise indicated. Other specifically defined terms are to be construed in a manner consistent with the definition provided herein. Although any methods and materials similar or equivalent to those described herein can be used in the practice for testing of the present invention, the preferred materials and methods are described herein. For purposes of the present invention, the following terms are defined below.

As used herein, the singular forms "a," "an" and "the" include plural referents unless the context clearly dictates otherwise. For example, "a method for providing a cell" includes the providing of a plurality of cells (e.g. 10's, 100's, 1000's, 10's of thousands, 100's of thousands, millions, or more cells). For example, "a first antibody-DNA adapter conjugate" includes providing a plurality of such "first antibody-DNA adapter conjugates".

The terms "about" and "approximately", when referring to a measurable value such as an amount, a temporal duration, and the like, is meant to encompass variations of ±20% or ±10%, more preferably ±5%, even more preferably ±1% and still more preferably ±0.1% from the specified value, as such variations are appropriate to perform the disclosed methods.

As used herein, the term "and/or" indicates that one or more of the stated cases may occur, alone or in combination with at least one of the stated cases, up to with all of the stated cases.

As used herein, the term "at least" a particular value means that particular value or more. For example, "at least 2" is understood to be the same as "2 or more" i.e., 2, 3, 4, 5, 6, 7, 8, 9, 10, 11, 12, 13, 14, 15, . . . , etc. As used herein, the term "at most" a particular value means that particular value or less. For example, "at most 5" is understood to be the same as "5 or less" i.e., 5, 4, 3, . . . −10, −11, etc.

As used herein, the word "comprise" or variations thereof such as "comprises" or "comprising" will be understood to include a stated element, integer or step, or group of elements, integers or steps, but not to exclude any other element, integer or steps, or groups of elements, integers or steps. The verb "comprising" includes the verbs "essentially consisting of" and "consisting of".

As used herein, "conventional techniques" or "methods known to the skilled person" refer to a situation wherein the methods of carrying out the conventional techniques used in methods of the invention will be evident to the skilled worker. The practice of conventional techniques in molecular biology, biochemistry, cell culture, genomics, sequencing, medical treatment, pharmacology, immunology and related fields are well-known to those of skill in the art and are discussed, in various handbooks and literature references.

As used herein, "exemplary" or "for example" means "serving as an example, instance, or illustration," and should not be construed as excluding other configurations, including those disclosed herein.

As used herein, the term "binds" or variations thereof such as of "binding", "bind" will be understood to comprise an attractive interaction between molecules that results in a stable association in which the molecules are in close proximity to each other. Said attraction between molecules can be due to covalent binding, non-covalent binding etc. As used herein when directed to DNA and/or protein molecules said attraction can be due to, but is not limited to, van der Waals forces, hydrogen interactions, steric interactions, electrostatic charge patterns recognition etc.

As used herein the terms "protein of interest", used interchangeably with "polypeptide of interest" or "peptide of interest", refers to a biomolecule consisting of a polymer chain of amino acid residues that is of particular interest in a scientific or technical purpose of the method of the invention, for example, but not limited to diagnostic purposes, analytical purposes, medical purposes.

As used herein the term "post-translational modification" refers to a modification of a natural amino acid or of a non-natural amino acid, typically occurring subsequently to the in vivo or in vitro inclusion of said amino acid in a polypeptide.

DETAILED DESCRIPTION

The inventors found that with the method of the invention the profiling of multiple epigenetic profiles in the same cell can be realized. The method greatly improves state of the art methods that do not allow this, or only to a very limited extent. At the same time, interaction of proteins of interest with DNA, for example genomic DNA may be studied, including studies on the manipulation of such interactions (for example in screening assays for compounds that affect protein of interest interaction with DNA, for example integration with DNA on one or more predefined positions in the DNA, e.g. genome).

The method according to the invention is broadly based on the use of antibody-DNA adapter conjugates: the antibody part recognizes a specific protein or modification of interest (directly or indirectly via an intermediate antibody, as described herein), and that is suspected to interact with, for example, genomic DNA present in a cell. The DNA adapter part enables ligation of the antibody-DNA adapter conjugate into the (e.g. genomic) DNA at the location where the protein (including modified protein, for example by post translational modifications) is present/detected (by the antibody part of the antibody-DNA adapter conjugate). The invention may include barcoding, where firstly each antibody-DNA adapter conjugate contains a barcode encoding/identifying the protein or modification of interest (by means of the antibody in the antibody-DNA adapter conjugate directed to such protein of interest or modification of interest). Secondly, an additional barcode may be ligated to encode the specific sample/cell.

The obtained molecule may be amplified and sequenced in order to provide sequence information with respect to the original DNA that interacted with the protein of interest and/or the modification of interest, therewith providing valuable information, for example on the localization where the interaction between the protein/the modification and the DNA occurred, the cell wherein the event took places and/or the type of protein and/or modification that can interact at a particular localization in the genome. Accordingly, the invention provides for a method of sequencing DNA, or, in other words to obtain sequence information regarding DNA that is present in a sample. Accordingly, the invention provides for a method for studying interaction of a protein, or protein complex, with DNA. Accordingly, the invention provides for a method for studying interactions of multiple proteins (or complexes) with multiple locations in the DNA.

Accordingly, the invention provides for a method of sequencing DNA, the method comprising the steps of:

(a) providing a sample comprising one or more permeabilized and fixated cell nuclei comprising DNA;

(b) treating the one or more cell nuclei comprising DNA by (i) digesting the DNA with a first restriction endonuclease to provide DNA fragments and dephosphorylating the 5'-end of the DNA fragments to provide dephosphorylated DNA fragments;

(ii) contacting, before, during, or after step (i), the one or more cell nuclei comprising DNA (1) with one or more first antibody-DNA adapter conjugates, and/or (2) with one or more first antibodies and one or more first antibody-DNA adapter conjugates, wherein the first antibody is directed against a protein of interest suspected to interact with DNA wherein the first antibody-DNA adapter conjugate comprises a first antibody part that is conjugated to a first DNA adapter part, and wherein in situation (1) the first antibody part is directed against a protein of interest suspected to interact with DNA and wherein in situation (2) the first antibody part is directed against the first antibody, and wherein an end of the first DNA adapter part is cohesive or is made cohesive to an end of the dephosphorylated DNA fragments defined in step (i), and wherein the first DNA adapter part comprises a second restriction site for a second restriction endonuclease, and, preferably, wherein the first DNA adapter part comprises a first barcode sequence, wherein the first barcode sequence is positioned between the end of the first DNA adapter part that is cohesive or is made cohesive to an end of the dephosphorylated DNA fragments defined in step (i) and the second restriction site, wherein the contacting is under conditions that allows (1) the antibody part of the first antibody-DNA adapter conjugate or (2) the antibody, and the antibody part of the first antibody-DNA adapter conjugate to bind with its target(s) in order to provide for a first antibody-DNA adapter conjugate that is bound to the protein of interest, (iii) allowing the first DNA adapter part of the first antibody-DNA adapter conjugate to ligate to an end of the dephosphorylated DNA fragments in order to obtain a first-DNA adapter-DNA fragment product;

(c) treating the sample obtained after step (b) by (i) degrading protein, preferably by conducting a protein degradation enzyme treatment, preferably wherein the enzyme comprises proteinase K, and/or by heat treatment, and, lysing the nuclei; and (ii) treating before or after (i) the DNA in the sample with the second restriction endonuclease thereby introducing a cut at the second restriction site that is comprised in the first DNA adapter part;

(d) incubating the sample obtained after step (c) with a second DNA adapter, wherein an end of the second DNA adapter is cohesive, preferably wherein the cohesive end has a 5'end phosphate group, to the end created at the second restriction site of the first DNA adapter in step (c) (ii), and wherein the second DNA adapter comprises a RNA polymerase binding sequence and/or a DNA primer sequence, and preferably further comprises a second barcode sequence, preferably wherein the second barcode sequence is positioned between the RNA polymerase binding sequence and the end that is cohesive to the end created at the second restriction site of the first DNA adapter in step (c) (ii), wherein the contacting is under conditions that allow the second DNA adapter to ligate to the end created at the second restriction site of the first DNA adapter part in step (c) (ii) in order to obtain a second DNA adapter—first DNA adapter—DNA fragment product;

(e) amplifying the second DNA adapter—first DNA adapter—DNA fragment product and sequencing the obtained amplified product.

In the method of the invention a sample comprising one or more permeabilized and fixated cell nuclei comprising DNA is provided. Methods for permeabilizing and fixating cell nuclei are well known in the art and can be widely implemented by a skilled person, and include method based on permeabilization and fixation by ethanol and/or acetone, detergents such a Tween20, (para)formaldehyde, glutaraldehyde alone, or in combination. In preferred embodiments, permeabilization and fixating may also include a step of blocking, for example using a solution containing an excess of protein, for example albumin such as BSA, that serves to reduce the amount of nonspecific binding in the sample. However, the skilled person understands that such blocking step may be performed any time (including more than one time) before the samples are contacted with the first antibodies and/or first antibody parts as disclosed herein. Within the context of the current invention any method for providing permeabilized and fixated cell nuclei is deemed suitable as long as the obtained nuclei still comprise DNA (and protein that may interact with such DNA) that was originally presented in the cell nuclei.

As disclosed herein elsewhere, the cell nuclei may be obtained from any source including animal cells, such as human cells. The cells may be obtained from cell culture or from an organism. In some embodiments of the method of the invention the method is performed on a single cell nucleus. In other embodiments more than one nucleus, i.e. nuclei are provided in step (a) of the method of the invention. Non-limiting examples include that more than 10, 20, 100 or 1000 cell nuclei, for example .g. 10's, 100's, 1000's, 10's of thousands, 100's of thousands, millions, or more, are provided in step (a) of the method of the invention.

In a next step (b), the nucleus or nuclei provided in step (a) is treated.

The treatment comprises (i) digesting the DNA that is comprised in the nucleus or nuclei with a first restriction endonuclease to provide DNA fragments and dephosphorylating the 5'-end of the DNA fragments to provide dephosphorylated DNA fragments.

The treatment also comprises (ii) contacting the one or more nuclei with one or more first antibody-DNA adapter conjugates, wherein a first antibody-DNA adapter conjugate (i.e. the first antibody part thereof) is directed to a protein of interest and/or contacting the one or more nuclei with one or more first antibodies and one or more first antibody-DNA adapter conjugates, wherein the first antibody is directed against a protein of interest, i.e. a protein of interest suspected to interact with DNA and the first antibody-DNA adapter conjugate (i.e. the first antibody part thereof) is directed against said first antibody.

In one embodiment the first antibody-DNA adapter comprises one DNA adapter. In some embodiments, a first antibody-DNA adapter conjugate comprises more than one, for example two, three, four or five, six, or more DNA adapters. In such embodiment, the ratio antibody:DNA adapter in the antibody-DNA adapter conjugate is in a ratio of 1:1, 1:2, 1:3, 1:4. 1:5, 1:6 or more. The inventors found that conjugation of multiple DNA adapters to the same first antibody-DNA adapter conjugate potentiates multiple ligation events of the same DNA adapter to the genomic DNA per bound protein of interest. In embodiment of the invention, the more than one DNA adapter in a (single) first antibody-DNA adapter conjugate are the same; i.e. more than one identical DNA adapter in the same first antibody-DNA adapter conjugate. In some embodiments, more than one type of DNA adapter is used in the same first antibody-DNA adapter conjugate. For example, the more than one type of DNA adapter may differ in length, in sequence, or for example, in cohesiveness to its target, as disclosed herein.

Thus, in a further embodiment, the same (single) first antibody-DNA adapter conjugate comprises more than one, for example two, three, four, five, six, or more different DNA adapters. Thus, in such embodiment, the ratio antibody: DNA adapter (part) in the first antibody-DNA adapter conjugate can be in a ratio of 1:1, 1:2, 1:3, 1:4, 1:5 or 1:6, albeit the different DNA-adapters comprised in the single first antibody-DNA adapter may not all be identical, e.g. one or more may be different (different type). The inventors found that conjugation of multiple different DNA adapters to the same first antibody-DNA adapter conjugate potentiates the increase of chance of a successful ligation of one or more of the different DNA adapters to the genomic DNA.

The treatments (i) and (ii) may be performed in any order, either sequentially or (partial) simultaneously. For example (i) may be performed before, during, or after (ii). For example (ii) may be performed before, during, or after (i).

The treatment also includes a step (iii) allowing the first DNA adapter part of the first antibody-DNA adapter conjugate to ligate to an end of the dephosphorylated DNA fragments in order to obtain a first-DNA adapter-DNA fragment product. As the skilled person understands, step (iii) requires the presence in the sample of the first antibody-DNA adapter conjugate, and optionally the first antibody, as well as the presence of the dephosphorylated DNA fragments. In a highly preferred embodiment step (iii) is performed after (1) the antibody part of the first antibody-DNA adapter conjugate or (2) the antibody, and the antibody part of the first antibody-DNA adapter conjugate to bind with its target(s) in order to provide for a first antibody-DNA adapter conjugate that is bound to the protein of interest.

The treatment comprises (i) digesting the DNA that is comprised in the nucleus or nuclei with a first restriction endonuclease to provide DNA fragments and dephosphorylating the 5'-end of the DNA fragments to provide dephosphorylated DNA fragments. The skilled person is well-aware of methods for digesting the DNA that is comprised in the nucleus and by using one or more first restriction endonucleases, for example using methods as disclosed herein. In some embodiments one first restriction endonuclease is used, but it is also contemplated that more than one type of restriction endonuclease is used, as disclosed herein elsewhere. Dephosphorylation is a common step in cloning and sequencing processes to provide for dephosphorylated DNA or DNA fragments. Using a dephosphorylating agent such as a phosphatase, e.g. recombinant shrimp alkaline phosphatase (rSAP), to remove the phosphate of the 5'-end of the digested DNA fragments reduces the occurrence of intramolecular ligation. Other suitable dephosphorylation agents can be selected by a skilled person.

For example, in this step (i) of step (b) a first restriction endonuclease and a dephosphorylating agent, e.g. a phosphatase, are provided to the one or more nuclei comprising DNA. As provided herein said first restriction endonuclease and dephosphorylating agent can be added sequentially or simultaneously. For example, a first restriction endonuclease and a dephosphorylating agent can be comprised in a suitable buffer and added to the cell nuclei. Dephosphorylation can occur almost directly after the DNA is cut by the first restriction endonuclease, allowing the DNA to be cut and fragmented and be dephosphorylated more or less at the same moment.

The digestion of the DNA causes the DNA to be cleaved or fragmented into smaller fragments of DNA (DNA fragments). The digestion also creates ends in the DNA that can be used to ligate with the DNA adapter part of the one or more first antibody-DNA adapter conjugates, in particular in case the first antibody-DNA adapter conjugate, directly, or indirectly by the use of a first antibody, are bounds to or in interaction with a protein of interest that interacts with the DNA. In this way, the DNA adapter (first DNA adapter) of the first antibody-DNA adapter conjugate can be ligated to DNA that is in close proximity of wherein the protein of interest interreacts with the DNA.

As discussed above, the treatment comprises (ii) contacting the one or more nuclei with one or more first antibody-DNA adapter conjugates, wherein a first antibody-DNA adapter conjugate (i.e. the first antibody part thereof) is directed to a protein of interest (also referred to as situation 1) and/or contacting the one or more nuclei with one or more first antibodies and one or more first antibody-DNA adapter conjugates, wherein the first antibody is directed against a protein of interest, i.e. a protein of interest suspected to interact with DNA and the first antibody-DNA adapter conjugate (i.e. the first antibody part thereof) is directed against said first antibody (also referred to as situation 2). As mentioned, this part (ii) of the treatment may be performed before, during, or after the part (i) of digesting and dephosphorylating.

It is understood that in situation 1 the first antibody part of the antibody-DNA conjugate is directed against a protein of interest, suspected to interact with DNA. In other words, the antibody part of said antibody-DNA conjugate has a certain binding affinity for, i.e. can bind to or interact with, the protein of interest (which in situation 2 is the first antibody that is directed against the protein of interest). Preferably an antibody is selected that is suitable for conjugation, as a first antibody part, with a first DNA adapter and wherein said antibody, or antibodies, is suitable for binding to a target, such as a protein of interest, preferably a target that is a protein suspected of binding DNA. DNA-binding proteins may be proteins that bind to single- or double-stranded DNA. Non-limiting examples of proteins known for binding DNA are well-known in the art and comprise for example a protein such as a histone, a histone having a post-translational modification, preferably wherein the modification is one or more selected from the group consisting of methylation, phosphorylation, acetylation, ubiquitylation, and sumoylation, a DNA polymerase, a RNA polymerase, a transcription factor, a nuclease, a high-mobility group protein, a nucleosome remodeler, a nuclear structural protein, a DNA damage repair protein, a histone modifying enzyme, a component of a chromatin complex, a chromatin structural protein, and a histone chaperone. Other examples may include protein-drug conjugates such as antibody-drug conjugates.

The first antibody-DNA adapter conjugate thus comprises a first antibody part and a first DNA adapter part. The skilled person knows how to provide for such first antibody-DNA adapter conjugate comprising a first antibody part and a first DNA adapter part, using well-known techniques available in the prior art and, for example, as described herein. The herein provided antibody parts can be conjugated to the DNA adapter part by means of method available and common in the art such as, non-covalent conjugation, such as coupling via biotin-streptavidin or covalent conjugation, using e.g. thiol-maleimide chemistry, or strain-promoted azide-alkyne cycloaddition (SPAAC) click chemistry, between azide and DBCO molecules. Other methods known and suitable for conjugation of biomolecules can also be implemented by a skilled person for conjugating the antibody to a DNA.

The first antibody part may be any type of antibody that may be suitable be used in the method of the invention as long as it may be ligated to or coupled to the first DNA adapter part that comprises a nucleic acid sequence, e.g. a DNA sequence and may be single stranded, of, preferably, double stranded. For example, the antibody may be a single-stranded antibody, a nanobody, or whole antibody (e.g. an IgG antibody). Thus, the term antibody in the context of being the first antibody part of the first antibody-DNA adapter conjugate, or in the context of the first antibody (as used in situation 2) may refer in the broadest sense to molecules with an immunoglobulin-like domain (e.g. IgG, IgM, IgA, IgD or IgE) and includes monoclonal, recombinant, polyclonal, chimeric, human, humanized, multispecific antibodies, including bispecific antibodies, and heteroconjugate antibodies; a single variable domain (e.g., VH, VHH, VL, domain antibody (dAb)), antigen binding antibody fragments, Fab, F(ab')2, Fv, disulphide linked Fv, single chain Fv, disulphide-linked scFv, diabodies, TANDABS, etc., and any modified versions of any of the foregoing.

The first DNA adapter part of the first antibody-DNA adapter conjugate comprises a nucleic acid sequence, e.g. a DNA sequence and may be single stranded, of, preferably, double stranded and is coupled to the first antibody part of the first antibody-DNA adapter conjugate. In other words, the first antibody-DNA adapter conjugate comprises a first antibody part that is conjugated to a first DNA adapter part.

As described above in one embodiment the first antibody-DNA adapter comprises one DNA adapter, for example, wherein one DNA adapter part is coupled to one antibody. In some other embodiments, a first antibody-DNA adapter conjugate comprises more than one, for example two, three, four or five, six, or more DNA adapters (also referred to as DNA adapter parts). In such preferred embodiments, the ratio antibody:DNA adapter part in the first antibody-DNA adapter conjugate is in a ratio of 1:1, 1:2, 1:3, 1:4. 1:5, 1:6 or more. In embodiments of the invention, the more than one DNA adapter part in a (single) first antibody-DNA adapter conjugate are the same; i.e. more than one identical DNA adapter in the same first antibody-DNA adapter conjugate. In some embodiments, more than one type of DNA adapter is used in the same first antibody-DNA adapter conjugate. For example, the more than one type of DNA adapter may differ in length, in sequence, or for example, in cohesiveness to its target, as disclosed herein.

Thus, in a further embodiment, the same (single) first antibody-DNA adapter conjugate comprises more than one, for example two, three, four, five, six, or more different DNA adapters (adapter parts). In such embodiment, the ratio antibody:DNA adapter (part) in the first antibody-DNA adapter conjugate can be in a ratio of 1:1, 1:2, 1:3, 1:4, 1:5 or 1:6, albeit the different DNA-adapters comprised in the single first antibody-DNA adapter may not all be identical, e.g. one or more may be different (different type). The inventors found that conjugation of multiple different DNA adapters to the same first antibody-DNA adapter conjugate potentiates the increase of chance of a successful ligation of one or more of the different DNA adapters to the genomic DNA. As will be understood by the skilled person, in embodiments wherein more than one first antibody-DNA adapter conjugates are used (e.g. in multiplex experiments directed to different protein target or using different types of antibodies), each of the different first antibody-DNA adapter conjugates may, independently comprise one or more than one DNA adapter parts, as discussed above.

With respect to the first DNA adapter part in the first antibody-DNA adapter conjugate, an end of the first DNA adapter part is cohesive or is made cohesive to an end of the dephosphorylated DNA fragments defined in step (i) as described herein elsewhere. The skilled person is well-aware to provide for such cohesive end to an end of the first DNA adapter part and understands that this is dependent on the one or more first restriction endonucleases that are employed to provide the dephosphorylated DNA fragments. It is also to be understood that the end of the first DNA adapter may already be made cohesive before the contacting of the nuclei (ii) with the first antibody-DNA adapter conjugates or may be done during or after said contacting took place.

In other words, a DNA adapter part, for example a first DNA adapter part of a first antibody-DNA adapter conjugate, comprises a short single- or double-stranded sequence or string of nucleotides that can ligate to ends of other DNA molecules. It is herein preferred that an end of the first DNA adapter part is cohesive to an end of a dephosphorylated DNA fragment as defined in step (i) of the method. In one aspect the DNA adapter is already cohesive, i.e. already comprises a cohesive end, prior to contacting with the one or more cell nuclei comprising DNA. This enables that the DNA adapter can directly ligate to the dephosphorylated DNA fragments. In another aspect the end of the DNA adapter is digested with a restriction enzyme, e.g. NdeI, to make a cohesive end.

In addition, the first DNA adapter part comprises a second restriction site for a second restriction endonuclease. As will be understood by the skilled person, in a preferred embodiment, the DNA adapter does not comprise a restriction site for the first endonuclease and that is used to fragment the DNA comprised in the nucleus.

In a preferred embodiment the first DNA adapter part comprises a first barcode sequence, wherein the first barcode sequence is positioned between the end of the first DNA adapter part that is cohesive to an end of the dephosphorylated DNA fragments defined in step (i) and the second restriction site. Barcodes are herein discussed elsewhere.

In situation 1 of step (b) (ii) of the invention, the first antibody-DNA adapter conjugate directly binds or interacts with the protein of interest and is a preferred embodiment of the invention.

In situation 2 of step (b) (ii) of the invention, the first antibody-DNA adapter conjugate is directed against the first antibody. In this situation the first antibody directly binds with the protein of interest and the first antibody part of the first antibody-DNA adapter conjugate is directed against said first antibody. Situation 2 is also a preferred embodiment of the invention. In situation 2, the first antibody may, for example, be contacted with the nuclei before or simultaneously with the first antibody-DNA adapter conjugate.

Contacting the nuclei in step (b) (ii) can be done by incubating said cell nuclei in a suitable media or buffer comprising said one or more first antibodies and one or more first antibody-DNA adapter conjugates or by adding said one or more first antibodies and one or more first antibody-DNA adapter conjugates to a media that comprises the cell nuclei.

It is understood herein that the cell nuclei comprising DNA can be contacted with at least one first antibody-DNA adapter conjugate and/or at least one first antibody. Provided herein, said cell nuclei can be contacted with 1, 2, 3, 4, 5, 10, 20, 50, 100, 1000 . . . etc. different antibody-DNA adapter conjugates and/or first antibody. It is contemplated that the number of different first antibody-DNA adapter conjugates and/or first antibody used are depending on the number of proteins of interest for an assay.

The contacting, before, during, or after step (i), with the one or more cell nuclei comprising DNA with one or more first antibody-DNA adapter conjugates, and/or with one or more first antibodies and one or more first antibody-DNA adapter conjugates is under conditions that allows (1) the antibody part of the first antibody-DNA adapter conjugate or (2) the antibody, and the antibody part of the first antibody-DNA adapter conjugate to bind with its target(s), e.g. with the protein of interest, e.g. suspected to interact with DNA comprised in the nuclei and, in the case of situation (2) binding of the first antibody-DNA adapter conjugate with the first antibody. By allowing the (1) the antibody part of the first antibody-DNA adapter conjugate or (2) the antibody, and the antibody part of the first antibody-DNA adapter conjugate to bind with its target(s) there is provided for a first antibody-DNA adapter conjugate that is bound to the protein of interest.

The first antibody-DNA adapter conjugate that is bound to the protein of interest thus comprises in situation 1 the first antibody-DNA adapter conjugate that is bound via the first antibody part of the first antibody-DNA adapter conjugate to the protein of interest. The first antibody-DNA adapter conjugate that is bound to the protein of interest thus comprises in situation 2 the first antibody-DNA adapter conjugate that is bound to the first antibody that is bound to the protein of interest.

As mentioned, the treatment also includes a step (iii) allowing the first DNA adapter part of the first antibody-DNA adapter conjugate to ligate to an end of the dephosphorylated DNA fragments in order to obtain a first-DNA adapter-DNA fragment product. As the skilled person understands, step (iii) requires the presence in the sample of the first antibody-DNA adapter conjugate, and optionally the first antibody, as well as the presence of the dephosphorylated DNA fragments. In a preferred embodiment step (iii) is performed after (1) the antibody part of the first antibody-DNA adapter conjugate or (2) the antibody, and the antibody part of the first antibody-DNA adapter conjugate to bind with its target(s) in order to provide for a first antibody-DNA adapter conjugate that is bound to the protein of interest, e.g. after allowing (1) the antibody part of the first antibody-DNA adapter conjugate or (2) the antibody, and the antibody part of the first antibody-DNA adapter conjugate to bind with its target(s) in order to provide for a first antibody-DNA adapter conjugate that is bound to the protein of interest.

The first-DNA adapter-DNA fragment thus comprises DNA from the first DNA part of the first antibody-DNA adapter conjugate coupled (ligated; via the cohesive ends) with the fragmented DNA comprised in the nuclei. It is contemplated that the first-DNA adapter-DNA fragment is also coupled or bound to the protein of interest that is bound to the DNA fragment and that in turn is bound to either the first antibody part of the first antibody-DNA adapter conjugate or to the first antibody (that, in turn is bound to the first antibody part of the first antibody-DNA adapter conjugate). It is thus contemplated that the DNA fragment is a fragment that interacts with or is bound to the protein of interest, which allows, via the first antibody-DNA adapter conjugate and/or the first antibody to bring the first DNA adapter in close proximity to the end of the DNA fragment, and allowing, for example after washing non-bound first antibody-DNA adapter conjugates away, to ligate to the end of the DNA fragment therewith identifying or tagging a DNA sequence in the DNA comprised in the nuclei to which or in close proximity to which the protein of interest was bound or was interacting with.

After performing step (b) and providing one or more first-DNA adapter-DNA fragment products, the method of the invention comprises a step (c). In step (c) the nuclei and/or cells wherein the nuclei are comprised are lysed while protein is degraded using standard techniques. In preferred embodiments, step (c) may also comprise decrosslinking, for example in case the nuclei have been permeabilized and fixed using (para)formaldehyde.

As the skilled person will understand, in step (c) the protein of interest, the first antibody and the first antibody part of the first antibody-DNA adapter conjugate will be degraded, with only the first-DNA adapter-DNA fragment product remaining intact.

Thus, step (c) comprises (i) treating the sample obtained after step (b) by degrading protein, preferably by conducting a protein degradation enzyme treatment, preferably wherein the enzyme comprises proteinase K, and/or by heat treatment, and, lysing the nuclei. Said treatments are well-known to the skilled person and include, for example those described herein elsewhere, including those detailed in the example.

In addition, as part of step (c) the sample obtained after step (b) is (ii) treated, before or after (i) of step (c) by treating the DNA in the sample with the second restriction endonuclease thereby introducing a cut at the second restriction site that is comprised in the first DNA adapter part. As will be discussed herein elsewhere, the second endonuclease introduces a cut in the first-DNA adapter-DNA fragment product that allows a second DNA adapter to ligate (in step (d)). As discussed above, the restriction site for the second restriction endonuclease is comprised in the first DNA adapter of the first antibody-DNA adapter conjugate. Again, the skilled person knows how to perform the treatments of step (c) of the method of the invention, for example as disclosed herein.

In a next step (d) of the method of the invention, the sample obtained after the treatment in step (c) incubated with a second DNA adapter, wherein an end of the second DNA adapter is cohesive, preferably wherein the cohesive end has a 5'end phosphate group, to the end created at the second restriction site of the first DNA adapter in step (c) (ii). The skill person know how to provide for such second adapter using his general knowledge as well as using the information as disclosed herein elsewhere.

The second DNA adapter comprises an RNA polymerase binding sequence and/or a DNA primer sequence (the latter of which could be used in, for example, poly-chain reaction (PCR) and sequencing instead of in vitro transcription techniques (IVT). Such RNA polymerase binding sequence and/or a DNA primer sequences are well-known to the skilled person and can be used in order to allow amplification of the DNA comprised in the first-DNA adapter-DNA fragment and/or the second DNA adapter using standard techniques such as PCR and/or linear (RNA) amplification.

The second DNA adapter preferably further comprises a second barcode sequence, preferably wherein the second barcode sequence is positioned between the RNA polymerase binding sequence and/or a DNA primer sequence and the end that is cohesive to the end created at the second restriction site of the first DNA adapter in step (c) (ii). The second barcode is further discussed herein elsewhere.

The contacting in step (d) is under conditions that allow the second DNA adapter to ligate to the end created at the second restriction site of the first DNA adapter part in step (c) (ii) in order to obtain a second DNA adapter—first DNA adapter—DNA fragment product. This thus comprises DNA from the second DNA adapter, the first DNA adapter and the DNA fragment with which the first DNA adapter ligated, as described above. Again, the skilled person very well understands how to provide for such conditions allowing the ligation and the obtaining of the second DNA adapter-first DNA adapter—DNA fragment product.

In a next step (e) of the method of the invention, the second DNA adapter—first DNA adapter—DNA fragment product is amplified and sequenced in order to obtain sequence information of the obtained amplified product. Such sequence information can, for example by applying bioinformatic techniques, be used to determine, for example, the genomic position where the protein of interest has interacted with the DNA, and to what extent binding of the protein of interest took place. Again, any suitable DNA amplification method and/or sequencing method can be used in the method of the invention, for example those described herein elsewhere, including the examples.

In embodiments of the invention the one or more nuclei of step (a) disclosed above:
- is one cell nucleus;
- comprises more than 10, 20, 100 or 1000 cell nuclei;
- is from an animal, preferably from a mammal, more preferably from a human;
- is obtained from a single type of organism, or a single organism, preferably a single human;
- is obtained from a diseased tissue;
- is comprised in a cell; and/or
- is from one type of cell or from different types of cells.

The method of the invention is not in particular limited with respect to the number of (permeabilized and fixed) cell nuclei and/or the organism from which such cell nuclei are obtained. The skilled person will understand, based on the disclosure herein, how to select the appropriate number of nuclei and the type of organism or cells from which such nuclei are obtained, for example, in view of the envisaged use of the method of the invention.

For example, in some embodiments of the method of the invention the method is performed on a single cell nucleus. In other embodiments more than one nucleus, i.e. nuclei are provided in step (a) of the method of the invention. Non-limiting examples include that more than 10, 20, 100 or 1000 cell nuclei, for example .g. 10's, 100's, 1000's, 10's of thousands, 100's of thousands, millions, or more, are provided in step (a) of the method of the invention. The inventors surprisingly found that the method in accordance with the invention was able to detect multiple parameters, e.g. multiple post-transcriptional modifications, at single cell resolution.

In some embodiments, the more than one nuclei are from the same, single type of organism (e.g. from more than one human subject), from the same, single, organism (e.g. from one and the same human subject), from the same type of tissue (e.g. from colon), for example a healthy or diseased tissue, and/or any combination thereof.

In other embodiments a mixture of cell nuclei is provided in step (a) of the method. For example, nuclei obtained from different types of organisms may be combined (e.g. from a rodent and from a primate), or nuclei obtained from different organisms of the same type may be combined, or nuclei obtained from different types of tissue may be combined (e.g. colon and lung). Likewise, the nuclei may be from the same cell type or from different cell types. For example, in some embodiments, nuclei are obtained from a tumor comprising different types of cell, for example different types of cancerous cells as well as healthy cells. Examples of preferred cell types comprising the nuclei for use in the method of the invention include but are not limited to epithelial cells, endothelial cells, skin cells, lung cells, colon cells, brain cells, bone cells, blood cells, stem cells, cells from the germ layer, cancer cells, cell lines, primary cells, cells from an organoid, cells from a spheroid, and the like.

The one or more nuclei may be from different types of organisms, not limited to plants, yeast, animals, mammalians, rodents, such as mice and rat, primates, and, in particular humans. Preferably the nuclei is from a cell from an animal, preferably from a rodent or mammal, preferably a human.

The one or more nuclei may be from healthy tissue or cells and/or from diseased tissue or cells. For example, cells may be obtained from healthy tissue or cells and from diseased tissue of cells, for example from the same type of organism or from the same organism (e.g. the same human subject or patient).

The skilled person is well aware of methods for obtaining one or more cell nuclei from an organism, for example by methods involving those that are commonly used for obtaining samples, such as taking a biopsy, e.g. from a tissue of interest, or obtaining a bodily fluid sample, e.g. blood, saliva etc. The skilled person is generally aware of suitable methods for obtaining samples from organisms. In it understood herein that a sample can be obtained from one or more organisms, for example one or more mice, one or more humans. In a preferred embodiment, the one or more cell nuclei are obtained from a single organism, more preferably even, from a single human subject.

It is also preferred herein that the one or more cell the one or more nuclei in the provided sample of step (a) are nuclei that are comprised in a cell. Alternatively, the one or more nuclei may be isolated from such cell. In those embodiments wherein the nuclei is present in a cell, the cell comprising the nuclei is, together with the nuclei, permeabilized and fixed in order to provide for a permeabilized and fixed cell comprising a permeabilized and fixed cell nucleus.

As already described above, the one or more nuclei can be selected and obtained from different, multiple, types of cells, e.g. obtained from a (diseased) tissue, a cell culture, an organoid, a spheroid, a cell line. In the method of the invention the same nuclei or a mixture of nuclei from different types of organisms, organisms, tissues, cell types, and so on may be used.

As will be understood, in some embodiments, all or only part of the nuclei provided in step (a) of the method of the invention are subjected to the subsequent steps of the method of the invention, and/or subjected to the sequencing in step (e). In other words, in some embodiments not for all nuclei the sequence of DNA that would be amplified using the method of the invention is determined.

In some embodiments there is provided for a method wherein the first restriction endonuclease:

- creates a blunt end or creates an end with an overhang;
- recognizes a recognition site that is 4-8 base pair in length, preferably 4 base pair in length, preferably the first restriction endonuclease is selected from the group consisting of MseI, MboI, DpnII, and NlaIII; and/or
- is a restriction endonuclease that on average cuts the DNA every 100-10000 base pairs.

The first restriction endonuclease, sometimes also referred to as restriction enzyme, that is provided in step (i) of step (b) in the method is provided to the sample of step (a) comprising the one or more cell nuclei, in order to cut and/or fragment DNA that is comprised in the said one or more cell nuclei. The skilled person is well aware of restriction endonuclease, and that are suitable for use in the method of the current invention, and how to use these in the context of the current invention.

In general, restriction endonucleases are enzymes that recognize a specific DNA sequence, called a restriction site, and cleave the DNA within or adjacent to that site. Restriction endonucleases may thus be used to fragment DNA by cleaving the DNA at specific target sequences in the DNA. Naturally occurring restriction endonucleases are commonly classified into different groups, depending on factors such a target sequence and position of DNA cleavage relative to the target sequence, and are commercially available from various sources.

Commonly used artificial restriction enzymes that are contemplated within the context of the invention include fusion proteins comprising a natural or engineered DNA-binding domain and a nuclease domain (such as those derived from the restriction enzyme FokI), zinc finger nucleases, and CRISPR/CAS enzymes such as Cas9.

Although the method of the invention is not in particular limited to a specific type of restriction endonuclease, is some preferred embodiment, the first restriction endonuclease recognizes a recognition site in the DNA (that is comprised in the nuclei) that is 4-8 base pair in length, such as 4, 5, 6, 7 or 8 base pairs in length. Preferably, the recognition site of the first restriction endonuclease is 4 base pairs in length. Subsequently to recognizing the specific sequence of nucleotides, the restriction endonuclease can produce a cut in the DNA strand. Often, and in a preferred embodiment, the cut that is introduced by the restriction endonuclease in the DNA that is comprised is a double-stranded cut, i.e. both strands of the double-stranded (ds) DNA is cut by the first restriction endonuclease.

In some embodiments it is preferred that the first restriction endonuclease used in the method on average cuts the DNA that is comprised in the nuclei every 100-10.000 base pairs, preferably every 100-500 base pairs. In other words, on average, the first restriction endonuclease selected for use in the method recognizes a recognition site every 100-10.000 base pairs in the DNA comprised in the nuclei. On average, each DNA fragment that is produced due to the cleaving of the first restriction enzyme of the DNA comprises on average about 100-10.000 base pairs. The skilled person understands how to select for restriction endonuclease that is are suitable for use as the first restriction endonuclease in the method of the invention. For example, a restriction endonuclease that cuts, on average, every 100-10.000 base pairs can be selected by determining, for example by using publicly available DNA sequence information, the frequency of the presence of the restriction site for a given restriction endonuclease. It will be understood by a skilled person that the restriction endonuclease selected, may, for example, depend on the type of organism from which the nuclei used in the method are obtained. Obviously it may also depend on the protein of interest since these sometimes bind in region with certain sequence bias.

In some embodiments, the first restriction endonuclease creates a blunt end, i.e. a non-cohesive end, however, in a preferred embodiment the first restriction endonuclease creates an end with an overhang (sometimes also referred to as a sticky end). In case the first restriction endonuclease creates a blunt end, the first antibody-DNA adapter conjugate may also be provided with a blunt end, thus allowing it to ligate to the blunt ends introduced by the first restriction endonuclease in the DNA that is comprised in the nuclei. In an alternative embodiment, the blunt ends created by the first restriction endonuclease may be further modified in order to create an overhang.

The overhang, for example the overhang that is introduced by the first restriction endonuclease, in the DNA that is comprised in the nuclei may be of any length, for example the overhang (for example 3' overhang) may be one nucleotide or more, for example, two, three or four nucleotides. As is explained herein, in a preferred embodiment, the end that is created by the first restriction endonuclease is an end that is cohesive to the end that is present in or provided to the first antibody-DNA adapter conjugate that is used in the method of the invention.

Although the invention is not in particular limited to a specific first restriction endonuclease, in some preferred embodiments the first restriction endonuclease is selected from the group consisting of MseI, MboI, DpnII, and NlaIII. The restriction endonuclease are commercially available from different sources and the skilled person is well aware on how to use these in the context of the invention. The skilled person is familiar with said restriction enzymes and methods for treating cell nuclei comprising DNA with said restriction enzymes.

Finally, it is contemplated that in embodiments more than one type of first restriction endonuclease is used in the method. For example, in some embodiments, two, three or more different restriction endonuclease are applied in the method of the invention, preferably simultaneously or sequentially in the same experiment. As is understood by the skilled person, it is also contemplated that more than one type of first antibody-DNA adapter conjugates are used in the method of the invention, for example wherein the antibody in the different types of first-antibody-DNA adapters are directed to different proteins of interest and/or modifications of interest, and/or wherein the different first antibody-DNA adapter conjugates comprise different ends that are cohesive to different ends that are introduced by one or more different restriction endonucleases in the DNA comprised in the nuclei. For example, is one example a first restriction endonuclease A may be used, and two (or more) different first antibody-DNA adapter conjugates C and D are used (C may for example comprise another antibody than D), wherein, for example both antibody-DNA adapter conjugates C and D are cohesive to the end that is created by the first restriction endonuclease A. In another example, two different first restriction endonucleases A and B and two (or more) different first antibody-DNA adapter conjugates C and D are used, wherein, for example first antibody-DNA adapter conjugate C is cohesive to first restriction endonuclease A, and wherein first antibody-DNA adapter conjugate D is cohesive to first restriction endonuclease B.

In embodiments of the invention there is provided for the method wherein in situation (1), i.e. in situation (1) of step (ii) of step (b) of the method of the invention, the antibody part of the antibody-DNA adapter conjugate and in situation (2)), i.e. in situation (2) of step (ii) of step (b) of the method of the invention, the antibody is directed against a protein that is known to bind to DNA or that is suspected to bind to DNA. The antibody part of the first antibody-DNA adapter conjugate (situation (1) or the antibody (situation 2) may in principal be directed to any protein that is or can be expressed in a cell. In preferred embodiments the antibody part of the first antibody-DNA adapter conjugate (situation 1) or the antibody (situation 2) is directed to a protein that is known to interact with DNA, for example that is known to bind to DNA and/or is directed to a protein that is suspected to interact with DNA. As the skilled person understands, it is not necessary that the protein to which the antibody part of the first antibody-DNA adapter conjugate (situation 1) or the antibody (situation 2) is directed is known to bind to DNA under the conditions of the experiment. With the method of the invention it is also possible to establish whether such interaction occurs, to what extent, and where on the DNA. The skilled person also understand that the protein may be a protein that is naturally expressed in the cells from which the nuclei are obtained or may be a protein that is non-natural to these cells. The protein may also be a non-natural protein, e.g. a fusion-protein, for example designed with the purpose of interacting with DNA.

The term “protein suspected to bind to DNA” is thus directed to any proteinaceous molecule, including proteins, peptides, fusion proteins, and the like. The protein suspected to bind may interact directly with the DNA or may do so indirectly, for example, by binding to, or interacting with a further protein that is directly bound to the DNA, or, for example, by being part of a DNA-binding complex.

The antibody part of the first antibody-DNA adapter conjugate (situation (1)) or the antibody (situation 2) is preferably specific to the protein suspected to bind but may also be an antibody that may recognize more than one protein (or epitope therein).

In some embodiments, the protein is selected from the group consisting of protein a histone, a histone having a post-translational histone modification, preferably wherein the modification is one or more selected from the group consisting of methylation, phosphorylation, acetylation, ubiquitylation, and sumoylation, a DNA polymerase, a RNA polymerase, a transcription factor, a nuclease, a high-mobility group protein, a nucleosome remodeler, a nuclear structural protein, a DNA damage repair protein, a histone modifying enzyme, a component of a chromatin complex, a chromatin structural protein, and a histone chaperone.

In some embodiments, the antibody part of the first antibody-DNA adapter conjugate (situation (1)) or the antibody (situation 2) binds to, or is specific for, a protein that comprises a post-translational modification, such as a protein that comprises a methylation, phosphorylation, acetylation, ubiquitylation, and sumoylation. Preferably, in these embodiments, the antibody part of the first antibody-DNA adapter conjugate (situation (1)) or the antibody (situation 2) is specific for the protein having the post-translational modification, and, for example, does not, or to a lesser extent, recognize and bind to the protein that is devoid of said post-translational modification, and/or that comprises a post-translation modification that is different (e.g. that is modified by another group e.g. by methylation instead of acetylation, or wherein the modification by acetylation is on another location (amino acid) in the histone protein, or wherein the protein includes additional modifications, or less modification). For example, antibodies that discriminate between unmodified histone proteins, and different post-translationally modified histones (e.g. by acetylation or methylation at specific locations in the histone protein) have extensively been described and are commercially available from various sources (e.g. Abcam).

Indeed histones, as well as histone modifications, and their role in the interaction with DNA, in health and disease are well-known to the skilled person. DNA within cells is packaged as chromatin, a dynamic structure composed of nucleosomes as the fundamental building blocks. Histones are the central component of the nucleosomal subunit, in humans forming an octamer containing four core histone proteins (H3, H4, H2A, H2B) around which is wrapped a 147-base-pair segment of DNA. Each histone proteins possesses a side chain, or tail, that is subject to covalent post-translational modifications (PTMs) and that regulate chromatin state. Some PTMs alter the charge density, impacting chromatin organization and underlying transcriptional processes, but they can also serve as recognition signals for specific binding proteins that, when bound, may then signal for alterations in chromatin structure or function. (see, for example, Audia et al. (2016) Cold Spring Harb Perspect Biol 1; 8(4)).

Therefore, in some embodiments the protein of interest is a histone and/or a histone having a histone modification, preferably wherein the modification is one or more selected from the group consisting of methylation, phosphorylation, acetylation, ubiquitylation, and sumoylation. In these embodiments the antibody part of the first antibody-DNA adapter conjugate (situation (1)) or the antibody (situation 2)

In other embodiments the protein of interest is a DNA polymerase, a RNA polymerase, a transcription factor, a nuclease, a high-mobility group protein (High-Mobility Group or HMG is a group of chromosomal proteins that are involved in the regulation of DNA-dependent processes such as transcription, replication, recombination, and DNA repair.), a nucleosome remodeler (see, for example, Becker et al (2013) Cold Spring Harb Perspect Biol. 5(9): a017905), a nuclear structural protein, a DNA damage repair protein, a histone modifying enzyme, a component of a chromatin complex, a chromatin structural protein, and/or a histone chaperone (a structurally and functionally diverse family of histone-binding proteins, involved in nucleosome assembly (see, for example, Burgess et al (2013) Nat Struct Mol Biol. 20(1): 14-22.) These types of proteins are known to the skilled person, as well as their potential role and function in interaction with DNA.

As the skilled person understands, in situation (2) of step (ii) of step (b) of the method of the invention the first antibody part of the first antibody-DNA adapter conjugate is directed against the first antibody that is directed to the protein of interest.

In embodiments of the invention there is provided for the method wherein the first DNA adapter part of the first antibody-DNA adapter conjugate:

- has a length of between 50 and 150 base pairs;
- comprises the first barcode sequence, wherein, preferably, the first barcode sequence is uniquely identifying the antibody part of the antibody-DNA adapter conjugate; and/or
- is made cohesive to an end of the dephosphorylated DNA fragments created in step (b)(i) before or after the antibody part of the first antibody-DNA adapter conjugate has been allowed to bind to its target.

As the skilled person understand, the first DNA adapter part of the first antibody-DNA adapter conjugate is comprised of nucleotides, such as A, T, C, and G, forming a nucleic acid, e.g. DNA, sequence. The first DNA adapter (or any other DNA adapter disclosed herein) may be single stranded but is preferably doubled stranded. The DNA adapter is preferably linear, i.e. having at least one end. Although not in particular limited by the current invention, in a preferred embodiment the first DNA adapter part of the first antibody-DNA adapter conjugate has a length of more than 10 base pairs, preferably more than 20 base pairs. Preferably the length is less than 1000 base pairs, for example the first DNA adapter part of the first antibody-DNA adapter conjugate comprises a length of between 50 and 150 base pairs, for example about 80-85 base pairs.

In some embodiment first DNA adapter part of the first antibody-DNA adapter conjugate comprises a first barcode sequence, preferably wherein the first barcode sequence is uniquely identifying the antibody part of the antibody-DNA adapter conjugate sample (and, in case of in situation (2) of step (ii) of step (b) of the method of the invention, therewith also uniquely identifying the antibody that is directed to the protein of interest). The use of barcode sequences is well-known to the skilled person, and any suitable barcode sequence can be used within the context of the current invention. The barcode sequence may be of any length, for example 3, 4, 5, 6, 7, 8, 9 or more base pairs in length. The first DNA adapter part of the first antibody-DNA adapter conjugate may comprise more than one, for example one, two or more barcode sequences.

In some embodiments, the first DNA adapter part of the first antibody-DNA adapter conjugate is made cohesive to an end of the dephosphorylated DNA fragments created in step (b)(i) before or after the antibody part of the first antibody-DNA adapter conjugate has been allowed to bind to its target. The skilled person will understand that the first DNA adapter part of the first antibody-DNA adapter conjugate may already be cohesive to an end of the dephosphorylated DNA fragments created in step (b)(i) when contacted with the nuclei, but may also be made cohesive before during or after the DNA comprised in the nuclei is digested with the first restriction endonuclease. For example, is some embodiments, the first DNA adapter part of the first antibody-DNA adapter conjugate is made cohesive by using NdeI or BglII as restriction endonuclease. Other suitable restriction enzymes can be selected and used by a skilled person for creating a cohesive end in a DNA adapter.

In a preferred embodiment, the first DNA adapter part of the first antibody-DNA adapter conjugate

- has a length of between 50 and 150 base pairs;
- comprises the first barcode sequence, wherein, preferably, the first barcode sequence is uniquely identifying the antibody part of the antibody-DNA adapter conjugate; and
- is made cohesive to an end of the dephosphorylated DNA fragments created in step (b)(i) before or after the antibody part of the first antibody-DNA adapter conjugate has been allowed to bind to its target.

In embodiments of the invention there is provided for the method wherein the condition allowing the first DNA adapter part to ligate to an end of a dephosphorylated DNA fragment comprises the use of a DNA ligase. In some embodiments, the dephosphorylated DNA fragment may first be re-phosphorylated, for example using techniques known to the skilled person. In some embodiments, this is done, for example, by incubation with a kinase, such as a T4 kinase, followed by ligase, for example after sample pooling and prior to in vitro transcription.

As explained herein, the 5'-end of the DNA fragments that are obtained by treatment with the (one or more different) first restriction endonuclease(s) are treated to remove any 5'-end phosphate groups (i.e. dephosphorylated) in order to reduce re- or self-ligation. The skilled person is well-aware of methods to dephosphorylate the 5'-end, for example using commercially available kits or enzymes such as phosphates like calf intestinal alkaline phosphatase, shrimp alkaline phosphatase or Antarctic phosphatase (New England BioLabs).

In order to allow the first DNA adapter part to ligate to the end of a dephosphorylated DNA fragment a DNA ligase may be used. Ligation is the formation of covalent phosphodiester bonds between the 3' and 5' ends of the first DNA adapter part and the dephosphorylated DNA fragment. The skilled person is well-aware of ligase that may suitably be used in this step of the method of the invention. Suitable DNA ligases are well-known in the art; one non-limiting example of a suitable DNA ligase is T4 DNA ligase.

In embodiments there is provided for the method of the invention wherein the treating of the sample in step (c) comprises treating the sample with one or more proteases, preferably wherein the protease is proteinase K, and/or wherein degrading protein comprises heat treatment, preferably wherein the heat treatments is at a temperature of between 50-70 degrees Celsius.

For example, in some embodiments the treatment with the proteinase to digest the proteins is performed at a temperature between 50 and 60 degrees Celsius, for example at a temperature of about 56 degrees Celsius. Then, in preferred embodiments, the crosslinks that are present in the permeabilized and fixated cell nucleus (for example as achieved by formaldehyde treatment or through a different crosslinking reaction) are reversed by heating the sample for an extended period of time at a temperature above 60 degrees, for example at a temperature around 65 degrees Celsius. This also lyses the cells, or nuclei, if present.

Proteases are well-known in the art and are commonly used for catalyzing the breaking down of proteins by hydrolyzing peptide bonds in said peptides. In step (c) of the method the sample is treated, preferably by providing a protein degrading enzyme, more preferably a protease, to said sample. Suitable proteases for degrading protein are known in the art and can be utilized for use in the method of the invention by the skilled person. However, in one preferred aspect the protease used in the method according to the invention is proteinase K, a commonly used broad-spectrum serine protease. One non-limiting example of degrading a protein in step (c) of the method of the invention comprises the degradation by a proteinase at a temperature of about 56 degrees. This also lyses the nuclei. In one aspect, the method in accordance with the invention provides for a method wherein the treating of step (c) comprises treating with one or more proteases, preferably wherein the protease is proteinase K.

Alternatively, or additionally, the treating of step (c) comprises that the proteins are degraded under heat treatment, for example for a period of time at a temperature between 50-70 degrees Celsius, preferably at about 65 degrees Celsius. This treatment also reverses any cross-links between, for example, proteins, that may be present in the permeabilized and fixed nuclei (and cells if present).

It is understood that, during step (c) of the method of the invention the antibody or the antibody part of the first antibody-DNA adapter conjugate also becomes degraded. Subsequently, the herein provided DNA adapter-DNA fragment becomes detached from said antibody.

In embodiments there is provided for the method of the invention wherein the second restriction endonuclease:

- creates a blunt end or creates an end with an overhang;
- recognizes a recognition site that is at least 4-8 base pair in length, preferably 6-8 base pair in length, even more preferably 8 base pairs in length or more;
- is selected from the group consisting of NotI and SfiI;
- is a restriction endonuclease that on average cuts the DNA every 20000-2000000 base pairs; and/or
- creates an end that is different from the end that is created by the first restriction endonuclease.

The second restriction endonuclease, sometimes also referred to as restriction enzyme, that is provided in step (ii) of step (c) in the method is used to cut the second restriction site that is comprised in the first DNA adapter part of the first antibody-DNA adapter conjugate that has been brought into contact with the DNA comprised in the nuclei in step (b). The cut that is introduced by the second restriction endonuclease is used in the subsequent ligation with the second (linear) DNA adapter in step (d) of the method of the invention in order to provide for the second DNA adapter—first DNA adapter—DNA fragment product of step (d). The skilled person is well aware of restriction endonuclease, and that are suitable for use in the method of the current invention, and how to use these in the context of the current invention. In preferred embodiments of the method the second restriction endonuclease is not identical (or the same) as the first restriction endonuclease. In preferred embodiments of the method, the restriction site recognized by the second restriction endonuclease is different from the restriction site recognized by the first restriction endonuclease. In another preferred embodiment of the method, the first-DNA-adapter-DNA fragment product comprises no more than one recognition site for the second restriction endonuclease. In other preferred embodiments, the second restrictions endonuclease only introduces a cut in the first DNA adapter part of the first-DNA-adapter-DNA fragment.

Although the method of the invention is not in particular limited to a specific type of restriction endonuclease, in some preferred embodiment, the second restriction endonuclease recognizes a recognition site that is 4-8 base pair in length, such as 4, 5, 6, 7 or 8 base pairs in length. Preferably, the recognition site of the first restriction endonuclease is 6-8 base pairs in length, even more 8 base pairs in length or more. Subsequently to recognizing the specific sequence of nucleotides, the restriction endonuclease can produce a cut in the DNA strand. Often, and in a preferred embodiment, the cut that is introduced by the second restriction endonuclease is a double-stranded cut, i.e. both strands of the double-stranded (ds) DNA are cut by the second restriction endonuclease.

In some embodiments, it is preferred that the second restriction endonuclease used in the method on average cuts the DNA that is comprised in the nuclei every 20000-2000000 base pairs, preferably every 20000-100000 base pairs, for example every 40000-80000 base pairs. In other words, on average, the second restriction endonuclease selected for use in the method recognizes a recognition site every 20000-2000000 base pairs. The skilled person understands how to select for restriction endonuclease that is suitable for use as the second restriction endonuclease in the method of the invention. It will be understood by a skilled person that the second restriction endonuclease selected, may, for example, depend on the type of organism from which the nuclei used in the method are obtained, or based on the type of first restriction endonuclease that is used in the method.

In some embodiments, the second restriction endonuclease creates a blunt end, i.e. a non-cohesive end, however, in a preferred embodiment the second restriction endonuclease creates an end with an overhang (sometimes also referred to as a sticky end). In case the second restriction endonuclease creates a blunt end, the second DNA adapter provided in the subsequent steps of the method of the invention may also be provided with a blunt end, thus allowing it to ligate to the blunt ends introduced by the second restriction endonuclease. In an alternative embodiment, the blunt ends created by the second restriction endonuclease may be further modified in order to create an overhang.

The overhang, for example the overhang that is introduced by the second restriction endonuclease, may be of any length, for example the overhang (for example 3' overhang) may be one nucleotide or more, for example, two, three or four nucleotides, or more. As is explained herein, in a preferred embodiment, the end that is created by the second restriction endonuclease is an end that is cohesive to the end that is present in or provided to the second DNA adapter that is used in the method of the invention.

Although the invention is not in particular limited to a specific second restriction endonuclease, in some preferred embodiments the first restriction endonuclease is selected from the group consisting of NotI and SfiI. These restriction endonucleases are commercially available from different sources and the skilled person is well aware on how to use these in the context of the invention. The skilled person is familiar with said restriction enzymes and methods for treating DNA with said restriction enzymes.

Finally, it is contemplated that in some embodiments more than one type of second restriction endonuclease is used in the method. For example, in some embodiments, two, three or more different second restriction endonuclease are applied in the method of the invention, preferably simultaneously or sequentially in the same experiment. For example, more than one second restriction endonucleases may be use in method in those embodiments wherein more than one different type of first antibody-DNA adapter conjugates are employed, and for example each comprising a different second restriction site. Therefore, in some embodiments more than one type of first antibody-DNA adapter conjugates are employed, and wherein each different type of the first antibody-DNA adapter conjugate comprises the same second restriction site or comprises a restriction site that is recognized by the same second restriction endonucleases. In other embodiments, more than one type of first anti-body-DNA adapter conjugates are employed, and wherein the different types of the first anti-body-DNA adapter conjugate comprises different second restriction sites or comprises a restriction site that is recognized by a different second restriction endonucleases. For example, as is understood by the skilled person, it is contemplated that more than one type of first antibody-DNA adapter conjugates are used in the method of the invention, for example wherein the antibody in the different types of first-antibody-DNA adapters are directed to different proteins of interest and/or modifications of interest.

In embodiments of the invention, there is provided for a method wherein the second DNA adapter:

- is linear and preferably has a length of between 50 and 100 base pairs;
- comprises an RNA polymerase binding sequence selected from a T7-RNA polymerase binding sequence and a T3-RNA polymerase binding sequence;
- comprises DNA primer sequences (which, for example, allow amplification of the DNA using primers and PCR, followed by sequencing)
- comprises the second barcode sequence wherein the second barcode sequence is uniquely identifying the sample; and/or
- comprises one or more further adapter sequences, preferably selected from P5 adapter sequences (Illumina), P7 adapter sequences (Illumina).

The skilled person understands that the invention is not limited to any particular second DNA adapter as disclosed herein. However, in preferred embodiments, the second DNA adapter is cohesive to the end created at the second restriction site of the first DNA adapter in step (c) (ii). In further preferred embodiments the second DNA adapter comprises, next to an RNA polymerase binding sequence and/or a DNA primer sequence, as second barcode sequence. In embodiments of the method of the invention, the second barcode sequence is positioned between the RNA polymerase binding sequence and/or DNA primer sequence and the end that is cohesive to the end created at the second restriction site of the first DNA adapter.

As the skilled person understands, the second DNA adapter is preferably linear. In preferred embodiments the second DNA adapter is double stranded. In some embodiments the second DNA adapter is single stranded. Although the length of the (linear) second DNA adapter is not in any particular way limited, preferably the second DNA adapter has a length of between 20 and 200 base pairs, preferably 50 and 100 base pairs, for example about 70-75 base pairs.

In embodiments of the invention, the second DNA adapter comprises an RNA polymerase binding sequence selected from a T7-RNA polymerase binding sequence and a T3-RNA polymerase binding sequence. Such T7-RNA polymerase binding sequence and a T3-RNA polymerase binding sequence are well-known to the skilled person. T7 RNA polymerase initiates RNA synthesis after binding to a specific promoter DNA sequence (or T7-RNA polymerase binding sequence) and opening the DNA duplex. For example, The T7 promoter may be a sequence of DNA that is 18 base pairs long up to transcription start site at +1 (5'-TAATACGACTCACTATAG-3') and that is recognized by T7 RNA polymerase. A T3 promoter sequence is 5' AATTAACCCTCACTAAAG 3'. T3 RNA polymerase starts transcription at the underlined G in the promoter sequence. The polymerase then transcribes using the opposite strand as a template from 5'→3'. T7-RNA polymerase binding sequence (e.g. promoter sequences), T3-RNA polymerase binding sequence (e.g. promoter sequences) and method for using these are well known to the skilled person.

In further preferred embodiments, the second DNA adapter comprises the second barcode sequence wherein the second barcode sequence is uniquely identifying the sample. The use of barcode sequences is well-known to the skilled person, and any suitable barcode sequence can be used within the context of the current invention. The barcode sequence may be of any length, for example 3, 4, 5, 6, 7, 8, 9 or more base pairs in length. The second DNA adapter may comprise more than one barcode, for example one, two or more barcode sequences.

In further preferred embodiments, the DNA adapter may comprise additional adapter sequences such as from P5 adapter sequences (Illumina) and/or P7 adapter sequences (Illumina). Such adapters include platform-specific sequences for fragment recognition by the sequencer: for example, P5 and P7 adapter sequences enable library fragments to bind to the flow cells of Illumina platforms (for example during step (e) of the method of the invention.

In further embodiments, the second DNA adapter may further comprise UMI sequences (unique molecular identifiers) for making quantitative measurements, for example 2×3 bp, i.e. 6 base pairs in total. UMIs are well-known to the skilled person and are generally referred to as complex indices added to sequencing libraries before any PCR amplification steps, enabling the accurate bioinformatic identification of PCR duplicates. UMIs are valuable tools for quantitative sequencing applications and are frequently used in technologies such as RNA-Seq and ChIP-Seq. UMIs may alleviate PCR duplication problems by adding unique molecular tags to the sequencing library molecules before amplification.

In further embodiments, the second DNA adapter may further comprise a forked overhang on the end that is not ligating to the end created at the second restriction endonuclease site of the first DNA adapter part. This is to prevent the second DNA adapter to ligate to itself (from the 5' end). Such forked overhang may, for example, be provided by including one or more nucleotides at the end in each strand, and wherein the nucleotides in each strand are no longer complementary. For example, a forked overhang can be provided at the end and that comprises 6 bp that are not complementary between the strands.

In embodiments of the invention there is provided for a method wherein the condition allowing the second DNA adapter to ligate to the end created at the second restriction site of the first DNA adapter in step (d) comprises the use of a DNA ligase.

As explained herein elsewhere with respect to the ligation of the first DNA adapter part of the first antibody-DNA adapter conjugate with the end of the DNA fragments obtained in step (b), also with respect to the ligation of the second DNA adapter, ligation thereof with the end created at the second restriction site of the first DNA adapter part is preferably performed using a DNA ligase. The skilled person is well-aware of ligases that may suitably be used in this step of the method of the invention. Suitable DNA ligases are well-known in the art; one non-limiting example of a suitable DNA ligase is T4 DNA ligase.

As already broadly described herein, in embodiments of the invention there is provided for a method wherein:

- more than one first restriction endonuclease is used;
- more than one first antibody-DNA adapter conjugate is used, wherein either the antibody, or the protein against which the antibody is directed, the first DNA adapter part, the first barcode sequence, or any combination thereof may be the same or different;
- more than one second restriction endonuclease is used; and/or
- more than one second DNA adapter is used, wherein the end of the second DNA adapter that is cohesive to the end created at the second restriction site of the first DNA adapter, the second barcode, the RNA polymerase binding sequence, the DNA primer sequence or the one or more further adapter sequences, or any combination thereof may be the same or different.

As is understood by the skilled person, one of the advantages of the current method is that the method is robust yet reproducible under a wide variety of experimental conditions and may thus be used for a broad range of purposes. It is also understood by the skilled person that the different variations, embodiments and preferences described herein for different (individual) aspects can, within the context of the current invention, be combined with such different aspects, variations, embodiments and preferences for other individual aspects described herein. Such combinations are at least implicit from the context of the current disclosure. For example, is some embodiments, the method of the invention allows for the use of nuclei obtained from a single type of cells, or from different types of cells. In some embodiments, the nuclei are obtained from cells that have been synchronized, in other embodiments synchronization of the cells (growth phase) is not required. In some example the cells from which the nuclei are obtained have been treated with a drug in order to understand its effect on the cell. In other embodiments, the cell has been genetically modified, for example to study the effect of the genetic modification. In some embodiments, the nuclei in the sample are comprised in a cell, in other embodiments, the nuclei have been isolated from the cell, prior to providing the sample. In some embodiments one type of first restriction endonuclease is used, in some embodiments a combination of different first restriction endonucleases are used. In some embodiments, one type of first antibody-DNA adapter conjugate is used, is other embodiments, more than one type of first antibody-DNA adapter conjugates are used. In some embodiments, the antibody part of the first antibody-DNA adapter conjugate is directed to a protein of interest, in other embodiments, the antibody part of the first antibody-DNA adapter conjugate is directed to different proteins of interest. In some embodiments the first antibody part of the first antibody-DNA adapter conjugate is directed to a post-translational modification on a protein of interest, for example, directed to a histone modification, including those described herein. In such embodiment the antibody part of the first antibody-DNA adapter conjugate makes a distinction between such protein of interest having such modification versus the same protein of interest not having the same modification. In embodiments wherein more than one first antibody-DNA adapter conjugates are employed, the antibody parts of the different types first antibody-DNA adapter conjugates may be directed to the same protein of interest, may be directed to different epitopes in the same protein, may be directed to different post-translational modifications of the same protein (e.g. a first antibody recognizing a first modification, and a second antibody recognizing a second modification, in the same protein), and/or may be directed to different proteins of interest. In some embodiment the first antibody-DNA adapter conjugates comprise the same second restriction site, in some embodiment the first antibody-DNA adapter conjugates may comprise different second restriction sites. In some embodiments, first antibody-DNA adapter conjugates are used that differ with respect to the antibody part, and/or that differ with respect to the DNA adapter part, or both. In some embodiments, the first antibody-DNA adapter conjugates comprises a barcode. In some embodiments different first antibody-DNA adapter conjugates comprise different barcodes. In some embodiments, and wherein one or more first antibodies are used and one or more first antibody-DNA adapter conjugates are used (and that can bind to the first antibodies), different first antibodies may, like is explained for the antibody part of the first antibody-DNA adapter conjugates, likewise be directed to the same or to different proteins of interest, including different post-translational modifications on such proteins. In some embodiments, one type of second restriction endonuclease is used, in other embodiments more than one type of second restriction endonuclease are used, as already explained herein. In some embodiments one type of second DNA adapter is used. In some embodiments, more than one second DNA adapter is used. In some embodiments, wherein more than one second DNA adapter is used, the end of the second DNA adapter that is cohesive to the end created at the second restriction site of the first DNA adapter, the second barcode, the RNA polymerase binding sequence, the DNA primer sequence, or the one or more further adapter sequences, or any combination thereof may be the same or different. The first antibody-DNA adapter conjugates may comprise sequences that allows to encode/identify the protein or modification of interest that is targeted with the first antibody-DNA adapter conjugate (either directly, of indirectly in case use is made of a first antibody that is directed to the protein of interest). The second DNA adapter may comprise sequences that allows to encode/identify the specific sample/cell, for example in case of pooling and subsequent sequencing. At the same time the skilled person understands that each of the choices with respect to the embodiments described herein, for example, those described above, may be combined in the method of the invention.

In some embodiments of the method of the invention, there is provided for the method wherein amplification of the second-DNA adapter—first-DNA adapter—DNA fragment product is by linear amplification. Although the invention is not in particular limited by any particular method of amplifying the obtained second-DNA adapter—first-DNA adapter—DNA fragment, in some embodiments linear amplification is preferred. Amplification of DNA by linear amplification is a well-known technique for those skilled in the art, including its variations, for example as described in the Examples and/or as described by, for example, Liu et al (BMC Genomics 4:19(2003)) and others.

In some embodiments of the invention, there is provided for a method wherein before step (b), or as part of step (b) or before step (c) the nuclei are sorted in order to provide sorted samples comprising one or more, preferably one nuclei per sorted sample, and, preferably wherein, after step (c) or step (d) or before step (e) on one or more of the sorted samples are pooled. As is depicted in the overview of possible embodiments of the method according to the invention (FIG. 1), and although not necessary, during the method a sorting step may be introduced. In some embodiments the sorting is performed before step (b) is performed. In some embodiments the sorting is performed as part of step (b), for example as part of step (ii), which step (ii) is being performed before, during or after step (i) is performed. For example, is some embodiments, in step (b) step (ii) is performed before step (i) is performed. In such embodiment, the cell nuclei, comprising DNA, are contacted with the first antibody-DNA adapter conjugate or with the first antibody and the first antibody-DNA adapter conjugate, and before the DNA is digested with the first restriction endonuclease. In such preferred embodiment, sorting may be performed after the contacting with the first antibody-DNA adapter conjugate or with the first antibody and the first antibody-DNA adapter conjugate, and wherein, after the sorting, the DNA in the nuclei in the sorted samples is digested. In other embodiments, the sorting is performed before step (c), for example after step (b) as shown in FIG. 1 (wherein "secondary antibody conjugate" and primary antibody conjugate" in the Figure refers to the first antibody-DNA adapter conjugate as used herein and wherein "sample adapter" in the Figure refers to the second DNA adapter as used herein. Sorting of the nuclei may be performed using techniques available to the skilled person, such as FACS sorting, and such as those described in the Examples herein. Sorting of the cells/nuclei may, for example, be based on, for example, the stage of the cell cycle of the cells, for example to obtains those cells that are in a particular cell cycle phase, for example, G1/S cell-cycle phase. However, the skilled person understands that sorting of the cells or nuclei in one or more sorted samples may also be based on the detection of other markers, for example based on the presence of level of expression of particular markers, for example using antibody stainings for, for example cell-surface receptors (e.g. to determine the cell of origin, e.g. in blood samples, based on FACS, followed by the method of the invention). In other embodiments, the cells may, for example be stained for the number of mitochondria to relate metabolic activities to underlying epigenetic profiles, e.g. using MitoTracker. The cells, nuclei may be sorted, for example using multiple well plates, in different sorted samples, each comprising, for example one, or more than one cell or nuclei, for example 10, 50, 100, 250, 500 or more nuclei. In another embodiment, the sorted samples may be pooled into one or more samples, for example, and in a preferred embodiment, after step (c), after step (d) or before step (e), for example before amplification and sequencing.

In embodiments of the invention there is also provided for the use of the method of the invention for a wide variety of possible purposes, for example, for generating genome-wide protein-DNA interaction profiles, genome-wide epigenetic profiles, comparing between cell-type specific epigenetic and/or protein-DNA interaction profiles or comparing between epigenetic and/or protein-DNA interaction profiles between embryos at different developmental stages, comparing between epigenetic and/or protein-DNA interaction profiles in tumorigenesis, for example at different disease stages, following different treatment regimes, analysis of protein-DNA interaction at different loci, comparing protein-DNA interaction between one or more samples obtained, comparing protein DNA-interaction between diseased and healthy tissue or between different parts of an organism.

Based on the disclosure herein the skilled person knows how to set-up experiments in line with the above identified purposes and knows how to perform such experiments, with inclusion of the method of the invention.

In embodiments of the invention there is also provided for a kit comprising one or more first antibody-DNA adapter conjugates as disclosed herein, and a corresponding second DNA adapter as disclosed herein. In some embodiments, the kit may further comprise the one or more first restriction endonucleases, the one or more second restrictions endonucleases, and/or the one or more first antibodies (for example in case the method of the invention is performed according to step (b) (ii) (2).

The foregoing description of the specific embodiments will so fully reveal the general nature of the invention that others can, by applying knowledge within the skill of the art (including the contents of the references cited herein), readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein.

All references cited herein, including journal articles or abstracts, published or corresponding patent applications, patents, or any other references, are entirely incorporated by reference herein, including all data, tables, figures, and text presented in the cited references. Additionally, the entire contents of the references cited within the references cited herein are also entirely incorporated by references.

Reference to known method steps, conventional methods steps, known methods or conventional methods is not in any way an admission that any aspect, description or embodiment of the present invention is disclosed, taught or suggested in the relevant art.

It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one of ordinary skill in the art.

It will be understood that all details, embodiments and preferences discussed with respect to one aspect of embodiment of the invention is likewise applicable to any other aspect or embodiment of the invention and that there is therefore not need to detail all such details, embodiments and preferences for all aspect separately.

Having now generally described the invention, the same will be more readily understood through reference to the following examples which is provided by way of illustration and is not intended to be limiting of the present invention. Further aspects and embodiments will be apparent to those skilled in the art.

EXAMPLES

Example 1—Material & Methods

Cell Culture

Haploid KBM7 cells were cultured in suspension in Iscove's Modified Dulbecco's Medium (IMDM, Gibco, 31980030) supplemented with 10% FBS (Sigma, F7524) and 1% Pen/Strep (Gibco, 15140122). Stable KBM7 cells lines with Shield1-inducible Dam-LaminB1 were used as described previously (Kind, J. et al. Cell 163, 134-147 (2015). Cells were passaged every 2-3 days. K562 cells were cultured in suspension in Roswell Park Memorial Institute 1640 (RPMI 1640, Gibco, 61870010) supplemented with 10% FBS and 1% Pen/Strep.

Antibodies

For antibodies see table 1:

| Antibody | Target | Vendor | Catalog number | Application | Produced data for figure | Optimal working concentration |
|---|---|---|---|---|---|---|
| Anti-Lamin B1 antibody - Nuclear Envelope Marker | Lamin B1 | Abcam | ab16048 | Primary antibody-conjugate | 6, 7 | 10 µg/mL |
| | | | | Combined with anti-rabbit IgG conjugate | 3, 4, 5, 6 | 10 µg/mL |
| Tri-methyl-histone-H3 (Lys27) Rabbit mAb | H3K27me3 | Cell Signaling Technologies | 9733S | Primary antibody-conjugate | 6, 7 | 1 in 50 dilution |
| | | | | Combined with anti-rabbit IgG conjugate | 3, 4, 5, 6, 8, 9, 10, 11 | 1 in 200 dilution |
| Histone H3K9me2 antibody (pAb) | H3K9me2 | Active Motif | 39239 | Primary antibody-conjugate | 7 | 25 µg/mL |
| | | | | Combined with anti-rabbit IgG conjugate | 3, 4, 5 | 1 in 200 dilution |
| CTCF (D31H2) XP | CTCF | Cell Signaling Technologies | 3418 | Combined with anti-rabbit IgG conjugate | 3, 5 | 1 in 100 dilution |
| Anti-Trimethyl-Histone H3 (Lys36) antibody, clone RM155 | H3K36me3 | SanBio | 31-1051-00 | Primary antibody-conjugate | 6, 7 | 10 µg/mL |
| | | | | Combined with anti-rabbit IgG conjugate | 3, 4, 5, 6 | 0.5 µg/mL |
| H3K4me3 Monoclonal Antibody (G.532.8) | H3K4me3 | Invitrogen | MA5-11199 | Primary antibody-conjugate | 6, 7 | 5 µg/mL |
| | | | | Combined with anti-rabbit IgG conjugate | 3, 4, 5, 6 | 1 in 2000 dilution |
| Histone H3 (mono methyl K4) antibody | H3K4me1 | Abcam | ab8895 | Primary antibody-conjugate | 6, 7 | 5 µg/mL |
| | | | | Combined with anti-rabbit IgG conjugate | 3, 4, 5, 6 | 1 µg/mL |
| Recombinant Anti-Histone H3 antibody [EPR16987] | Histone H3 | Abcam | ab176842 | Primary antibody-conjugate | 7 | 5 µg/mL |
| Histone H3 trimethyl K36 antibody | H3K36me3 | Homemade, gift by Hiroshi Kimura, Tokyo Institute of Technology | CM333 | Combined with anti-mouse IgG conjugate | 8, 9, 10, 11 | 1 in 1000 dilution |

-continued

| Antibody | Target | Vendor | Catalog number | Application | Produced data for figure | Optimal working concentration |
|---|---|---|---|---|---|---|
| Recombinant Anti-RNA polymerase II CTD repeat YSPTSPS (phospho S5) antibody [3E8] | RNA Polymerase II CTD repeat Ser5 Phosphorylation | Abcam | ab252852 | Combined with anti-rat IgG conjugate | 8, 9, 10, 11 | 1.3 μg/mL |
| Histone H3 Antibody | Histone H3 | Novus Biologicals | NB100-747 | Combined with anti-sheep IgG conjugate | 10, 11 | 5 μg/mL |
| AffiniPure Goat Anti-Rabbit IgG (H + L) | Rabbit IgG | Jackson Immuno Research | 111-005-144 | Seconday antibody-conjugate | 8, 9, 10, 11 | 2 μg/mL |
| AffiniPure Donkey Anti-Mouse IgG (H + L) | Mouse IgG | Jackson Immuno Research | 715-005-150 | Seconday antibody-conjugate | 8, 9, 10, 11 | 2 μg/mL |
| AffiniPure Donkey Anti-Rat IgG (H + L) | Rat IgG | Jackson Immuno Research | 712-005-150 | Seconday antibody-conjugate | 8, 9, 10, 11 | 2 μg/mL |
| AffiniPure Donkey Anti-Sheep IgG (H + L) | Sheep IgG | Jackson Immuno Research | 713-005-147 | Seconday antibody-conjugate | 10, 11 | 2 μg/mL |

ABBC and SOB Adapters

Double-stranded ABBC adapters were conjugated to the antibody via a SPAAC click reaction. The top strand of the double-stranded adapter was produced as HPLC-purified oligo and has a 5' Azide modification (IDT, /5AzideN/) to allow for antibody conjugation. The bottom strand of the double-stranded adapter was produced as standard-desalted oligo and has a 5' Phosphorylation modification (IDT, /5Phos/) and a 2 nt TA (5' to 3') overhang to facilitate ligation to MseI digested DNA. The other elements in the design were (5' to 3'), a 55 nt linker, a NotI recognition site and a 6 nt ABBC barcode. Examples of suitable top and bottom sequences are shown in Table 2.

TABLE 2

(first column indicates name, second column indicates ABBC adapter barcode; third column indicates sequence ((5'-3'), fourth column indicates restriction site)

| | | | |
|---|---|---|---|
| ABID_ABBC_001_top (SEQ ID NO: 1) | CTTCAA | /5AzideN/GTTGGAGTTGAAACGTTCTAATATTCCAATCAGCTTCAACGTGCACCACCGCAGGGCGGCCGCCTTCAACATATGCTAGCATC | NdeI |
| ABID_ABBC_002_top (SEQ ID NO: 2) | AGCCAT | /5AzideN/GTTGGAGTTGAAACGTTCTAATATTCCAATCAGCTTCAACGTGCACCACCGCAGGGCGGCCGCAGCCATCATATGCTAGCATC | NdeI |
| ABID_ABBC_003_top (SEQ ID NO: 3) | ACACGA | /5AzideN/GTTGGAGTTGAAACGTTCTAATATTCCAATCAGCTTCAACGTGCACCACCGCAGGGGGGCCGCACACGACATATGCTACGTAC | NdeI |
| ABID_ABBC_001_bot (SEQ ID NO: 4) | TTGAAG | GATGCTAGCATATGTTGAAGGCGGCCGCCCTGCGGTGGTGCACGTTGAAGCTGATTGGAATATTAGAACGTTTCAACTCCAAC | NdeI |
| ABID_ABBC_002_bot (SEQ ID NO: 5) | ATGGCT | GATGCTAGCATATGATGGCTGCGGCCGCCCTGCGGTGGTGCACGTTGAAGCTGATTGGAATATTAGAACGTTTCAACTCCAAC | NdeI |
| ABID_ABBC_003_bot (SEQ ID NO: 6) | TCGTGT | *GTACGTAGCATATGTCGTGTGCGGCCGCCCTGCGGTGGTGCACGTTGAAGCTGATTGGAATATTAGAACGTTTCAACTCCAAC* | NdeI |

Top and bottom oligos were annealed in a 1:1 ratio at 10 μM final concentration in 1X annealing buffer (10 mM Tris-Cl, pH 7.4, 1 mM EDTA and 100 mM NaCl) in 0.5 mL DNA-low bind tubes (Eppendorf, 0030108400) by incubating in a PCR machine at 95° C. for 5 min, followed by gradual cooling down with 0.5° C. per 15 seconds to 4° C. final.

SCB adapters were designed as forked double-stranded DNA adapters, which can ligate to the ABBC adapters. The bottom adapter has a 5' Phosphorylation modification (IDT, /5Phos/) and 4 nt GGCC (5' to 3') overhang to facilitate ligation to NotI digested DNA. Both top and bottom oligos were produced as standard-desalted oligos. The other elements in the design were (5' to 3') a 6 nt non-complementary fork, the T7 promoter, the 5' Illumina adapter (as used in the Illumina small RNA kit) and a split 2×3 nt Unique Molecular Identifier (UMI) interspaced with a split 2×4 nt SCB barcode. For exemplary suitable top and bottom sequences, see Table 3. Top and bottom oligos were annealed in a 1:1 ratio at 40 μM final concentration in 1X annealing buffer (10 mM Tris-Cl, pH 7.4, 1 mM EDTA and 50 mM NaCl) in a 96-well plate by incubating in a PCR machine at 95° C. for 5 min, followed by gradual cooling down with 0.5° C. per 15 seconds to 4° C. final. Double-stranded SCB adapters were diluted further before use.

TABLE 3

(first column indicates name, second column SBC barcode, third column, sequence ((5'-3')).

| | | |
|---|---|---|
| ABID_SBC_top_001 (SEQ ID NO: 7) | AGGCCATT | GGTGATCCGGTAATACGACTCACTATAGGGGTTCAGAGTTCTACAGTCCGACGATCNNNAGGCNNNCATTAG |
| ABID_SBC_top_002 (SEQ ID NO: 8) | TGAGGCTA | GGTGATCCGGTAATACGACTCACTATAGGGGTTCAGAGTTCTACAGTCCGACGATCNNNTGAGNNNGCTAAG |
| ABID_SBC_top_003 (SEQ ID NO: 9) | GAGAGCTA | GGTGATCCGGTAATACGACTCACTATAGGGGTTCAGAGTTCTACAGTCCGACGATCNNNGAGANNNGCTAAG |
| ABID_SBC_bot_001 (SEQ ID NO: 10) | AATGGCCT | /5Phos/GGCCCTAATGNNNGCCTNNNGATCGTCGGACTGTAGAACTCTGAACCCCTATAGTGAGTCGTATTACCGGGAGCTT |
| ABID_SBC_bot_002 (SEQ ID NO: 11) | TAGCCTCA | /5Phos/GGCCCTTAGCNNNCTCANNNGATCGTCGGACTGTAGAACTCTGAACCCCTATAGTGAGTCGTATTACCGGGAGCTT |
| ABID_SBC_bot_003 (SEQ ID NO: 12) | TAGCTCTC | /5Phos/GGCCCTTAGCNNNTCTCNNNGATCGTCGGACTGTAGAACTCTGAACCCCTATAGTGAGTCGTATTACCGGGAGCTT |

Antibody-DNA Conjugation

Secondary antibody-DNA conjugations were performed as described by Harada, A. et al. 20192, with minor modifications. Briefly, goat anti-rabbit IgG (Jackson ImmunoResearch, 111-005-114), donkey anti-mouse IgG (Jackson ImmunoResearch, 715-005-150), donkey anti-rat IgG (Jackson ImmunoResearch, 712-005-150) or donkey anti-sheep IgG (Jackson ImmunoResearch, 713-005-147) was buffer-exchanged from storage buffer to 100 mM $NaHCO_3$ (pH 8.3) using Zeba™ Spin Desalting columns (40K MWCO, 0.5 mL, ThermoFisher, 87767). Subsequently, 100 μg antibody in 100 μL of 100 mM $NaHCO_3$ (pH 8.3) was conjugated with dibenzocyclooctyne (DBCO)-PEG4-NHS ester (Sigma, 764019) by adding 0.25 μL of DBCO-PEG4-NHS (dissolved at 25 mM in dimethylsulfoxide (DMSO), 10 times molar ratio to antibody) and incubated for 1 hour at room temperature on a tube roller. The sample was passed through a Zeba™ Spin Desalting column to remove free DBCO-PEG4-NHS and to directly buffer-exchange to PBS. DBCO-PEG4-conjugated antibodies were concentrated using an Amicon Ultra-0.5 NMWL 10-kDa centrifugal filter (Merck Milipore, UFC501024) and measured on a NanoDrop™ 2000. The DBCO-PEG4-conjugated antibody was diluted to 1 μg/μL in PBS. Conjugation of antibody with ABBC adapter was performed at a molar ratio of 1:2 by mixing 75 μL of DBCO-PEG4-conjugated antibody (75 μg, in PBS) with 100 μL of double-stranded ABBC adapter (10 μM, see section 'ABBC and SCB adapters'). Samples were incubated at 4° C. for 1 week on a rotor at 8 rpm. Subsequent clean-up of the ABBC-antibody conjugate was performed as described by Harada, A. et al. (Harada, A. et al. Nature Cell Biology 21, 287-296 (2019)), with an average yield of 20-30 μg. ABBC-antibody conjugates were stored at 4° C.

Primary antibody-DNA conjugations were performed as described herein with minor modifications. Primary antibodies were first cleaned using the Abcam Antibody Purification Kit (Protein A) (Abcam, ab102784) following manufacturer's instructions (performing overnight incubation at 4° C. in the spin cartridge on a rotor at 8 rpm). All four elution phases were taken along to maximize the yield. Purified antibodies were concentrated using an Amicon Ultra-0.5 NMWL 10-kDa centrifugal filter, after which 350 μL 100 mM $NaHCO_3$ was added and concentrated again to exchange buffers. The concentrated antibody was measured on the Nanodrop™ 2000. Subsequent steps were performed as described in the section "Antibody-conjugation" from the DBCO-PEG4-NHS incubation onwards.

Cell Harvesting, Fixation and Permeabilization

Cells were harvested (~15×10$^6$ cells) and washed once with PBS. Centrifugation steps were at 200 g for 4 minutes at 4° C. Cells were fixated in 1% formaldehyde (Sigma, F8875) in PBS for 5 minutes, before quenching the reaction with 125 mM final concentration of glycine (Sigma, 50046) and placing the cells on ice. Subsequent steps were performed on ice or at 4° C. Cells were washed three times with PBS before resuspension in Wash buffer 1 (20 mM HEPES pH 7.5 (Gibco, 15630-056), 150 mM NaCl, 66.6 μg/mL Spermidine (Sigma, S2626-1G), 1X cOmplete™ protease inhibitor cocktail (Roche, 11697498001), 0.05% Saponin (Sigma, 47036-50G-F), 2 mM EDTA) and transferred to a 1.5 mL protein-low bind Eppendorf tube (Eppendorf, EP0030108116-100EA). Cells were permeabilized for 30 minutes at 4° C. on a tube roller. Bovine Serum Albumin (BSA, Sigma, A2153-50g) was added to 5 mg/mL final concentration and incubated for another 60 minutes at 4° C. on a tube roller. Permeabilized nuclei were used for antibody incubation (standard MAb-ID procedure) or bulk digestion (Alternative MAb-ID procedure).

Antibody Incubations

Centrifugation steps were at 200 g for 4 minutes at 4° C.

Primary Antibody-Conjugates.

Permeabilized nuclei (see section Cell harvesting, fixation and permeabilization) were counted on a TC20™ Automated Cell Counter (BioRad, 1450102). Nuclei were diluted to ~3×10$^6$ cells/mL in Wash buffer 1, of which 200 μL (~600,000 nuclei) was used for each primary antibody incubation. Primary antibody conjugated to an ABBC adapter (see Antibody-DNA conjugation section) was added and incubated overnight at 4° C. on a tube roller (see table 1 for antibody concentrations used). For each experiment, a control sample without primary antibody was taken along. The next morning, the nuclei were washed two times with Wash Buffer 2 (20 mM HEPES pH 7.5, 150 mM NaCl, 66.6 μg/mL Spermidine, 1X cOmplete™ protease inhibitor cocktail, 0.05% Saponin) and resuspended in 200 μL Wash Buffer 2 containing Hoechst 34580 (Sigma, 63493) at 1 μg/mL. Nuclei were incubated for 1 hour at 4° C. on a tube roller. Finally, nuclei were washed two times with Wash Buffer 2 and resuspended 500 μL Wash Buffer 2 before proceeding to FACS sorting.

Secondary antibody-conjugates.

Permeabilized nuclei (see section Cell harvesting, fixation and permeabilization) were counted on a TC20™ Automated Cell Counter. Nuclei were diluted to ~$3\times10^6$ cells/mL in Wash buffer 1, of which 200 μL (~600,000 nuclei) is used for each primary antibody incubation. Primary antibody (unconjugated) was added and nuclei were incubated overnight at 4° C. on a tube roller (see table 1 for antibody concentrations). For each experiment, a control sample without primary antibody was taken along. The next morning, the nuclei were washed two times with Wash Buffer 2 (20 mM HEPES pH 7.5, 150 mM NaCl, 66.6 μg/mL Spermidine, 1X cOmplete™ protease inhibitor cocktail, 0.05% Saponin) and resuspended in 200 μL Wash Buffer 2 containing Hoechst 34580 at 1 μg/mL. Secondary antibody conjugated to an ABBC adapter (see Antibody-DNA conjugation section) was added (2 μg/mL) and incubated for 1 hour at 4° C. on a tube roller. Finally, nuclei were washed two times with Wash Buffer 2 and resuspended in 500 μL Wash Buffer 2 before proceeding to FACS sorting.

FACS Sorting

Nuclei were pipetted through a Cell Strainer Snap Cap into a Falcon 5 mL Round Bottom Polypropylene Test Tube (Fisher Scientific, 10314791) just prior to sorting on a BD Influx or BD FACsJazz Cell sorter. Haploid KBM7 nuclei as well as diploid K562 nuclei were sorted in G1/S cell-cycle phase, based on the Hoechst levels. For 1000-cell samples, nuclei were sorted into a tube of a PCR tube strip containing 5 μL 1X CutSmart buffer (NEB, B7204S) per well. The final volume after sorting was ~7.5 μL per tube. For samples with 100 cells or less, the appropriate number of nuclei was sorted into a 384-well PCR plate (BioRad, HSP3831) containing 200 nL 1X CutSmart buffer and 5 μL mineral oil (Sigma, M8410) per well. Plates were sealed with aluminum covers.

MAb-ID Procedure

Manual Preparation of MAb-ID Samples

Samples containing 1000 nuclei were processed in PCR tube strips. Samples were spun briefly in a table-top rotor between incubation steps. 2.5 μL of Digestion-1 mix (MseI (12.5 U, NEB, R0525M) and/or MboI (12.5 U, NEB, R0147M) in 1X CutSmart buffer) was added to a total volume of 10 μL per tube, including 7.5 μL sorting volume.

Samples were incubated in a PCR machine for 3 hours at 37° C. before holding at 4° C. 5 μL of rSAP mix (rSAP (1 U, NEB, M0371L) in 1X CutSmart buffer (for MseI/NdeI digestions) or 1X NEBuffer 3.1 (NEB, B7203S), for all digestions including MboI/BglII)) was added to a total volume of 15 μL per tube. Samples were incubated for 30 minutes at 37° C., then 3 minutes at 65° C. before transfer to ice. 5 μL of Digestion-2 mix (NdeI (5 U, NEB, R0111L) and/or BglII (5 U, NEB, R0144L) in 1X CutSmart buffer (for MseI/NdeI digestions) or 1X NEBuffer 3.1 (for all digestions including MboI/BglII)) was added to a total volume of 20 μL per tube. Samples were incubated for 1 hour at 37° C., before holding at 4° C. 6 μL of Ligation-1 mix (3.75 U T4 DNA ligase (Roche, 10799009001), 33.3 mM DTT (Invitrogen, 707265), 3.33 mM ATP (NEB, P0756L) in 1X Ligase Buffer (Roche, 10799009001)) was added to a total volume of 26 μL per tube. Samples were incubated for 16 hours at 16° C., before holding at 4° C. 4 μL of Lysis mix (Proteinase K (5.05 mg/mL, Roche, 3115879001), IGEPAL CA-630 (5.05%, Sigma, 18896) in 1X CutSmart buffer) was added to a total volume of 30 μL per tube. Samples were incubated for 4 hours at 56° C., 6 hours at 65° C. and 20 minutes at 80° C. before holding at 4° C. 10 μL of Digestion-3 mix (5 U NotI-HF (NEB, R3189L) in 1X CutSmart buffer) was added to a total volume of 40 μL. Samples were incubated for 3 hours at 37° C. before holding at 4° C. 2.5 μL of uniquely barcoded SCB adapter (550 nM, see section ABBC and SCB adapters) was added to reach a final concentration of ~25 nM during ligation. 12.5 μL of Ligation-2 mix (6.25 U T4 DNA ligase, 34 mM DTT, 3.4 mM ATP in 1X Ligase Buffer) is added to each tube to a final volume of 55 μL during ligation. Samples were incubated for 12 hours at 16° C. and 10 minutes at 65° C. before holding at 4° C.

Robotic Preparation of MAb-ID Plates 384-well PCR plates with sorted nuclei were processed using a Nanodrop II robot at 12 psi pressure (BioNex) for adding all mixes. Indicated volumes are per well. Between handling, plates were spun 2 minutes at 1000 g at 4° C. each time. 200 nl of Digestion-1 mix (MseI (0.5 U) and/or MboI (0.5 U) in 1X CutSmart buffer) was added to a total volume of 400 nL per well. Plates were incubated in a PCR machine for 3 hours at 37° C. before holding at 4° C. 200 nL of rSAP mix (rSAP (0.04 U) in 1X CutSmart buffer (for MseI/NdeI digestions) or 1X NEBuffer 3.1 (for all digestions including MboI/BglII)) was added to a total volume of 600 nL per well. Plates were incubated for 30 minutes hours at 37° C., then 3 minutes at 65° C. before directly placing on ice. 200 nL of Digestion-2 mix (NdeI (0.2 U) and/or BglII (0.2 U) in 1X CutSmart buffer (for MseI/NdeI digestions) or 1X NEBuffer 3.1 (for digestions including MboI/BglII)) was added to a total volume of 800 nL per well. Plates are incubated for 1 hour at 37° C., before holding at 4° C. 240 nL of Ligation-1 mix (0.15 U T4 DNA ligase, 33.3 mM DTT, 3.33 mM ATP in 1X Ligase Buffer) was added to a total volume of 1040 nL per well. Plates were incubated for 16 hours at 16° C., before holding at 4° C. 160 nL of Lysis mix (Proteinase K (5.05 mg/mL), IGEPAL CA-630 (5.05%) in 1X CutSmart buffer) was added to a total volume of 1200 nL per well. Plates were incubated for 4 hours at 56° C., 6 hours at 65° C. and 20 minutes at 80° C. before holding at 4° C. 400 nL of Digestion-3 mix (0.2 U NotI-HF in 1X CutSmart buffer) was added to a total volume of 1600 nL per well. Plates were incubated for 3 hours at 37° C. before holding at 4° C. 100 nL of uniquely barcoded SCB adapter (110 to 550 nM, see section ABBC and SCB adapters) was added to each well using a Mosquito HTS robot (TTP Labtech) to reach a final concentration of ~25 nM during ligation. 500 nL of Ligation-2 mix (0.25 U T4 DNA ligase, 34 mM DTT, 3.4 mM ATP in 1X Ligase Buffer) was added to a final volume of 2200 nL during ligation. Plates were incubated for 12 hours at 16° C. and 10 minutes at 65° C. before holding at 4° C.

Alternative Manual Preparation of MAb-ID Samples

All centrifugation steps of nuclei were at 200 g for 4 minutes at 4° C. After nuclei permeabilization and blocking (see section Cell harvesting, fixation and permeabilization), nuclei were washed three times with 1X CutSmart buffer. Nuclei were resuspended in 50 μL 1X CutSmart buffer and transferred to a 0.5 mL protein-low bind Eppendorf tube. 50 μL Digestion-bulk mix (500 U MseI in 1X CutSmart buffer) was added, to a total volume of 100 μL. Nuclei were incubated in an oven at 37° C. on a rotor at 8 rpm for 3 hours. Then, 25 μL rSAP-bulk mix (20 U rSAP in 1X CutSmart buffer) was added to a total volume of 125 μL and nuclei were incubated in an oven at 37° C. on a rotor at 8 rpm for another 30 minutes. rSAP was heat-inactivated by incubating the sample at 65° C. for 3 minutes in a PCR machine before immediately placing the sample on ice. The nuclei were washed three times with Wash Buffer 1 before continuing with the antibody incubations (see sections Antibody incubations). After the incubation with the primary or secondary antibody-conjugate, the nuclei were washed three times with 1X CutSmart buffer, before resuspending in 25 μL 1X Ligase Buffer. 25 μL Ligation-bulk-1 mix was added (25 U T4 DNA ligase in 1X Ligase Buffer) to a final volume of 50 μL and nuclei were incubated at 16° C. in an incubator on a rotor at 8 rpm for a minimum of 16 hours. After incubation, nuclei were washed once in 1X CutSmart buffer before resuspending in 500 μL 1X CutSmart buffer containing Hoechst 3480 (1 μg/mL) and incubating for 1 hour at 4° C. on a tube roller. Nuclei were spun and resuspended in in 500 μL 1X CutSmart buffer before proceeding to FACS sorting in PCR tube strips (see section FACS sorting). 2.5 μL of Lysis-bulk mix (Proteinase K (2.68 mg/ml), IGEPAL CA-630 (2.68%) in 1X CutSmart buffer) was added to a total volume of 10 μL per tube, including 7.5 μL sorting volume. Samples were incubated in a PCR machine for 4 hours at 56° C., 6 hours at 65° C. and 20 minutes at 80° C. before holding at 4° C. 10 μL of Digestion-3 mix (5 units NotI-HF in 1X CutSmart buffer) was added to a total volume of 20 μL. Samples were incubated for 3 hours at 37° C. before maintaining samples at 4° C. 1.5 μL of barcoded SCB adapter (550 nM, see section ABBC and SCB adapters) was added to reach a final concentration of ~25 nM during ligation. 12.5 μL of Ligation-bulk-2 mix (6.25 U T4 DNA ligase, 17.2 mM DTT, 1.72 mM ATP in 1X Ligation Buffer) was added to each tube to a final volume of 34 μL during ligation. Samples were incubated for 12 hours at 16° C. and 10 minutes at 65° C. before maintaining holding at 4° C.

Library Preparation

Samples ligated with unique SCB adapters were pooled, either 2-4 1000 nuclei samples or a full 384-well plate were pooled for combined in vitro transcription (IVT). To reduce batch effects, controls (secondary antibody-conjugates without primary antibody incubation) were pooled with their corresponding samples whenever possible. For 384-well plates, mineral oil was removed by spinning the sample for 2 minutes at 2000 g and transferring the liquid phase to a clean tube, which was repeated three times. After pooling, samples were incubated for 10 minutes with 1.0 volume CleanNGS magnetic beads (CleanNA, CPCR-0050), diluted 1:4 to 1:10 in bead binding buffer (20% PEG 8000, 2.5 M NaCl, 10 mM Tris-HCl, 1 mM EDTA, 0.05% Tween 20, pH 8.0 at 25° C.). The bead dilution ratio depended on the total volume, 1:4 for 1000 nuclei samples and 1:10 for a full 384-well plate. Samples were placed on a magnetic rack (DynaMag™-2, ThermoFisher, 12321D) to collect beads on the side of the tube. Beads were washed two times with 80% ethanol and briefly allowed to dry before resuspending in 8 μL water. In vitro transcription was performed by adding 12 μL IVT mix from the MEGAScript T7 kit (Invitrogen, AM1334) for 14 hours at 37° C. before holding at 4° C. Library preparation was subsequently performed as described previously (Rooijers, K. et al. Nature Biotechnology 37, 766-772 (2019)), using 5 μL of aRNA and 8 to 11 PCR cycles, depending on the aRNA yield. Purified aRNA from different IVT reactions (with unique SCB adapters) can be pooled before proceeding with cDNA synthesis to reduce batch effects. Libraries were run on the Illumina NextSeq500 platform with high output 1×75 bp, the Illumina NextSeq2000 platform with high output 1×100 bp or the Illumina NextSeq2000 platform with high output 2×100 bp.

Example 1—Results

Mapping Distinct Chromatin Types with Secondary Antibody-DNA Conjugates

Figure 2:
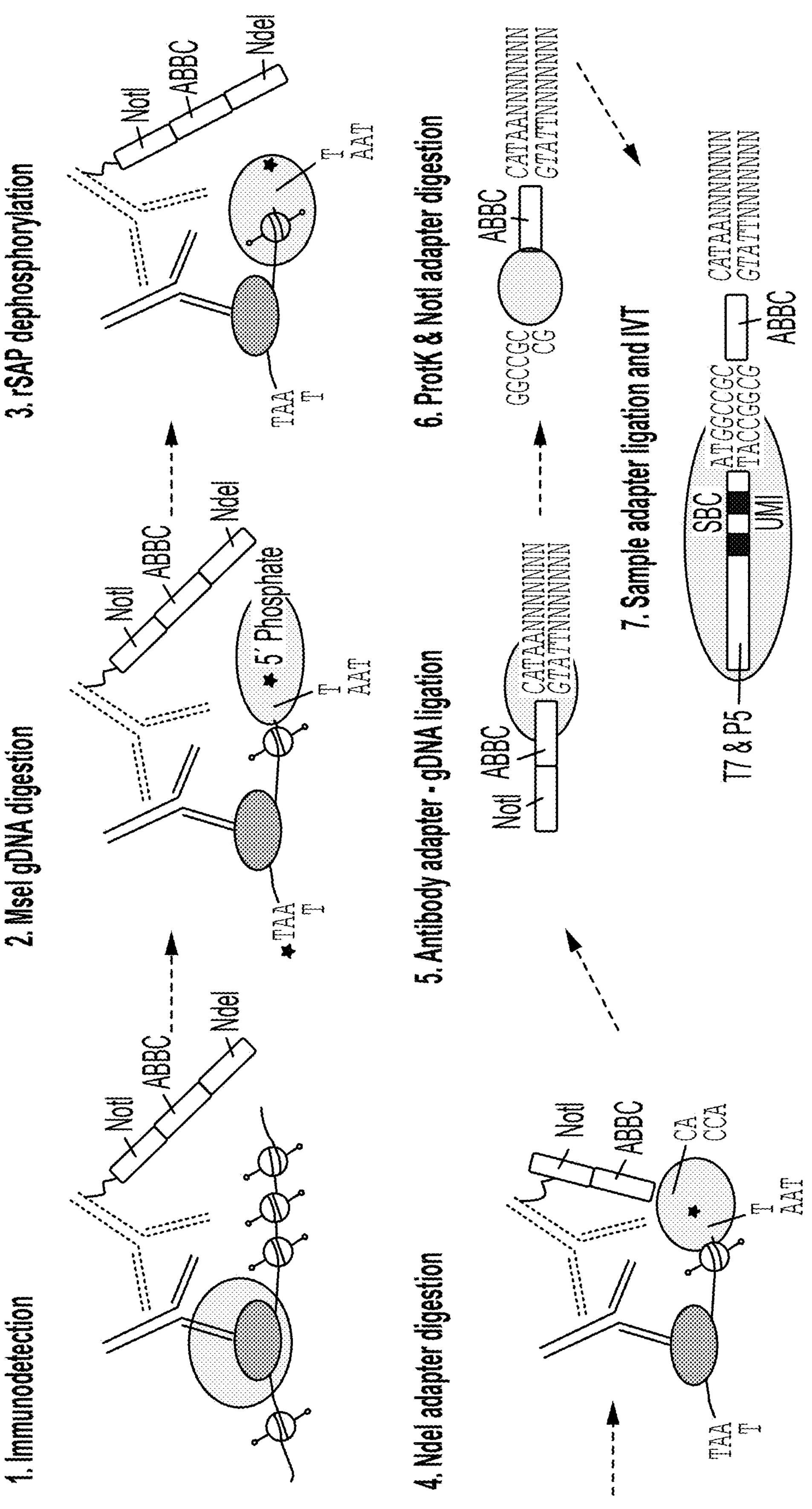
FIG. 2: Schematic depiction of an embodiment of the method of the invention, involving primary antibody immuno-detection (e.g. using a 'first antibody') followed by subsequent genomic targeting via an antibody-DNA conjugate (e.g. using a 'first antibody-DNA adapter conjugate'). ABBC=Antibody Barcode; UMI=Unique Molecular Identifier; SBC=Sample Barcode. In practice a single antibody is decorated with several adapters and multiple secondary antibodies bind to each primary antibody. In an alternative method of the invention, and wherein, for example, no first antibody is used, the adapter will be directly conjugated to a primary antibody including a unique ABBC per antibody to discriminate between epitopes.
Figure 3:
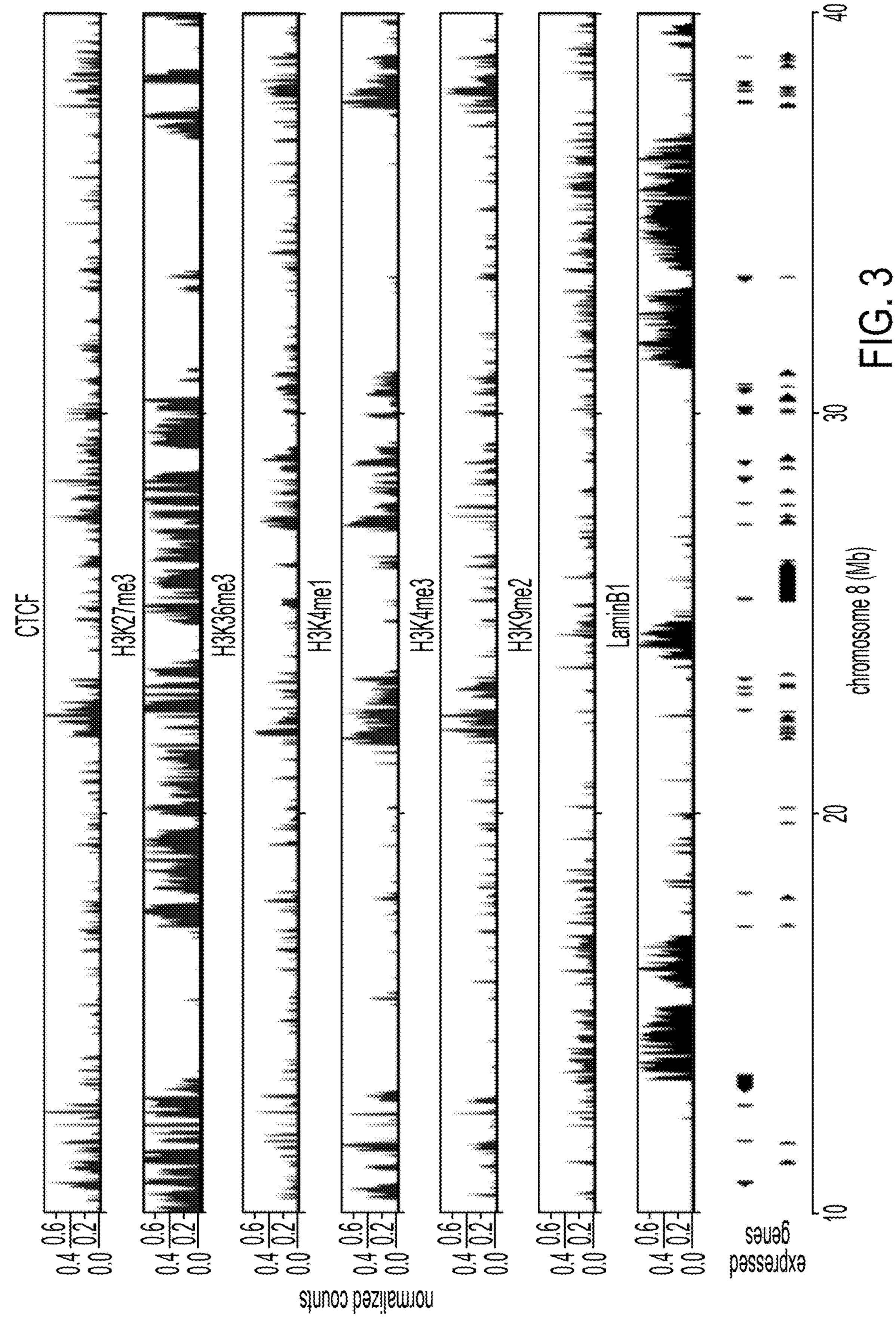
FIG. 3: Genomic profiles obtained for CTCF, H3K27me3, H3K36me3, H3K4me1, H3K4me3, H3K9me2, and Lamin B1 in 1000-cell samples of human K562 cells. Profiles were obtained via immuno-detection with the indicated primary antibodies, followed by incubation and detection with antibody-DNA conjugates. The tracks depict the interaction profiles on 30 megabases (Mb) on chromosome 8.
Figure 4A:
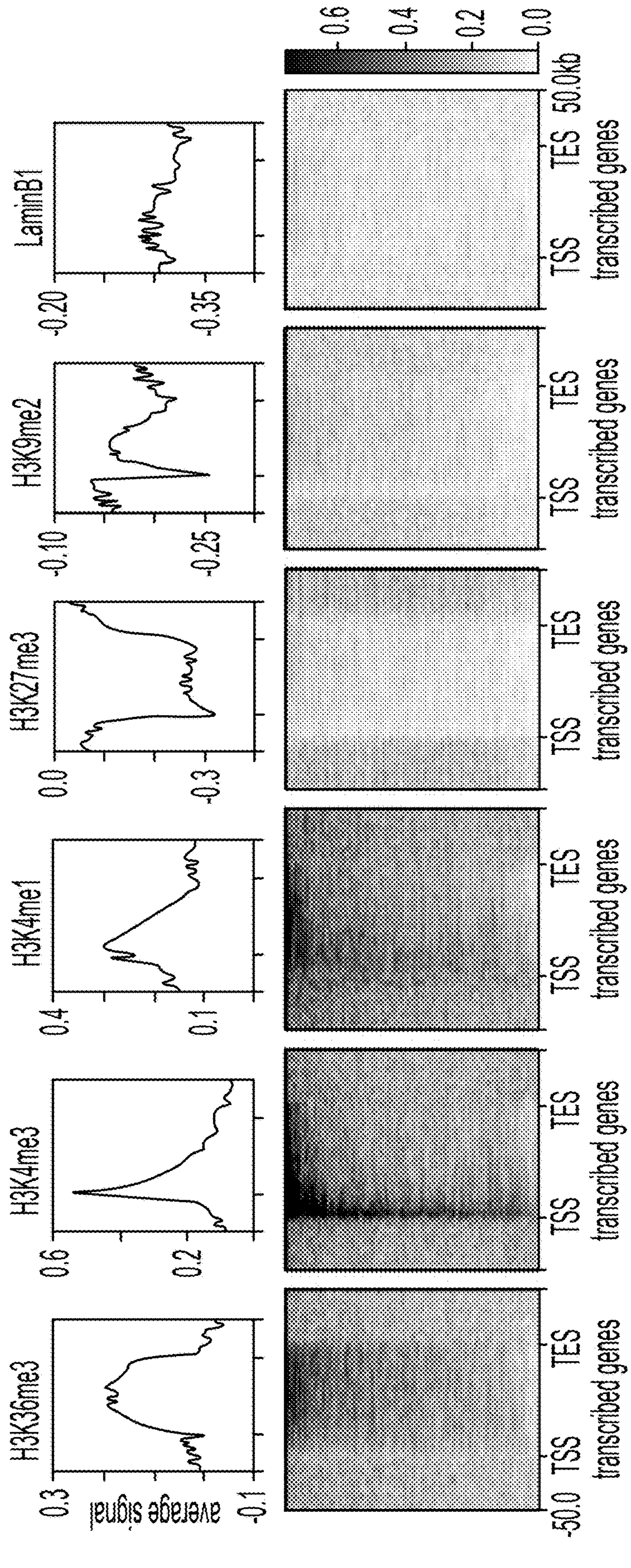
FIGS. 4A-4B: Enrichments of read counts over actively transcribed genes (FIG. 4A) and inactive LAD domains (FIG. 4B) for 1000-cell K562 samples obtained by immuno-detection with secondary antibody-DNA conjugates in samples incubated with primary antibodies against: H3K36me3, H3K4me3, H3K4me1, H3K27me3, H3K9me2 and Lamin B1.
Figure 4B:
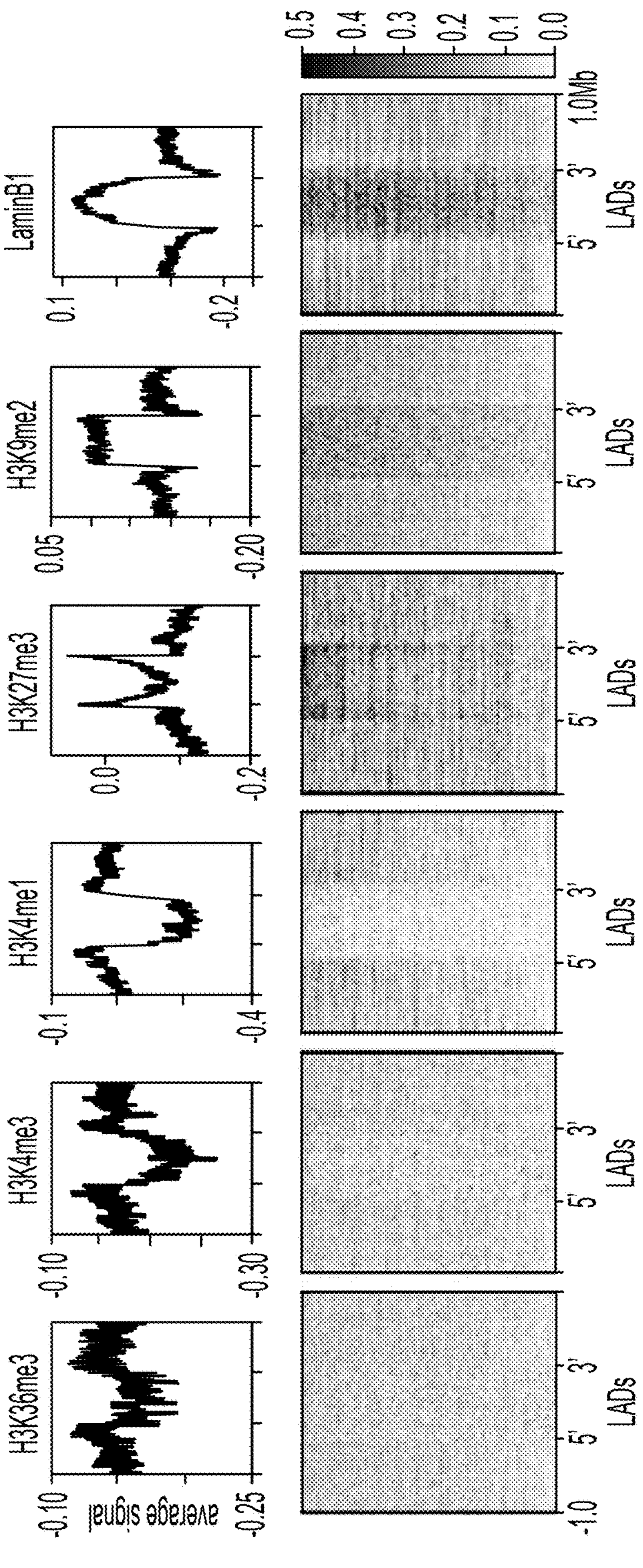
Figure 5:
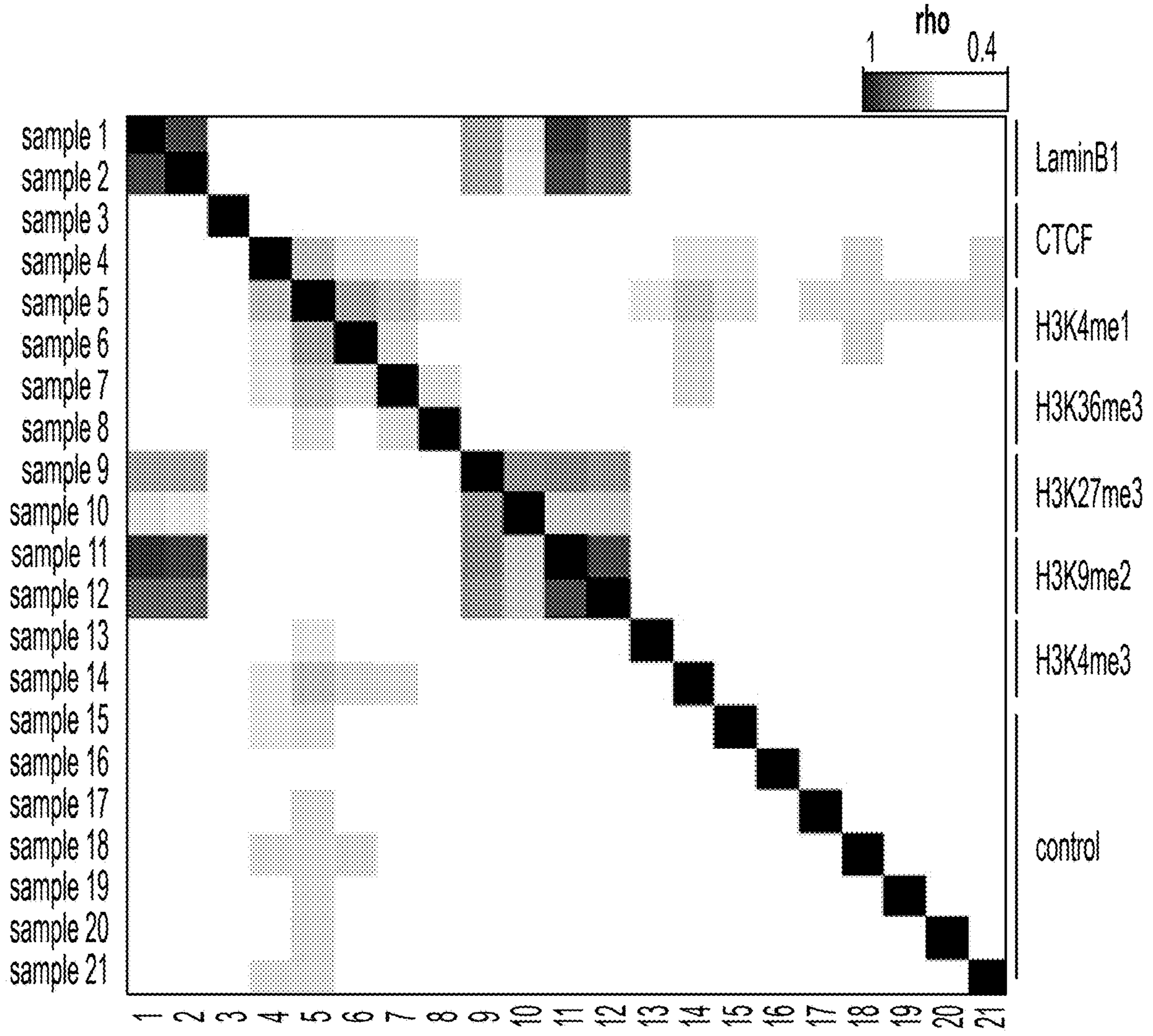
FIG. 5: Correlation-heatmap of biological replicate samples obtained with the method of the invention using immuno-detection with antibody-DNA conjugates in samples incubated with primary antibodies against: CTCF, H3K27me3, H3K36me3, H3K4me1, H3K4me3, H3K9me2, Lamin B1, and control samples (not incubated with primary antibodies). Correlation is Spearman's rho.

First, to test for the specificity of the approach in mapping different chromatin types, 1000-cell samples of K562 cells were incubated with the following primary antibodies: CTCF, H3K27me3, H3K36me3, H3K4me1, H3K4me3, H3K9me2 or Lamin B1. The detection of the different antibodies was performed by immuno-detection with secondary antibody-DNA conjugates (as displayed in FIG. 2). The genomic profiles obtained for these primary antibodies are distinct and correspond to the known genomic segmentation of chromatin types into transcriptional active or inactive regions (FIG. 3). This is further confirmed by alignments of signal over genes (FIG. 4*a*) and lamina associated domains (LADs) (FIG. 4*b*). LADs represent an inactive type of chromatin that lines the inner nuclear membrane. Finally, independently generated replicate samples cluster together in a correlation heat map and correlations are highest between samples targeting similar types of chromatin (FIG. 5). For example, the signal of H3K9me2, H3K27me3 and Lamin B1 (all known to be enriched in inactive chromatin) display high correlation scores for all samples. This, as opposed to low correlation scores between these inactive chromatin types and active chromatin types marked by H3K36me3, H3K4me1 and H3K4me3 (FIG. 5). These results indicate that a robust protocol for the detection of many different chromatin types in low cell numbers is provided.

Mapping Distinct Chromatin Types with Primary Antibody-DNA Conjugates

Figure 6:
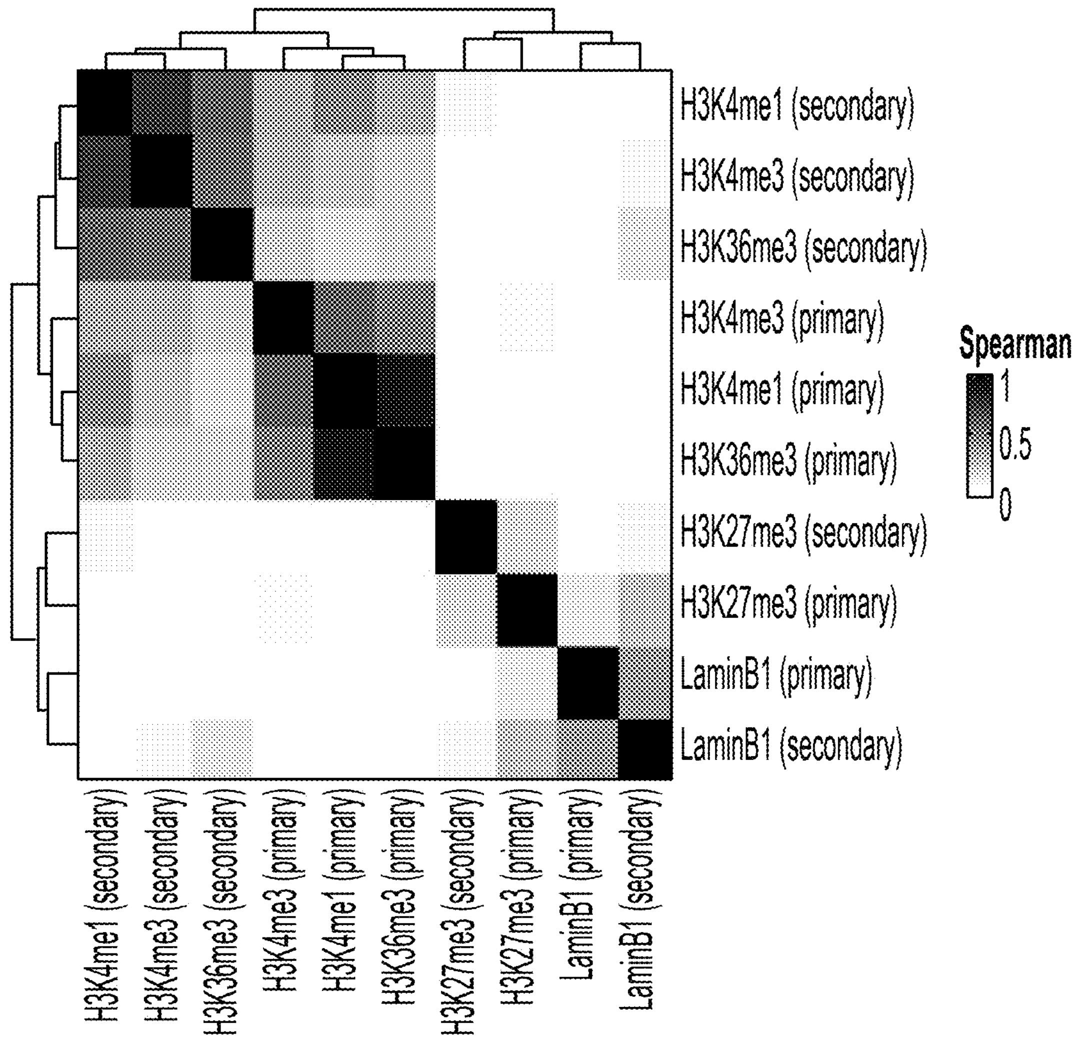
FIG. 6: Correlation-heatmap of genomic profiles obtained with primary-DNA conjugates and secondary-DNA conjugations. Correlation is Spearman's rho.
Figure 7A:
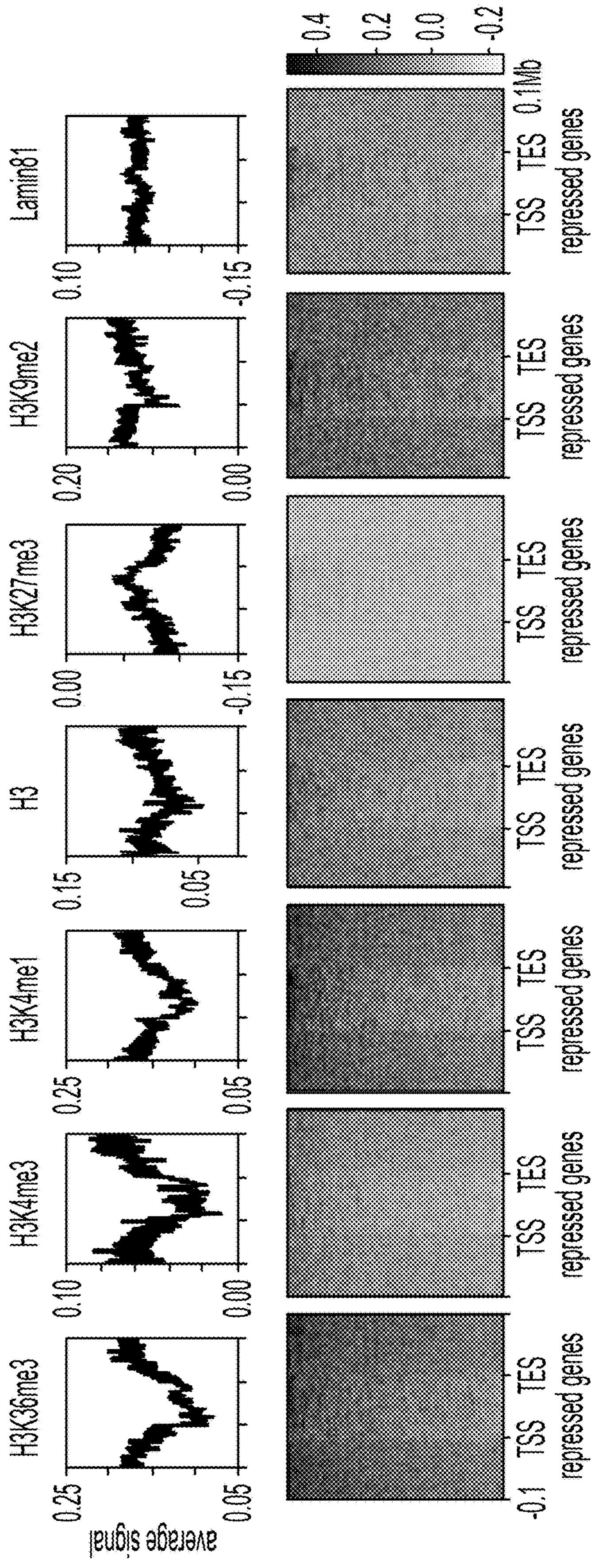
FIGS. 7A-7B: Enrichments of read counts over actively transcribed genes (FIG. 7A) and inactive LAD domains (FIG. 7B) for 1000-cell K562 samples obtained by immunodetection with primary antibody-DNA conjugates against H3K36me3, H3K27me3, H3K4me3, H3K4me1, Histone H3, H3K27me3, H3K9me2, and Lamin B1.
Figure 7B:
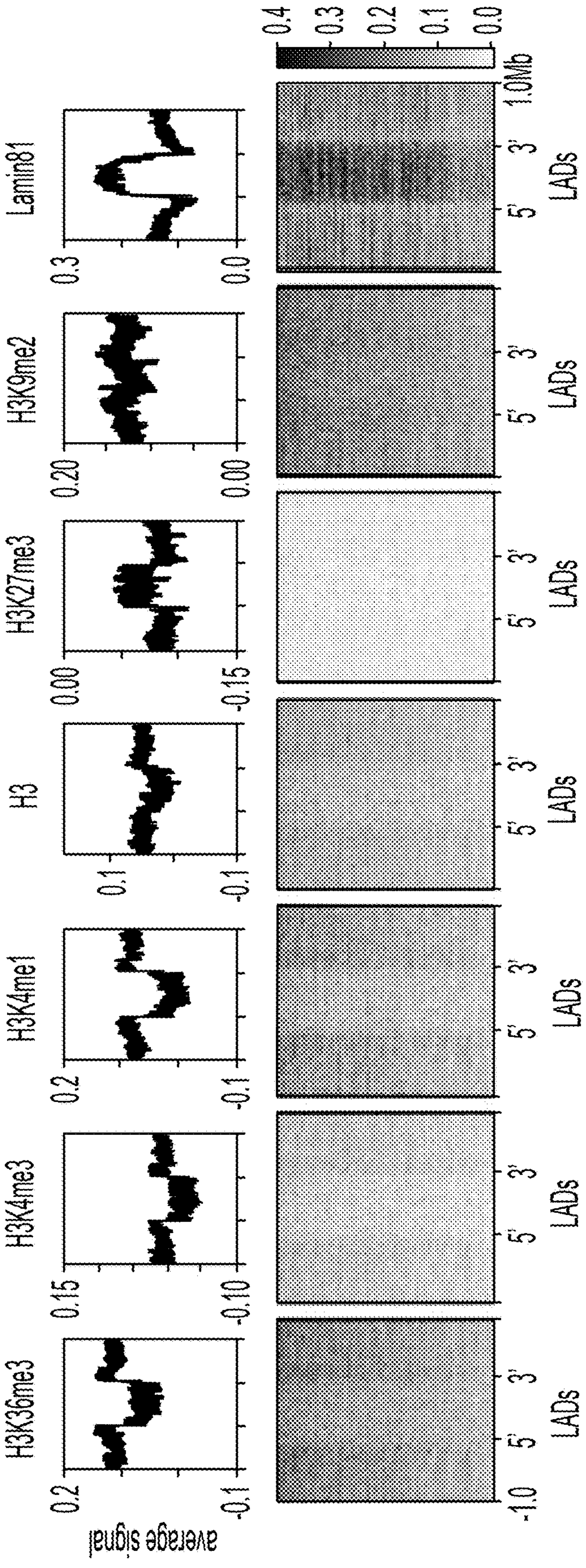

The use of secondary antibody-DNA conjugates may limit the flexibility to select antibody of choice. This, because the choice is restricted by the diversity in secondary antibodies species that is available (e.g. generally only rabbit or mouse) and primary antibody counterparts that can be used. To overcome this potential limitation and to enable multiplexing many antibodies in the same sample, antibody-DNA conjugates with seven primary antibodies targeting various histone PTMs (post-translational modifications) and Lamin B1 in 1000-cell K562 samples were also generated. The obtained profiles display good correspondence to matching profiles obtained with secondary antibodies (FIG. 6). Also, the enrichments over genomic features are in correspondence with the known genomic distributions (FIG. 7*a*-*b*). These results show that using the MAb-ID variant with primary conjugates yields similar epigenetic profiles and can be used to probe the epigenome.

Figure 8:
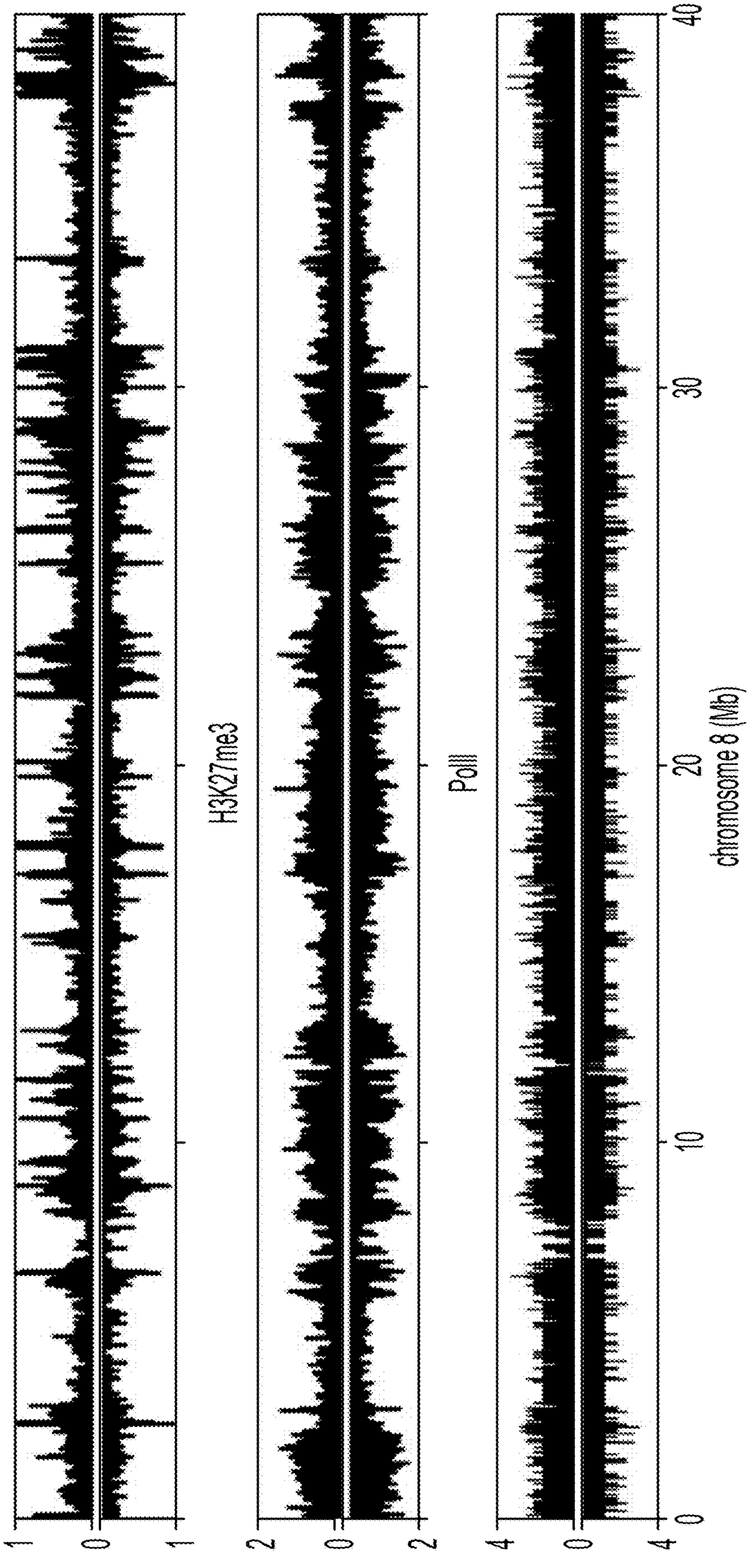
FIG. 8: Genomic profiles obtained for H3K36me3, H3K27me3, and RNA Polymerase 2 in a 1000-cell multiplexed K562 sample (top profiles), compared to profiles obtained for the same antibodies processed as individual samples (bottom mirror images). The multiplexed profiles are obtained via immuno-detection with first the indicated primary antibodies followed by incubations with the matching secondary anti-mouse, anti-rabbit and anti-rat antibody-DNA conjugates. The tracks depict the interaction profiles on 40 megabases (Mb) on chromosome 8.
Figure 9A:
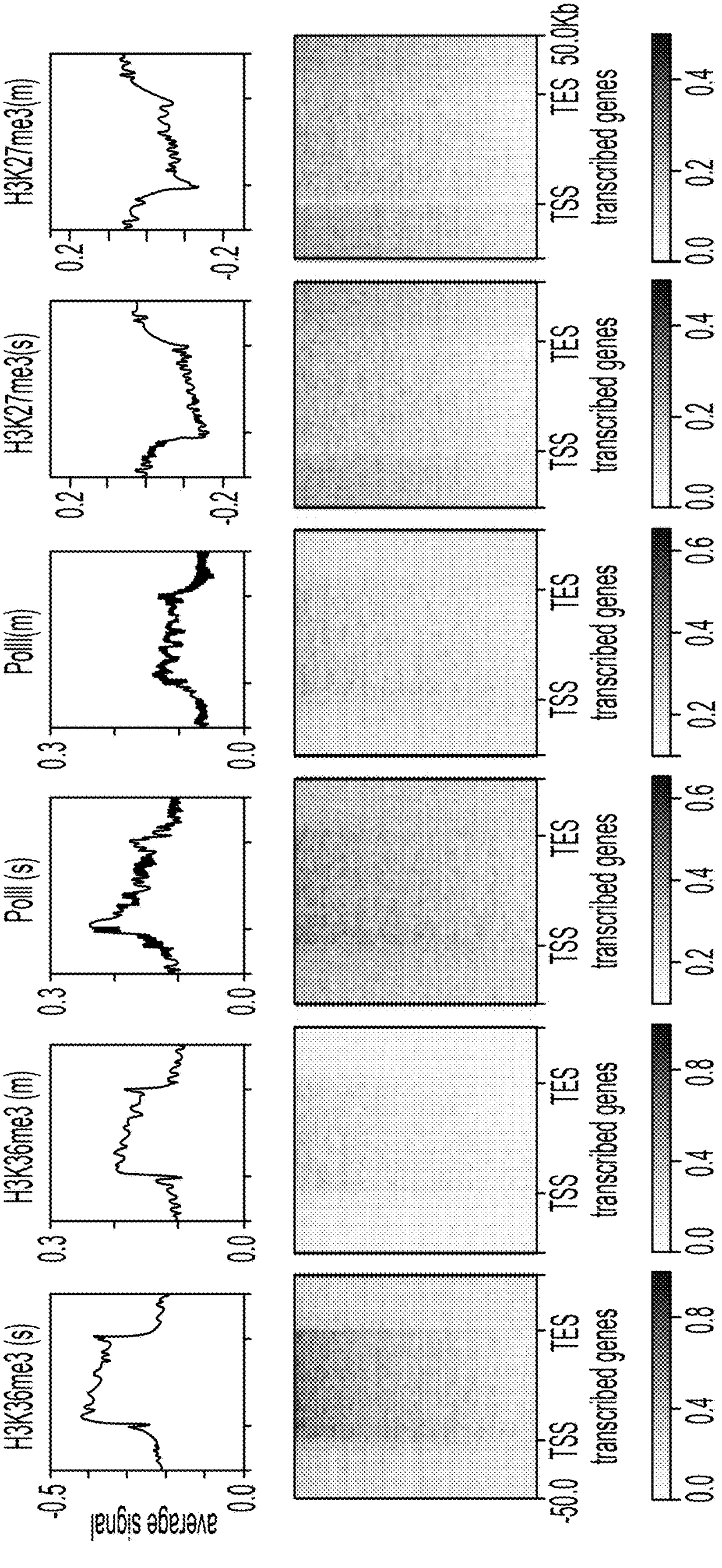
FIGS. 9A-9B: Enrichments of read counts over actively transcribed genes (FIG. 9A) and Polycomb-group repressed genes (FIG. 9B) for 1000-cell K562 samples obtained with multiplexed stainings against H3K36me3, H3K27me3 and RNA Polymerase 2. (s) depicts samples processed as single samples and (m) indicates samples that are obtained in a single multiplexed sample.
Figure 9B:
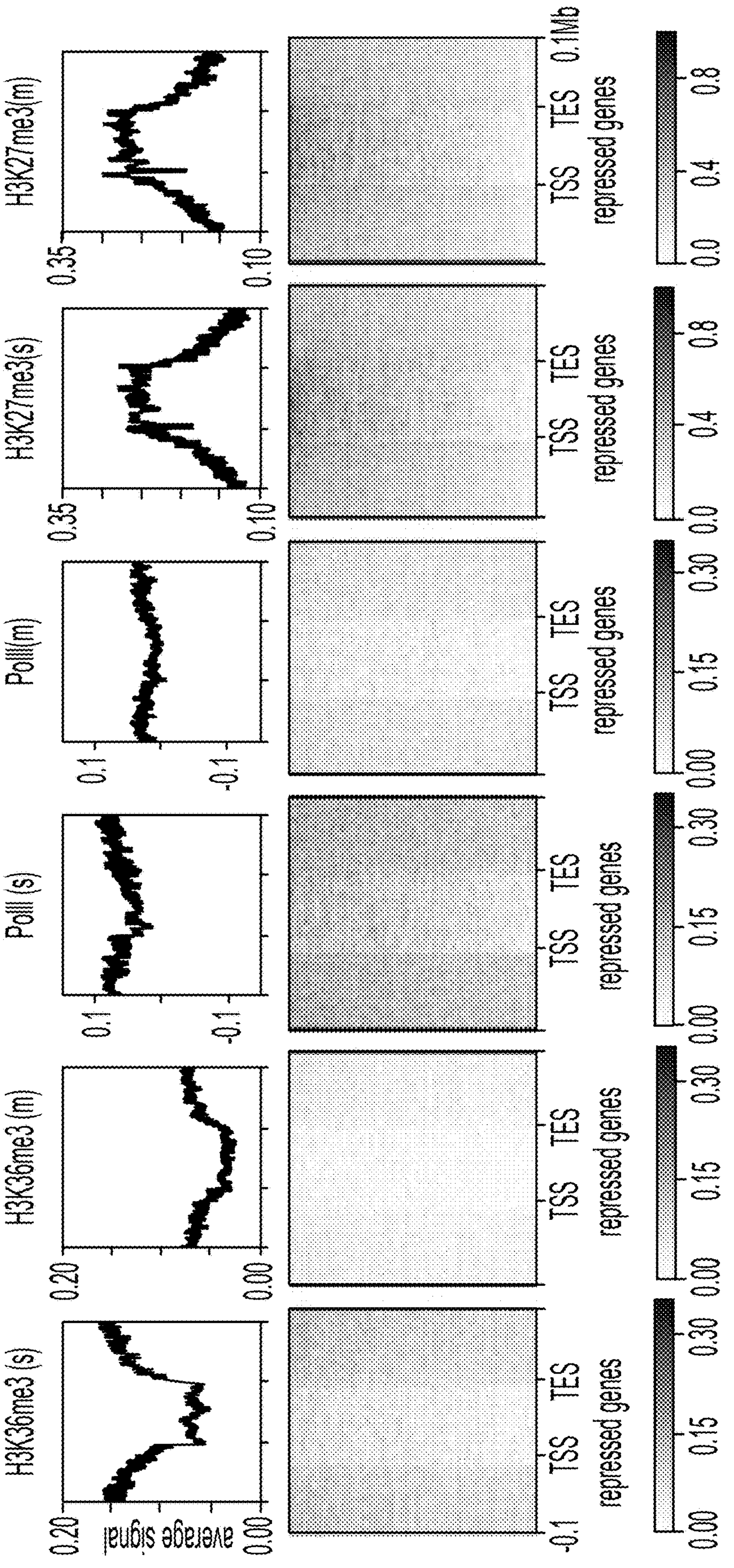
Figure 10:
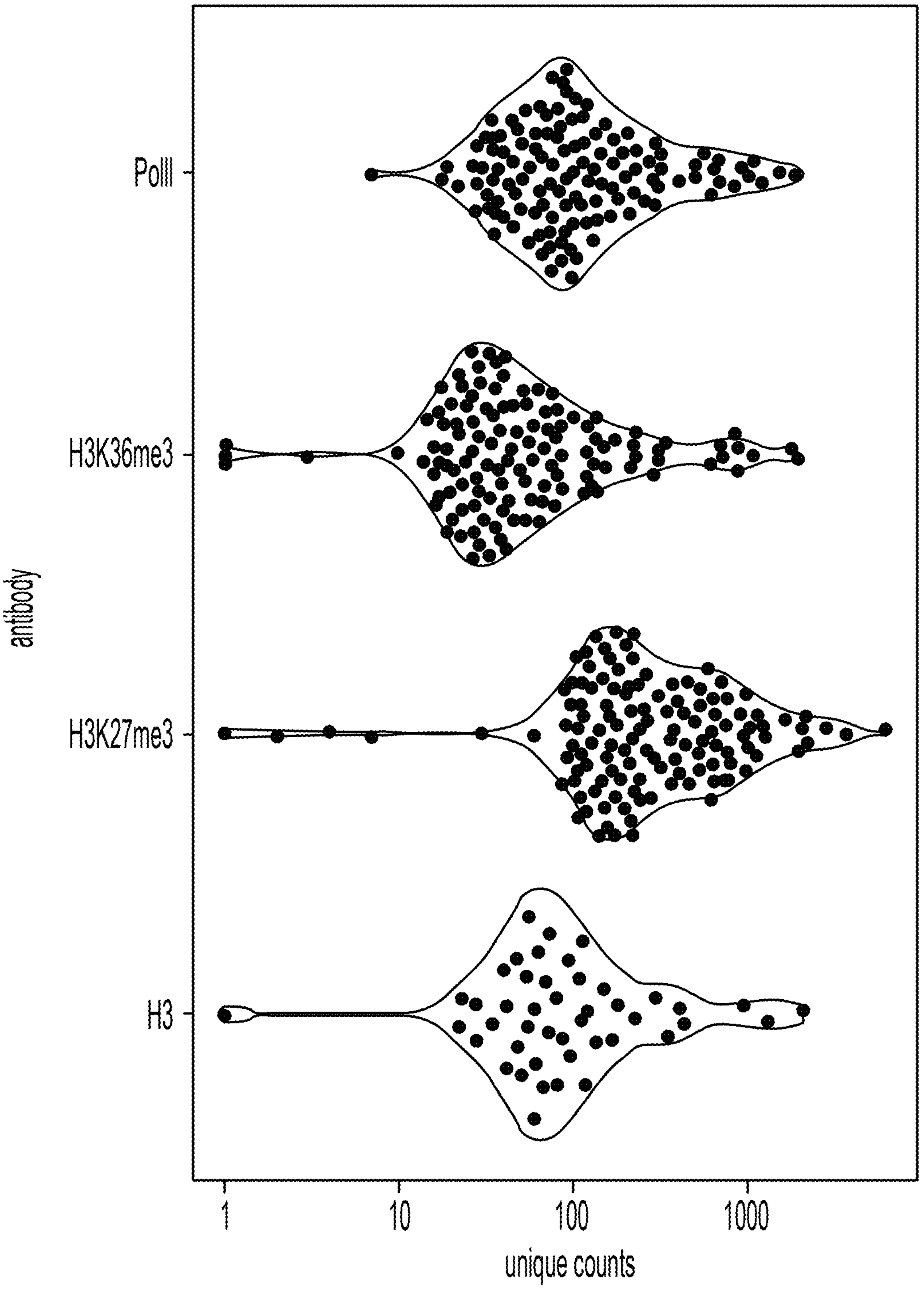
FIG. 10.

Multiplexing Chromatin Types in a Single Sample with Secondary Antibody-DNA Conjugates A major advantage of the method of the invention is the possibility to obtain multiplexed genomic landscapes with low-input samples. To confirm multiplexing is indeed possible and that multiplexing experiments match data quality of measurements performed via sequential experiments in parallel samples, four binding profiles in the same sample were simultaneously mapped. To this end, four primary antibodies that were raised in different animals were selected. Histone H3 (goat), RNA Polymerase 2 (rat), H3K36me3 (mouse) and H3K27me3 (rabbit) were selected and the corresponding secondary antibody DNA-conjugates for all four animal species were generated. This experiment was performed with 1000 K562 cells and resulted in chromatin profiles which closely matched 1000-cell samples in which immuno-detection was performed for every antibody individually (FIG. 8). Also, the genomic interactions occur in regions as expected for the corresponding chromatin types (FIG. 9*a-b*). Thus, a method for the simultaneous detection of multiple chromatin profiles in low-cell samples is provided.

Figure 11A:
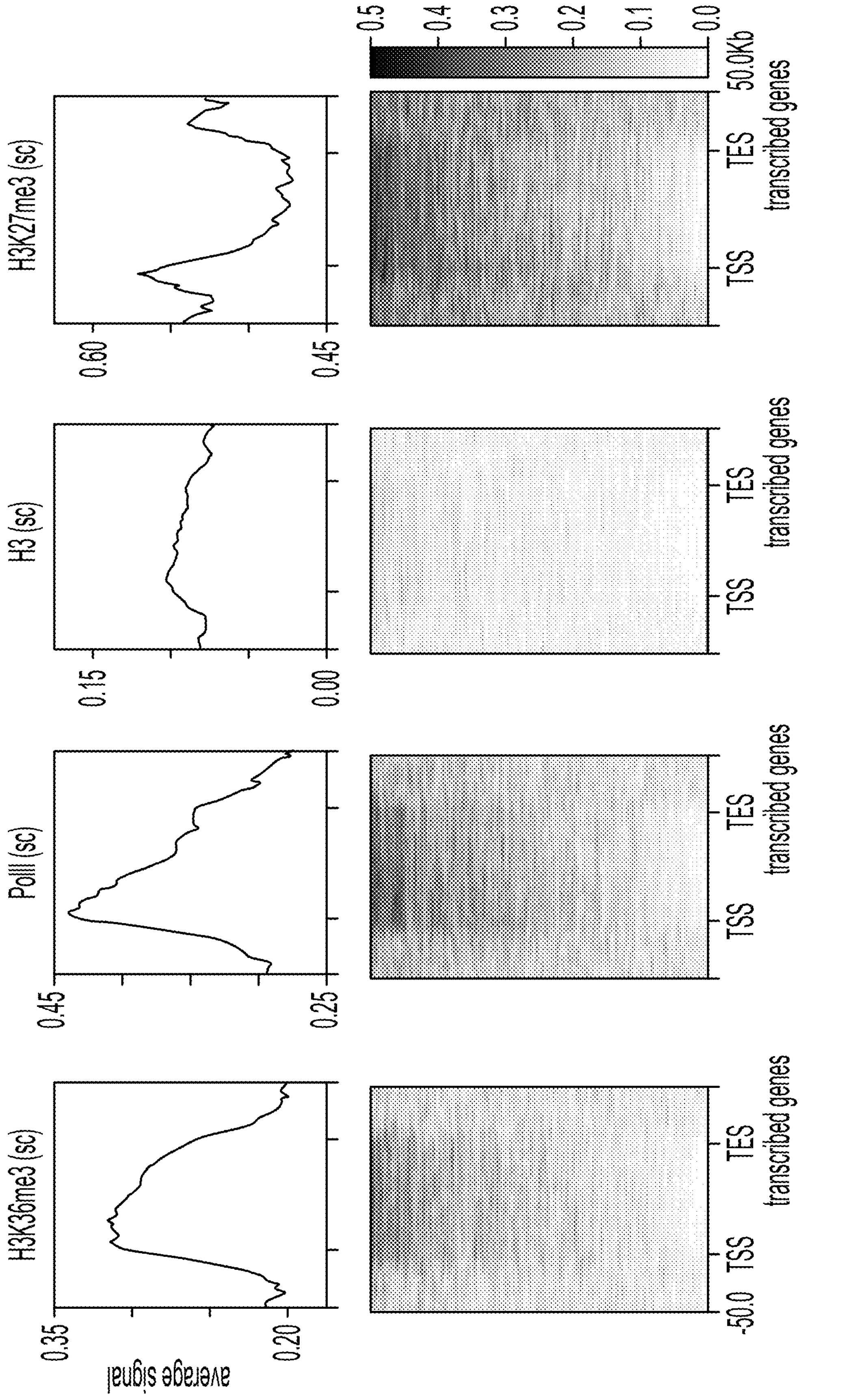
FIGS. 11A-11B: Enrichments of read counts over actively transcribed genes (FIG. 11A) and Polycomb-group repressed genes (FIG. 11B) of single-cell samples obtained with multiplexed immuno-detection of RNA Polymerase 2, H3K36me3, H3K27me3 and Histone H3. Note that the enrichments are in accordance with the expected patterns for the corresponding chromatin states.
Figure 11B:
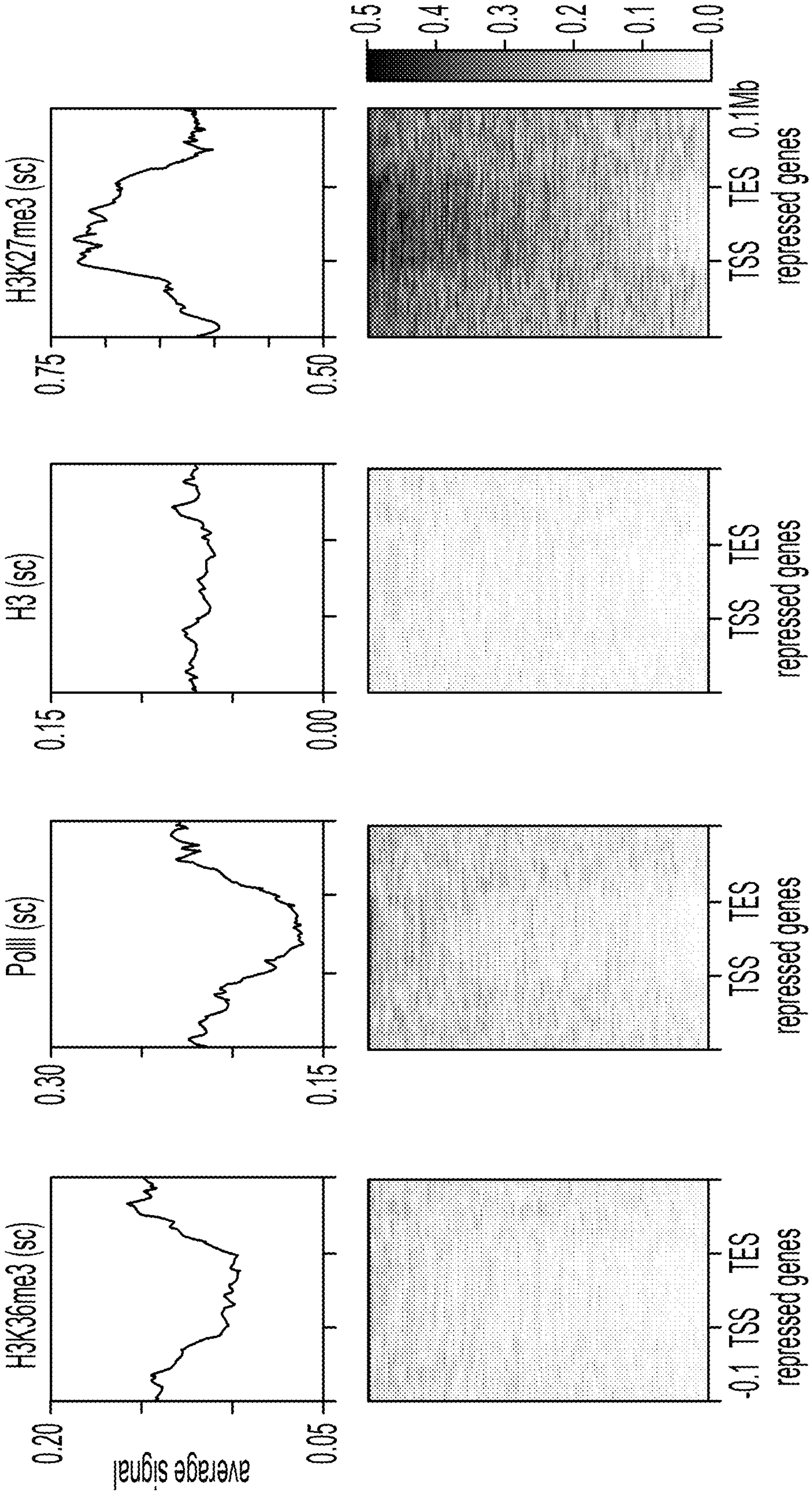

Multiplexing Chromatin Types in Single Cells with Secondary Antibody-DNA Conjugates Thus far, experiments were performed in samples with low-cell material. In order to obtain information from single cells fluorescent-activated cell sorting (FACS) was performed to capture single cells in individual wells of a 384-well plate. The wells obtained a unique sample barcode to discriminate between individual cells. These experiments were performed with a multiplexed set of antibodies that target Histone H3, RNA Polymerase 2, H3K36me3, and H3K27me3 simultaneously via secondary antibody-DNA conjugates. Barring these read counts, RNA polymerase 2, H3K36me3 and H3K27me3 profiles matched the patterns as obtained for the 1000-cell samples when single-cell counts were combined (FIG. 11). This indicates that the reads obtained in individual cells are specific to the chromatin region that is targeted by the primary antibody. These results show that meaningful multiplexed single-cell measurements with the method of the invention as disclosed herein, also referred to as MAb-ID, is provided.

Example 2—Results

Genomic Profiling of a Broad Spectrum of Epigenetic Markers

Figure 12A:
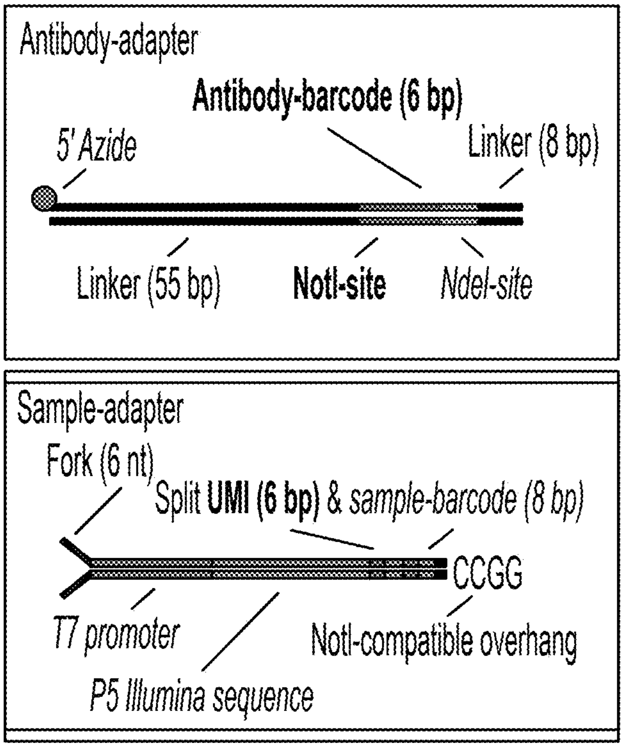
FIGS. 12A-12C: Schematic of the DNA adapter design (both antibody and sample adapter) (FIG. 12A) and Pearson correlations between MAb-ID and ChIP-seq datasets (FIG. 12B) and distribution of MAb-ID and ChIP-seq signal around the TSS or Polycomb domain borders (based on ChromHMM calls). The 50% decay from the peak top is indicated (FIG. 12C).

Each antibody is first covalently linked to one or more double-stranded DNA-adapter(s) (antibody-adapter). In the case of multiple double stranded DNA-adapters, the DNA-adapters were identical, but various non-identical DNA-adapters can be used as well. The DNA-adapters were linked to the antibodies using a basic two-step $Cu^{2+}$-free click-chemistry approach (SPAAC) (Harada, A et al., *Nat. Cell Biol.* 21, 287-296 (2018); Agard, N. J., Prescher, J. A. & Bertozzi, C. R., *J. Am. Chem. Soc.* 126, 15046-15047 (2004) and van Buggenum, J. A. G. L. et al., *Sci. Rep.* 6, 22675 (2016)). (FIG. 12A). These antibodies are then employed in the method of the invention as disclosed herein, also referred to as MAb-ID. The method preferably starts with 1) harvesting cells, for example about ~250,000 cells and isolating nuclei during a mild fixation step, 2) incubation with uniquely barcoded antibody-DNA conjugates, 3) Fluorescent-Activated Cell Sorting (FACS) into tubes or 384-well plates, 4) digestion of the genome with a first restriction enzyme, preferably MseI which recognizes TTAA sequence motifs, 5) dephosphorylation of the digested genome to prevent self-ligation of genomic fragments, preferably followed by heat activation, for example mild heat activation (e.g. less than 5 minutes, for example 3 minutes or less at 65 degrees Celsius; in order to deactivate the phosphatase), 6) digestion of the antibody-adapter with the a second, but preferably different, restriction enzyme, preferably NdeI, which leaves a compatible overhang with the first restriction enzyme, and 7) ligation of the antibody-adapter(s) into the genome. The position of the antibody-adapter within the genome thereby becomes a proxy for the localization of the epitope of interest. The method of the invention as disclosed herein continues with 8) lysis and proteinase K treatment followed by 9) digestion with a restriction enzyme to enable subsequent ligation of a sample-adapter, preferably NotI. The sample-adapter includes a T7 RNA polymerase promoter sequence, an Illumina P5-sequence, and a unique-molecular identifier (UMI) interspersed with a sample-barcode (FIG. 12A). This enables pooling multiple samples for linear amplification by in vitro transcription and subsequent Illumina library preparation as previously described (Rooijers, K. et al. *Nat. Biotechnol.* 37, 766-772 (2019)).

Comparing MAb-ID Signal to Known Methods in the Art

Figure 12B:
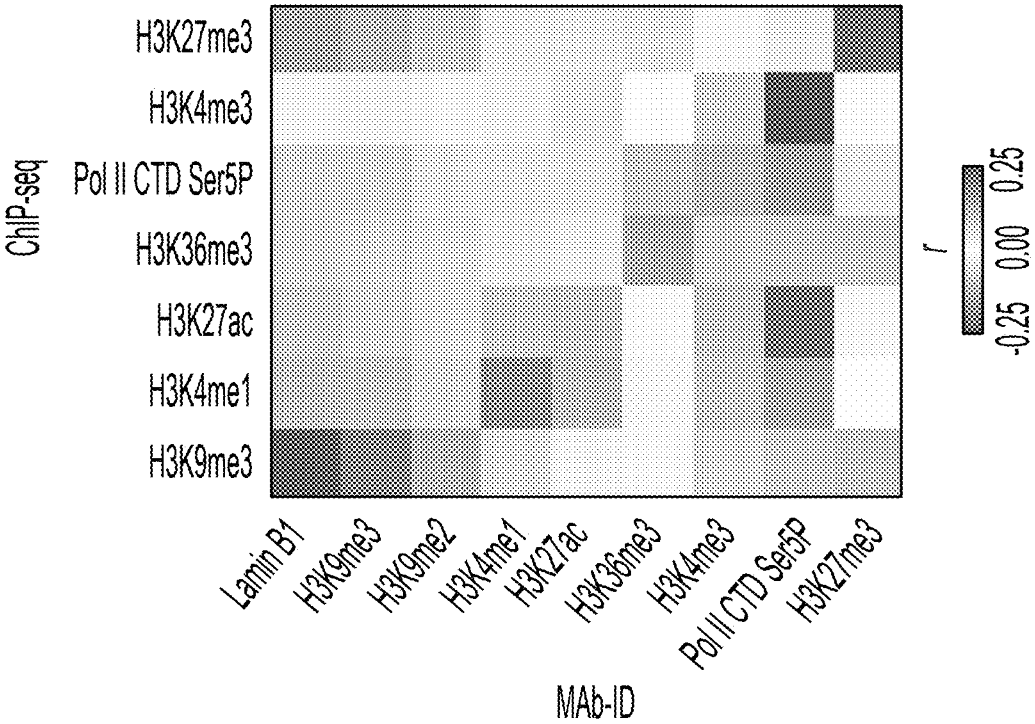

Visualization of the normalized data by uniform manifold approximation and projection (UMAP) shows that the samples identified with method of the invention as disclosed herein (MAb-ID) group together with their corresponding chromatin types. The results show a good concordance between biological replicates, demonstrating the robustness of the MAb-ID procedure. The genome-wide MAb-ID data correlates well with ChIP-seq data of matching histone PTMs and with publicly available DamID data of Lamin B1 (FIG. 12B). On a local scale, the profiles of MAb-ID signal across the linear genome show the expected patterns of enrichment with high similarity between MAb-ID and ChIP-seq datasets. Thus, these results show that the method as disclosed herein correlates well with known methods and datasets.

Exploring On-Target Specificity of MAb-ID

Figure 12C:
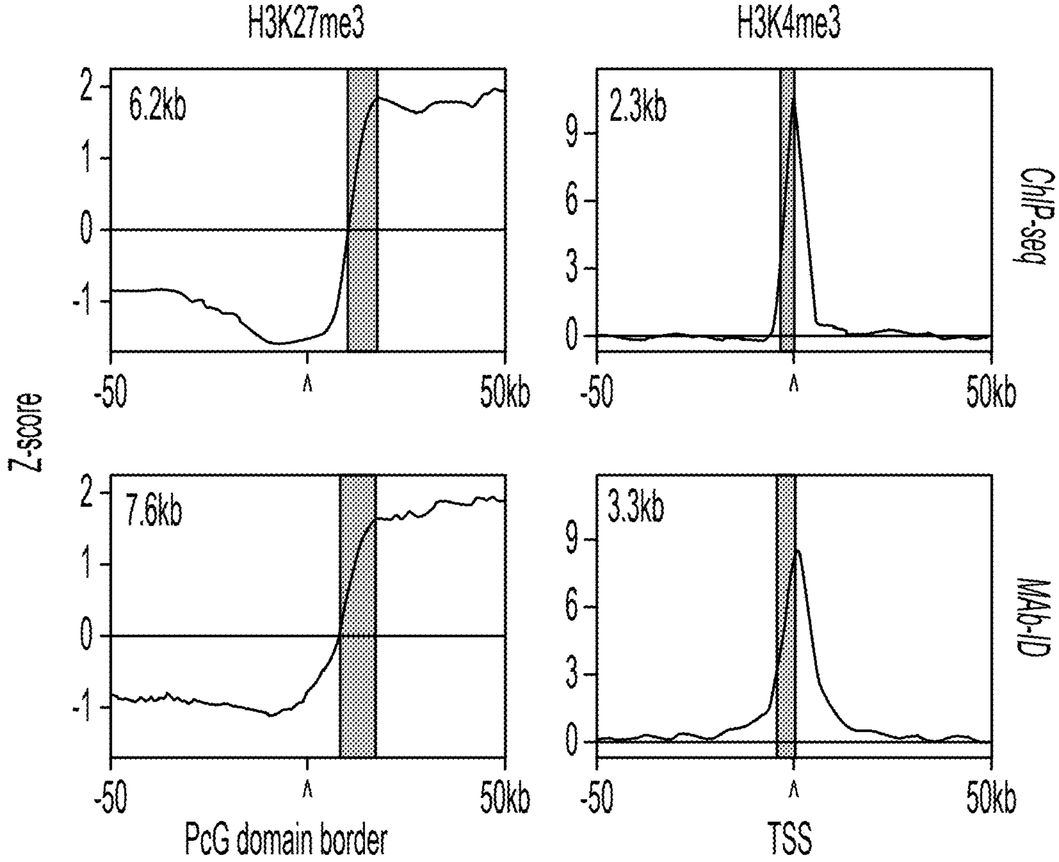

Enrichments of MAb-ID signal over relevant genomic regions, such as ChIP-seq peaks/domains or genes were calculated. All chromatin types mapped with MAb-ID displayed an enrichment of signal over the matching genomic regions, irrespective of chromatin type. The enrichment of signal of active chromatin types over gene bodies also scales according to the transcriptional activity of these genes, as is expected for these types of chromatin. These results show that the method as disclosed herein displays enriched signal of the matching genomic regions and that it correlates well with known methods and datasets Quantifying the Signal Distribution of MAb-ID Over Regions Compared to Known Methods in the Art Finally, to determine the resolution of MAb-ID, the signal distribution of H3K4me3 over transcription start sites (TSS) and H3K27me3 over Polycomb-group domains (based on ChromHMM domain calls; Ernst, J. et al., *Nature* 473, 43-49 (2011).) and comparing this to the corresponding ChIP-seq datasets was quantified (FIG. 12C). Results show that for H3K4me3 the signal decays to 50% (compared to 100% at the TSS) at around 3-4 kb distance, for H3K27me3 this distance corresponds to 7-8 kb around the domain border. Compared to ChIP-seq, MAb-ID signal thus generally extends an additional 1-2 kb in either direction. In summary, the results of this example show that MAb-ID, accurately profiles diverse chromatin types and chromatin-associated proteins in as little as a 1000 cells.

Example 3—Results

Multiplexing Four Antibodies on One Sample is Possible without Loss of Individual Data Quality.

Figure 13A:
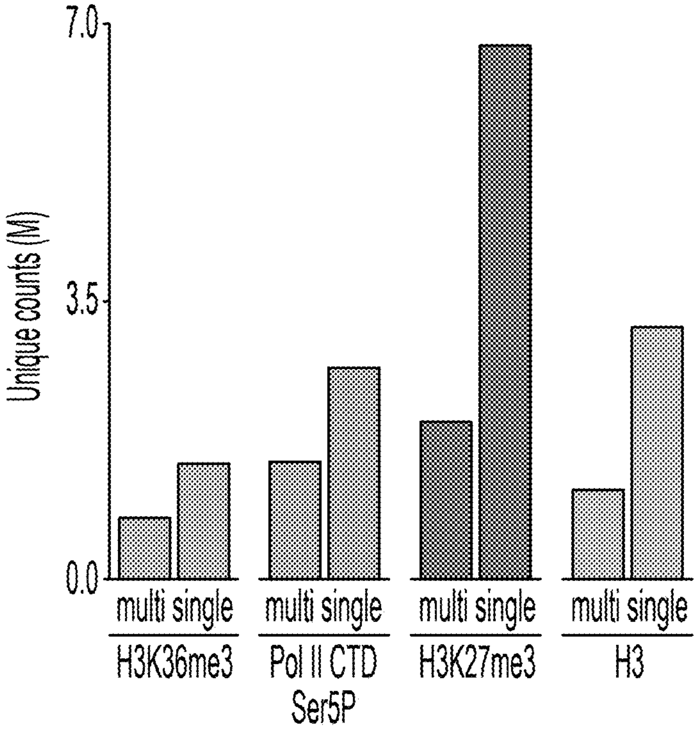
FIGS. 13A-13B: Number of unique read counts per MAb-ID sample (FIG. 13A) and percentages of read counts assigned during different filtering steps for individual or combined MAb-ID samples (FIG. 13B).
Figure 13B:
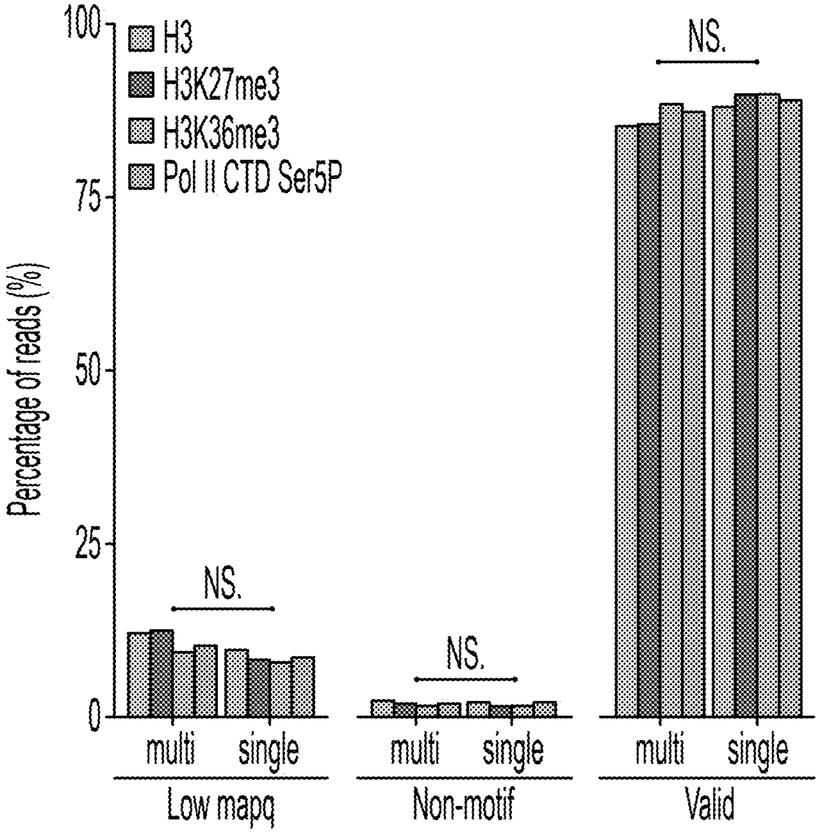

A potential of the method as disclosed herein, also referred to as MAb-ID, is the multiplexing of different antibodies in the same sample and profiling several chromatin states together. Experiments combining four antibodies of different host-origin on the same sample were performed, along with barcoded secondary antibody DNA-conjugates specific for each host, preferably each barcoded secondary antibody was a uniquely barcoded secondary antibody Antibodies used against H3K27me3 (rabbit) and RNA Polymerase II (CTD Ser5-phosphorylated, rat) H3K36me3 (mouse) and histone H3 (sheep) were used (Table 4). The specificity of these antibodies was verified.

very comparable between single and combined samples (FIG. 13A-B). The genome-wide correlation coefficients with ChIP-seq data for the corresponding targets are generally independent on the number of multiplexed antibodies, which indicates that the data quality does not suffer from combining multiple antibodies on one sample. The results suggests that competition between antibody DNA-conjugates over antibody-binding sites or restriction-ligation motifs does not play a significant role on a genome-wide level for this combination of epitopes.

TABLE 4 antibodies

| | Target | Host | Vendor | Catalog number | Optimal working concentration |
|---|---|---|---|---|---|
| Primary antibodies used in combination with secondary antibody-DNA conjugates | | | | | |
| Anti-Lamin B1 antibody - Nuclear Envelope Marker | Lamin B1 | Rabbit | Abcam | ab16048 | 10 μg/mL |
| Histone H3K9me2 antibody (pAb) | H3K9me2 | Rabbit | Active Motif | 39041 | 1 in 100 dilution |
| H3K9me3 Recombinant Rabbit Monoclonal Antibody (RM389) | H3K9me3 | Rabbit | Invitrogen | MA5-33395 | 5 μg/mL |
| Tri-methyl-histone-H3 (Lys27) Rabbit mAb | H3K27me3 | Rabbit | Cell Signaling Technologies | 9733S | 1 in 200 dilution |
| Recombinant Anti-Histone H3 (tri methyl K27) antibody [EPR18607] - BSA and Azide free | H3K27me3 | Rabbit | Abcam | ab222481 | 5 μg/mL |
| Anti-Trimethyl-Histone H3 (Lys36) antibody, clone RM155 | H3K36me3 | Rabbit | RevMab | 31-1051-00 | 0.5-1 μg/mL |
| Histone H3 trimethyl K36 antibody | H3K36me3 | Mouse | Homemade, gift by Hiroshi Kimura, Tokyo Institute of Technology | CM333 | 2 μg/mL |
| H3K4me3 Monoclonal Antibody (G.532.8) | H3K4me3 | Rabbit | Invitrogen | MA5-11199 | 121-242 ng/mL |
| Histone H3 (mono methyl K4) antibody | H3K4me1 | Rabbit | Abcam | ab8895 | 10 μg/mL |
| Recombinant Anti-Histone H3 (acetyl K27) antibody [EP16602] | H3K27ac | Rabbit | Abcam | ab177178 | 7 μg/mL |
| Recombinant Anti-RNA polymerase II CTD repeat YSPTSPS (phospho S5) antibody [3E8] | RNA Polymerase II CTD repeat Ser5 Phosphorylation | Rat | Abcam | ab252852 | 5 μg/mL |
| Histone H3 Antibody | Histone H3 | Sheep | Novus Biologicals | NB100-747 | 25 μg/mL |
| Secondary antibody-DNA conjugates | | | | | |
| AffiniPure Goat Anti-Rabbit IgG (H + L) | Rabbit IgG | Goat | Jackson ImmunoResearch | 111-005-144 | 2 μg/mL |
| AffiniPure Donkey Anti-Rabbit IgG (H + L) | Rabbit IgG | Donkey | Jackson ImmunoResearch | 711-005-152 | 2 μg/mL |
| AffiniPure Donkey Anti-Mouse IgG (H + L) | Mouse IgG | Donkey | Jackson ImmunoResearch | 715-005-150 | 2 μg/mL |
| AffiniPure Donkey Anti-Rat IgG (H + L) | Rat IgG | Donkey | Jackson ImmunoResearch | 712-005-150 | 2 μg/mL |
| AffiniPure Donkey Anti-Sheep IgG (H + L) | Sheep IgG | Donkey | Jackson ImmunoResearch | 713-005-147 | 2 μg/mL |
| Primary antibody-DNA conjugates | | | | | |
| Anti-Lamin B1 antibody - Nuclear Envelope Marker | Lamin B1 | Rabbit | Abcam | ab16048 | 20-30 μg/mL |
| H3K9me3 Recombinant Rabbit Monoclonal Antibody (RM389) | H3K9me3 | Rabbit | Invitrogen | MA5-33395 | 10-15 μg/mL |
| Recombinant Anti-Histone H3 (tri methyl K27) antibody [EPR18607] - BSA and Azide free | H3K27me3 | Rabbit | Abcam | ab222481 | 20 μg/mL |
| Anti-Trimethyl-Histone H3 (Lys36) antibody, clone RM155 | H3K36me3 | Rabbit | RevMab | 31-1051-00 | 10-20 μg/mL |
| H3K4me3 Monoclonal Antibody (G.532.8) | H3K4me3 | Rabbit | Invitrogen | MA5-11199 | 10 μg/mL |
| Histone H3 (mono methyl K4) antibody | H3K4me1 | Rabbit | Abcam | ab8895 | 10-15 μg/mL |
| Recombinant Anti-Histone H3 (acetyl K27) antibody [EP16602] | H3K27ac | Rabbit | Abcam | ab177178 | 20-30 μg/mL |

Comparing Data Between Single- and Multi-Antibody Samples

The MAb-ID data from 1000 K562 nuclei was obtained. The sample was stained individually for each antibody (single) or for all four antibodies combined (multi). To make an unbiased assessment, the sequencing depth for single and combined samples per target was equalized by discretely down-sampling the more deeply sequenced samples (FIG. 13A). UMAP visualization of all the individual and combined MAb-ID samples shows grouping based on chromatin target and is irrespective of the number of antibodies multiplexed within the sample. Biological replicates again have a high concordance with each other and unique read numbers as well as general statistics of the MAb-ID reads are Comparing Genomic Profiles Single- and Multi-Antibody Samples The local profiles of MAb-ID signal from individual and multiplexed samples have matching patterns on both a broad and more narrow genomic scale. At the same time, the enrichment of signal over corresponding genome-wide ChIP-seq peaks is similar for single and combined samples, which also holds for the depletion of signal over the unrelated ChIP-seq peaks. Together, the results of this example show that the on-target specificity of the antibodies is not affected by multiplexing them together in the same sample, nor is there a decrease in general data quality. Thus, MAb-ID enables identification of the genomic localization of four different epitopes in a multiplexed assay.

Example 4—Results

Utilization of an Alternative Pair of Restriction Enzymes

Thus far, experiments were typically performed using a combination of MseI and NdeI. In order to show the compatibility of the method as disclosed herein with an alternative pair of restriction enzymes, a combination of preferably MboI & BglII instead of MseI and NdeI was used. This combination of restriction enzymes was chosen because of 1) the high efficiency of MboI to digest cross-linked chromatin (Belaghzal, H., Dekker, J. & Gibcus, J. H. *Methods* 123, 56-65 (2017) and Sanborn, A. L. et al. *Proc. Natl. Acad. Sci. U.S.A* 112, E6456-65 (2015)), 2) the different genomic distribution of the GATC recognition motif compared to the TTAA motif (FIG. 14) the compatibility of the nucleotide overhangs that remain after MboI and BglII digestion. To prevent digestion of the GATC motif within the BglII recognition site by MboI in the genomic digestion step, the adenine of the motif on the bottom strand of the antibody-adapter was methylated. The hemi-methylated $G^{m6}ATC$ sequence is no longer recognized and digested by MboI, but the modification does not decrease BglII digestion efficiency. This approach offers the possibility to adapt MAb-ID in accordance with the expected enrichment of genomic motifs for the epitope of interest. In addition, this format enables the use of both versions of the antibody-adapter (either NdeI- or BglII-compatible) in the same reaction to theoretically increase the signal and resolution per sample. Despite slight differences in genomic motif distributions, all MAb-ID samples display the expected clustering per target, regardless of the choice of digestion-pair. The signal was also unaffected by simultaneous digestion with both pairs of enzymes in case both types of secondary antibody-DNA conjugates are used per epitope. Based on the results in this example, the type of antibody-adapter based on the enrichment of the digestion motif at the expected genomic location of the epitope of interest can be selected.

Example 5—Results

Primary Antibody-DNA Conjugates Increase the Multiplexin Potential of MAb-ID

Figure 14:
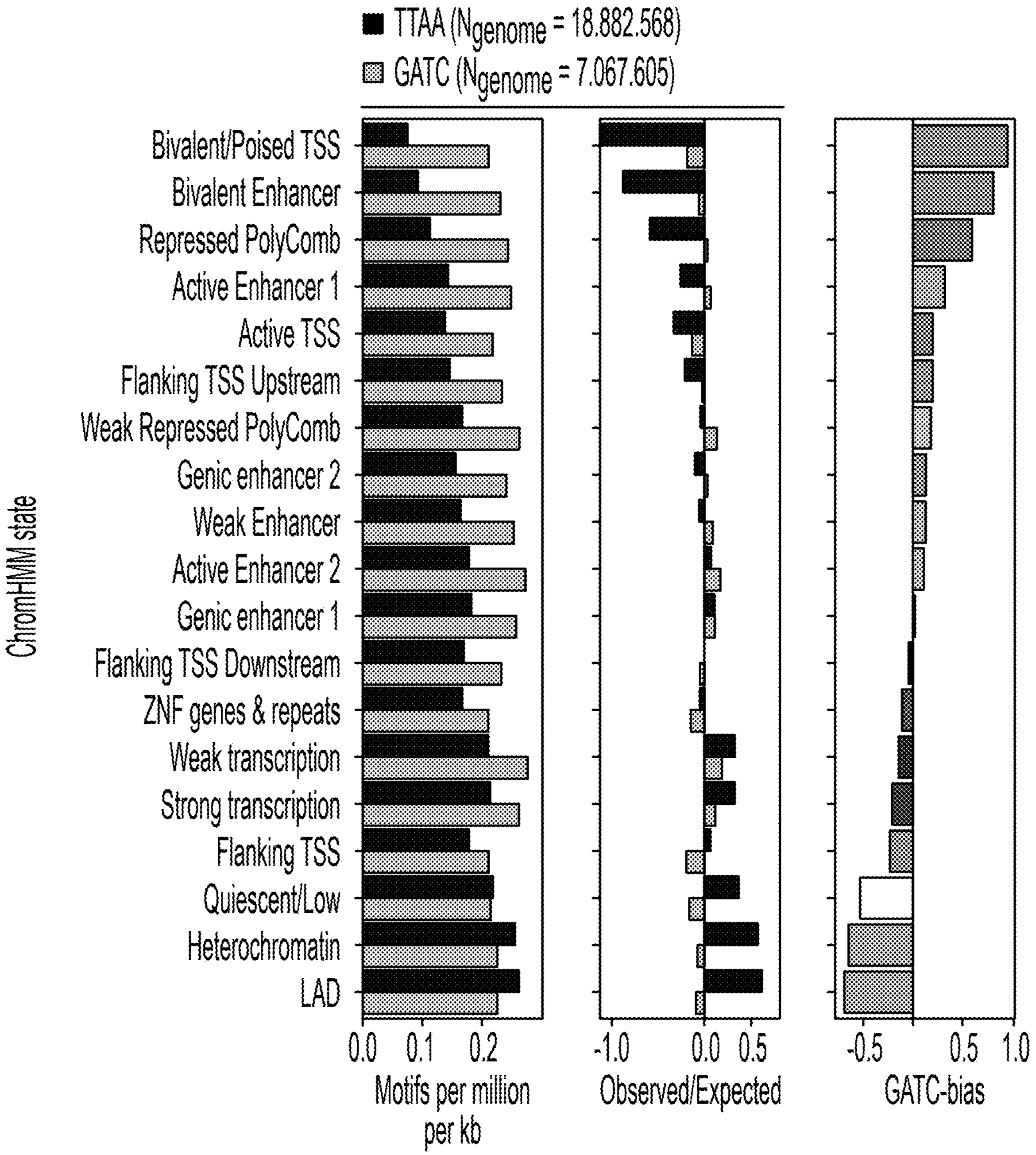
FIG. 14: Enrichment of TTAA and GATC sequence motifs in different genomic regions (based on ChromHMM domain calls). Observed/Expected is calculated based on the total amount of motifs in the genome. GATC-bias indicated the relative abundance of the GATC over TTAA motif, corrected for the total amount of motifs in the genome.
Figure 15:
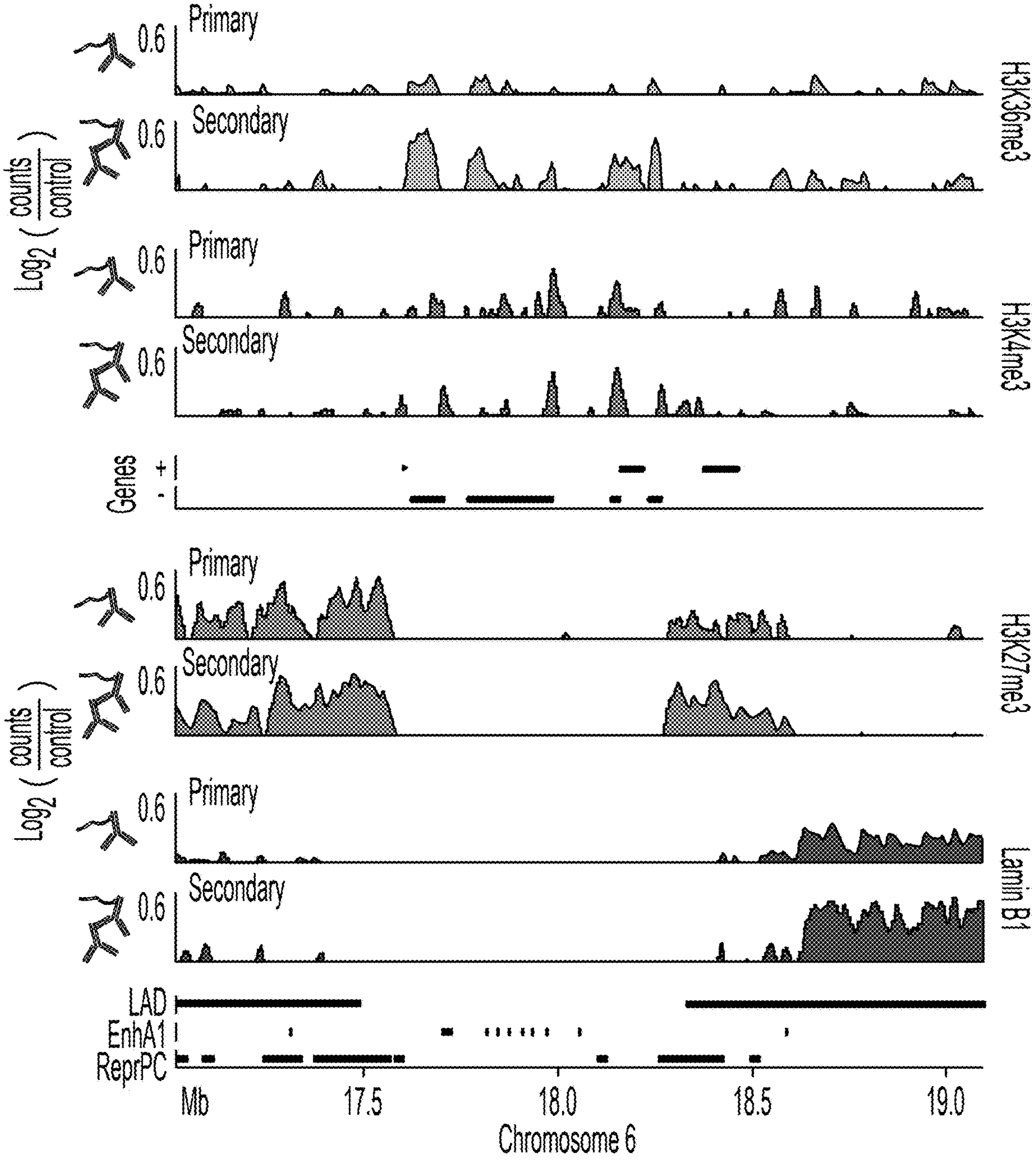
FIG. 15: Genomic profiles of MAb-ID samples generated with primary antibody-DNA conjugates or primary antibodies together with secondary antibody-DNA conjugates along a larger region of chromosome 13 and a smaller region of chromosome 6. ChromHMM calls are indicated at the bottom. MAb-ID data is normalized over control samples.

To expand the multiplexing potential of the method as disclosed herein, also referred to as MAb-ID, even further, antibody-adapters were conjugated directly to primary antibodies. This is more challenging than producing secondary antibody-DNA conjugates, since it is less cost-effective, only one antibody binds per epitope and the conjugation procedure could potentially affect the epitope-specificity of the antibody. Nevertheless, this overcomes the dependency on the host-origin of the antibody, the theoretical multiplexing potential of primary antibody-DNA conjugates is infinite and would allow profiling of all known chromatin types together in one sample. Primary antibodies were selected against a variety of chromatin types and conjugating each to a uniquely barcoded antibody-adapter. The conjugation procedure was slightly modified to account for the different buffer compositions of the primary antibodies and the type of antibody-adapter was selected based on the relative TTAA or GATC motif enrichment in the corresponding chromatin type (FIG. 14). MAb-ID stainings with individual primary antibody-DNA conjugates were performed in biological replicates of 1000 K562 cells to validate these against MAb-ID data obtained with secondary antibody-DNA conjugates as well as publicly available ChIP-seq datasets. The genomic profiles have a high similarity to the corresponding MAb-ID data using secondary antibody-DNA conjugates and are largely overlapping with ChIP-seq data (FIG. 15). Technical replicates using primary antibody-DNA conjugates cluster with the respective MAb-ID data from secondary antibody-DNA conjugates upon UMAP visualization, indicating a global correspondence between the datasets.

Based on the data quality of the individually stained samples, the six best primary antibody-DNA conjugates covering a set of different chromatin types were selected for combined MAb-ID experiments. To this end, K562 cells were simultaneously incubated with all of these primary antibody-DNA conjugates and sorted as 100 nuclei samples in 384-well plates. The combined samples group together in UMAP space with the previously generated individual samples, which verifies the general similarity between the sample types. Thus, the direct conjugation of antibody-adapters to primary antibodies offers extensive multiplexing potential with similar data quality and allows profiling of an increasingly complex set of chromatin types and epigenetic states.

Example 6—Results

Simultaneous Epigenetic Profiles at Single-Cell Resolution

Figure 16A:
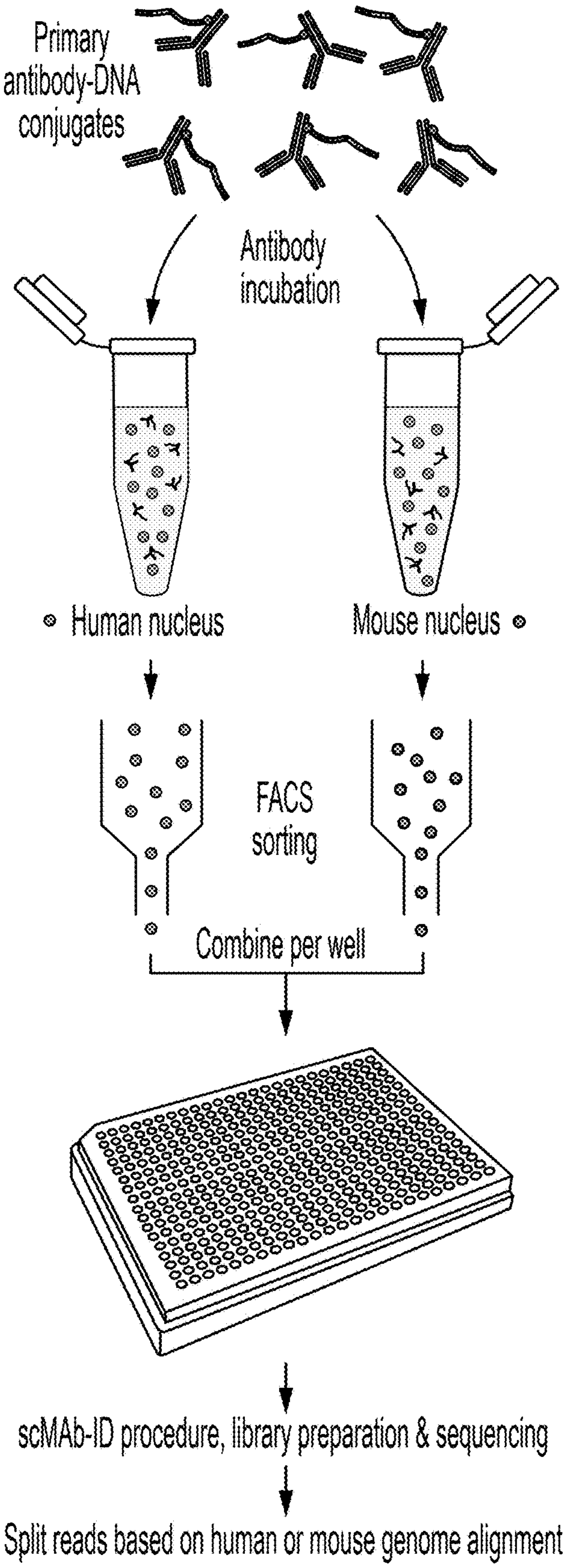
FIGS. 16A-16C: Schematic of scMAb-ID set-up sorting K562 and mouse cells together in each well. Stainings were done using primary antibody-DNA conjugates in combined fashion (FIG. 16A). Unique read count numbers as total per cell or per epitope (FIG. 16B). Genomic profiles of K562 scMAb-ID and bulk MAb-ID samples generated with combinations of primary antibody-DNA conjugates along chromosome 9. Gene calls are indicated at the bottom. MAb-ID data is normalized over control samples, ChIP-seq is normalized over input (FIG. 16C)

The multiplexing of several measurements in small cell populations can benefit the reduction of technical biases between samples and be highly valuable in situations where limited input material is available. Nevertheless, by performing these measurements in single-cells, one can obtain even more insight into the interplay between epigenetic states and gene regulatory processes. the method as disclosed herein, also referred to as MAb-ID, was used to generate simultaneous epigenetic profiles at a single-cell resolution (may also be referred to in the figures as "scMAb-ID"), by sorting in 384-well PCR plates and using liquid-handling robots to increase throughput and reduce sample handling. 384 unique sample-adapters were designed and sorted one nucleus of human origin with one of mouse origin in each of the well of the 384-well PCR plates (FIG. 16A). Assignment of reads to either the human or mouse cell is achieved by aligning the reads to a hybrid genome. When testing this approach with control datasets containing only human or mouse cells as input, the median amount of wrongly assigned reads was below 0.4%, indicating that this is a robust approach to assign the cell of origin.

Figure 16B:
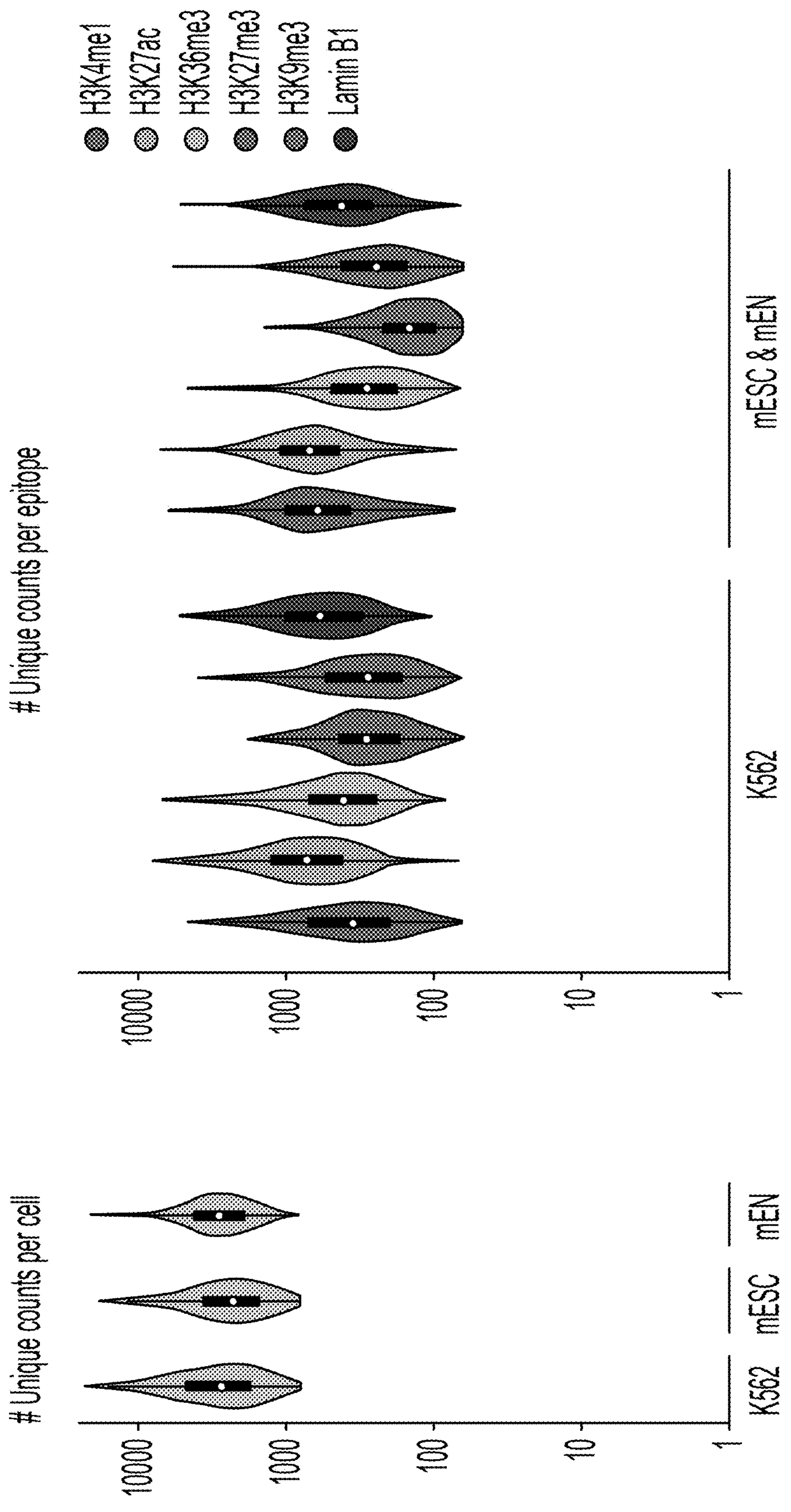

To examine the capacity of MAb-ID to discern epigenetic states in different cell types, mouse embryonic stem cells (mESCs) were differentiated towards the neural lineage for a total of six days by following a standard in vitro differentiation protocol. Subtle but significant differences in their epigenetic profiles were expected despite being at a very early stage of differentiation. These early neural cells (mEN) were harvested side-by-side with mESCs and human K562 cells and stained using a combined set of six different primary antibody-DNA conjugates against a range of epitopes for active and inactive chromatin types. The nuclei of these three cell types were sorted as small cell populations or single cells in each well of a 384-well plate, which were pooled together during the single cell MAb-ID processing and submitted for sequencing, preferably next-generation sequencing. A total number of 1956 K562, 1424 mESC and 1424 mEN single cells were sequenced and of these respectively 1248, 674 and 849 cells passed the quality thresholds based on a minimal amount of unique counts per cell as well as per epitope. The median number of unique counts per cell after filtering was 2715.5 for K562, 2281.5 for mESC and 2842 for mEN cells, with a median of unique counts per epitope in each cell ranging from 119 to 706.5 (FIG. 16B). Even though the data is relatively sparse, these numbers are in a similar range to those reported by other recent multimodal methods measuring several histone PTMs simultaneously (Gopalan, S et al., Simultaneous profiling of multiple chromatin proteins in the same cells. *Mol. Cell* 81, 4736-4746.e5 (2021)).

Figure 16C:
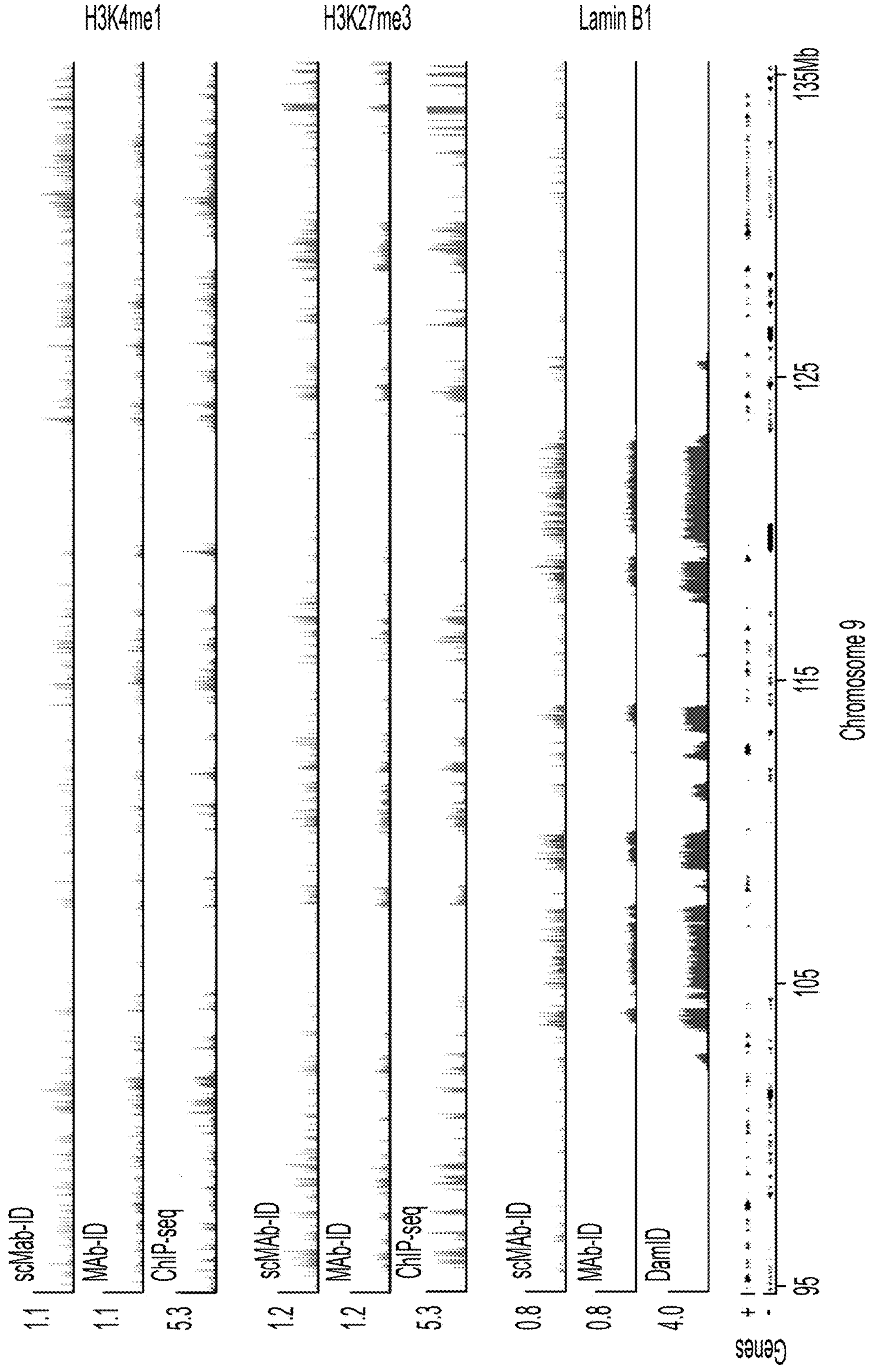

The unique reads of all K562 cells were combined to generate in silico populations and compare these to bulk (i.e. non-single cell) MAb-ID datasets. The local genomic profiles of MAb-ID and scMAb-ID signal are very similar to each other as well as corresponding ChIP-seq datasets (FIG. 16C). At a genome-wide level, scMAb-ID signal is enriched at corresponding peaks and domains from ChIP-seq datasets, which indicates that the specificity for the epitope is maintained at single-cell resolution. Visualization using UMAP shows the scMAb-ID samples clustering together with their bulk MAb-ID counterparts, verifying the genome-wide similarity between these datasets. To confirm that the reads from each single cell hold enough information to separate epigenetic state UMAP clustering of the single K562 cells was performed epitope-specific data per cell was treated separately and representing each cell once for each of the multiplexed measurements, the cells clearly separate based on epitopes. The clustering is independent of both the total read depth per cell as well as per epitope, indicating that the information is specific to the used primary antibody-DNA conjugate. Together, these results validate the ability of scMAb-ID to distinguish epigenetic profiles at a single-cell resolution in a multiplexed set-up.

Example 7—Results

Figure 17A:
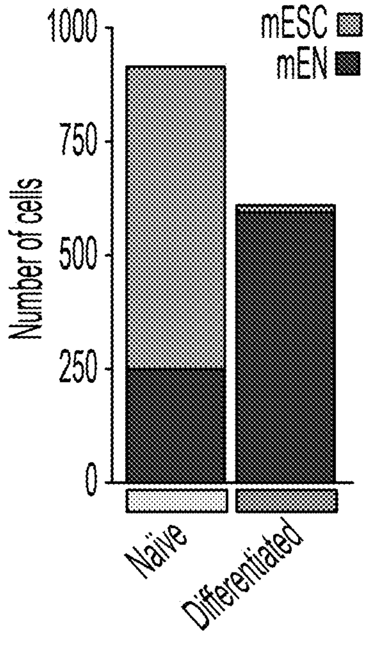
FIGS. 17A-17B: Barplot with numbers of mESC or mEN cells located in the naïve or differentiated cluster (FIG. 17A) and ratio in unique read counts over the assigned active or inactive X-allele in the mESC or mEN cells for the different epitopes (FIG. 17B).

Integration of Epitope-Specific Datasets from Single Cells Enables Identification of Epigenetic States To explore whether single-cell MAb-ID holds the potential to discern relatively similar cell types based on their multiplexed epigenetic profiles. Local genomic profiles of combined in silico populations of all mESCs are similar to those of publicly available datasets. This indicates that single-cell MAb-ID data quality is similar for cells from both human and mouse species. Multiplexing of all epitope measurements together within a single cell allows us to integrate these datasets together, which could aid in further distinguishing the cell types and would enable studying the epigenetic states relative to each other. To this end, an integrated dataset was computed containing the combined epigenetic information for each cell, based on the theoretical work of Zhu et al. from 2021 (Zhu, C. et al. *Nat. Methods* 18, 283-292 (2021)). When using this joined dataset to cluster the cells, these indeed mainly separate based on their origin from either the mESC or mEN population. Interestingly, by assigning the cells to one of two groups using Leiden-clustering, we can identify cells in the mEN population that appear to have maintained their more naïve cell state (FIG. 17A). Likewise, but to a much lesser extent, cells in the mESC population that seem to have already acquired a more differentiated cell state, as expected in these culturing conditions (FIG. 17A). To unbiasedly assess whether the same assignment of cell states could be acquired without the integration of all epitope measurements, the Information Gain was computed upon clustering with different combinations of epitopes using the principle of Shannon Entropy from information theory. Unsurprisingly, the H3K27me3 and H3K4me1 measurements contributed most to the assignment of the naïve and differentiated cell states, as these are known to be valuable predictors of cell type and developmental stage.

Since the female mESCs should randomly inactive one of their X-chromosomes while differentiating towards the neural lineage, it was identified which cells had already undergone this process. As this developmental phenomenon occurs randomly for each cell, establishing which allele has been inactivated requires both single-cell information and distinctive features between the two alleles. The mESCs originate from a hybrid cross between mice from two distinct genotypes (Cast/EiJ×129SvJae), and the high frequency of known SNPs between these genotypes allows the assignment of approximately 35-40% of the reads per cell to either the paternal or maternal genome. Upon random inactivation, the inactive X-allele (Xi) is known to have an overall strong increase in H3K27me3 levels compared to the allele that remains active (Xa) (Okamoto, I., Otte, A. P., Allis, C. D., Reinberg, D. & Heard, E. *Science* 303, 644-649 (2004) and Rougeulle, C. et al., *Mol. Cell. Biol.* 24, 5475-5484 (2004)). Therefore, the ratio of unique H3K27me3 counts between the two X-alleles was calculated to establish whether the cells had undergone X-chromosome inactivation and which allele had been inactivated. After projecting this status onto the clusters from the integrated dataset, it was observed that most of the cells that have inactivated one of the X-chromosomes are present in the differentiated cluster. In UMAP space these cells appear to be located furthest away from the naïve cells, indicating that the integrated dataset potentially holds information on the progression throughout the differentiation trajectory, rather than just the start and end point.

Figure 17B:
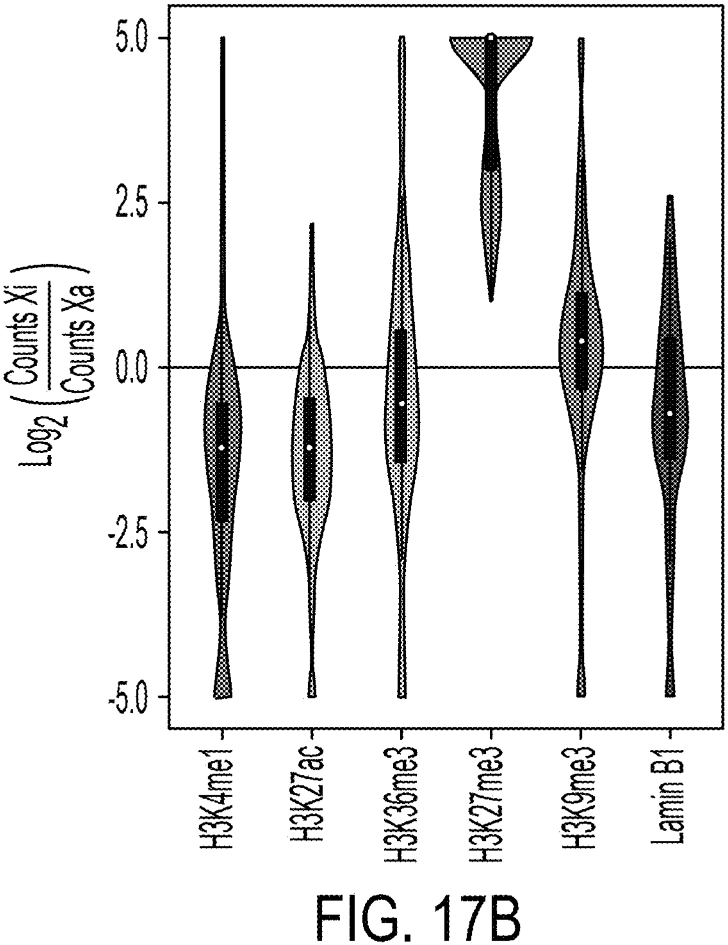

As the dataset is generated with the multiplexed measurements, the ratio in unique count levels between the identified Xi and Xa alleles for the other epigenetic states were calculated as well. As the H3K27me3 levels on the Xi allele are strongly increased, the levels of the active chromatin types such as H3K27ac are decreased, albeit to a lower level (Boggs, B. A., Connors, B., Sobel, R. E., Chinault, A. C. & Allis, C. D. *Chromosoma* 105, 303-309 (1996)) (FIG. 17B). The H3K9me3 levels are slightly increased on the Xi-allele, as has been previously reported (Boggs, B. A. et al., *Nat. Genet.* 30, 73-76 (2002) and Heard, E. et al., *Cell* 107, 727-738 (2001)) (FIG. 17B). These results highlight that MAb-ID can discern epigenetic states in single cells by multiplexing several measurements. By simultaneously profiling epigenetic states in each cell, the interplay between the chromatin types can be further explored, especially for heterogeneous developmental processes that are difficult to study with bulk assays.

The invention claimed is:

1. A method of detecting a target genomic DNA that binds to a polypeptide of interest among a plurality of genomic DNA, the method comprising:

(a) providing:

(i) a sample comprising a plurality of cells that comprise the plurality of genomic DNA, wherein the plurality of cells are permeabilized and fixated;

(ii) an antibody-DNA adapter conjugate that comprises:

(1) an antibody that directly or indirectly binds to the polypeptide of interest that binds to the target genomic DNA, and (2) a first DNA adapter that comprises a first barcode sequence, a first end, and a second end, wherein the first DNA adapter is linked to the antibody;

(iii) a second DNA adaptor that comprises a second barcode sequence, a third end, and a fourth end;

(b) contacting the sample with a restriction enzyme, wherein the contacting results in fragmentation of the plurality of genomic DNA into a plurality of DNA fragments that each comprises an end that is configured to bind to the first end of the first DNA adapter;

(c) contacting the sample containing the plurality of DNA fragments with the antibody-DNA adapter conjugate, wherein the contacting results in the antibody of the antibody-DNA adaptor conjugate binding directly or indirectly to the polypeptide of interest that is bound to the target genomic DNA, thereby resulting in localization of the first DNA adaptor to the target genomic DNA;

(d) ligating the first end of first DNA adapter to the target genomic DNA via the end produced by the restriction enzyme in (b);

(e) ligating the third end of the second DNA adapter to the second end of the first DNA adapter via an end-to-end base pairing; and (f) sequencing the target genomic DNA ligated to the first DNA adaptor and the second DNA adaptor; wherein the sequencing results in detection of the target genomic DNA among the plurality of genomic DNA;

wherein the second DNA adaptor increases detection sensitivity of the antibody-DNA adapter conjugate relative to a corresponding antibody-DNA adapter conjugate without the second DNA adaptor.

2. The method of claim 1, wherein the restriction enzyme of step (b) produces a blunt end on the target genomic DNA after contacting the sample, and wherein the blunt end is modified to produce an overhang that binds to the first end of the first DNA adaptor.

3. The method of claim 1, wherein the antibody of the antibody-DNA adapter conjugate is a primary antibody that directly binds to the polypeptide of interest.

4. The method of claim 3, wherein a plurality of the antibody-DNA adaptor conjugates are contacted with the sample in step (c), wherein each antibody-DNA adaptor conjugate of the plurality of antibody-DNA conjugates specifically binds to different polypeptides of interest.

5. The method of claim 4, wherein at least one antibody-DNA conjugate of the plurality of antibody-DNA conjugates specifically binds to a polypeptide of interest that has a modification with respect to a corresponding wild-type polypeptide.

6. The method of claim 4, wherein each primary antibody of the plurality of antibody-DNA adaptor conjugates is conjugated to a different DNA adapter, and wherein each DNA adapter of the plurality of antibody-DNA adapter conjugates comprises a unique first barcode sequence that uniquely identifies a particular primary antibody, and wherein the method further comprises multiplexing the plurality of antibody-DNA adapter conjugates, thereby profiling multiple polypeptides of interest in the sample simultaneously.

7. The method of claim 1, wherein prior to step (c) the method further comprises contacting the sample with a primary antibody that directly binds to the polypeptide of interest, and wherein the antibody of the antibody-DNA adaptor conjugate is a secondary antibody that indirectly binds to the polypeptide of interest.

8. The method of claim 7, wherein a plurality of different primary antibodies that specifically bind to different polypeptides of interest are contacted with the sample.

9. The method of claim 8, wherein the antibody-DNA adaptor conjugate comprises a plurality of different antibody-DNA adapter conjugates, and wherein each DNA adapter of the plurality of antibody-DNA adapter conjugates comprises a unique first barcode sequence that uniquely identifies a particular primary antibody.

10. The method of claim 9, further comprising multiplexing the plurality of different primary antibodies and the plurality of different antibody-DNA adapter conjugates, thereby profiling multiple polypeptides of interest in the sample simultaneously.

11. The method of claim 1, wherein prior to sequencing the method further comprising amplifying a product of (e) to obtain an amplified product.

12. The method of claim 1, wherein the first barcode sequence uniquely identifies the antibody of the antibody-DNA adapter conjugate.

13. The method of claim 1, wherein the antibody of the antibody-DNA adapter conjugate is conjugated to a plurality of first DNA adapters.

14. The method of claim 13, wherein at least two first DNA adaptors among the plurality of first DNA adaptors that are conjugated to the antibody of the antibody-DNA adaptor conjugate are different.

15. The method of claim 1, wherein the second barcode sequence uniquely identifies the sample.

16. The method of claim 1, wherein the polypeptide of interest comprises a histone, a DNA polymerase, an RNA polymerase, a transcription factor, a nuclease, a high-mobility group protein, a nucleosome remodeler, a nuclear structural protein, a DNA damage repair protein, a histone modifying enzyme, a component of a chromatin complex, a chromatin structural protein, or a histone chaperone.

17. The method of claim 1, further comprising: (i) generating a genome-wide protein-DNA interaction profile and a genome-wide epigenetic profile among different cell-types, and (ii) comparing: the genome-wide protein-DNA interaction profile and genome-wide epigenetic profile between diseased and healthy cells; samples from different disease stages; or diseased samples from different treatment regimes.

18. The method of claim 1, wherein the second adaptor facilitates analysis of multiple polypeptides of interest from a single cell after pooling, thereby identifying interactions between the target genomic DNA and the polypeptide of interest associated with cellular identities.

19. A system for detecting a target genomic DNA that binds to a polypeptide of interest among a plurality of cells that contain a plurality of nuclear targets, the system comprising:

(a) a sample comprising the plurality of cells that are permeabilized and fixated;

(b) a first cutting moiety that is configured to produce an end on the nuclear target upon contacting with the sample;

(c) a binding molecule-oligo adapter conjugate that comprises a binding molecule and a first oligo adapter, wherein the binding molecule directly or indirectly binds to a polypeptide of interest that binds specifically to the nuclear target and wherein the oligo adapter comprises:

(i) a first identifying sequence;

(ii) a first end that is configured to bind to the end of the nuclear target from (b);

(iii) a second end;

(d) a joiner that joins the oligo adapter to the nuclear target;

(e) a second oligo adapter comprising a second barcode sequence, a third end that binds to the second end of the first oligo adapter via an end-to-end base pairing, and a fourth end; and (f) reagents for amplifying and sequencing;

wherein the second oligo adaptor increases detection sensitivity of the molecule-oligo adapter conjugate relative a corresponding molecule-oligo adapter conjugate without the second oligo adaptor.

20. The system of claim 19, wherein the binding molecule comprises an antibody, and wherein the antibody is a primary antibody, primary antibody fragment thereof, or a secondary antibody, wherein the primary antibody or primary antibody fragment thereof comprises a monoclonal antibody, a recombinant, a polyclonal antibody, a chimeric antibody, human antibody, a humanized antibody, a multispecific antibody, an immunoglobulin-like domain, a single variable domain, antigen binding antibody fragments, or modifications thereof.

* * * * *